(12) United States Patent
Jarikov et al.

(10) Patent No.: US 7,175,922 B2
(45) Date of Patent: *Feb. 13, 2007

(54) AGGREGATE ORGANIC LIGHT EMITTING DIODE DEVICES WITH IMPROVED OPERATIONAL STABILITY

(75) Inventors: Viktor V. Jarikov, Rochester, NY (US); J. Ramon Vargas, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 102 days.

This patent is subject to a terminal disclaimer.

(21) Appl. No.: 10/691,326

(22) Filed: Oct. 22, 2003

(65) Prior Publication Data

US 2005/0106415 A1   May 19, 2005

(51) Int. Cl.
*H01L 51/50* (2006.01)
*H05B 33/00* (2006.01)

(52) U.S. Cl. .................. 428/690; 428/917; 313/504; 313/506

(58) Field of Classification Search ............ 428/690, 428/917; 313/504, 506
See application file for complete search history.

(56) References Cited

U.S. PATENT DOCUMENTS

| | | | |
|---|---|---|---|
| 4,769,292 A | 9/1988 | Tang et al. | |
| 5,141,671 A | 8/1992 | Bryan et al. | |
| 5,281,489 A * | 1/1994 | Mori et al. | 428/690 |
| 5,593,788 A | 1/1997 | Shi et al. | |
| 5,747,183 A | 5/1998 | Shi et al. | |
| 5,908,581 A | 6/1999 | Chen et al. | |
| 6,392,250 B1 * | 5/2002 | Aziz et al. | 257/40 |
| 2003/0118866 A1 * | 6/2003 | Oh et al. | 428/690 |
| 2003/0137241 A1 * | 7/2003 | Fujita et al. | 313/504 |
| 2004/0076853 A1 | 4/2004 | Jarikov | |

FOREIGN PATENT DOCUMENTS

| | | |
|---|---|---|
| EP | 1 162 674 | 12/2001 |
| EP | 1221473 | 7/2002 |
| EP | 1317005 | 6/2003 |
| EP | 1359790 | 11/2003 |
| JP | 99273861 A | 3/1998 |
| JP | 01284050 A | 3/2000 |

OTHER PUBLICATIONS

"Organic electroluminescent diodes" by C.W. Tang et al., Applied Physics Letter 51 (12) Sep. 21, 1987, pp. 913-915.

(Continued)

*Primary Examiner*—Dawn Garrett
(74) *Attorney, Agent, or Firm*—Raymond L. Owens

(57) ABSTRACT

An organic light emitting device includes a substrate, an anode and a cathode disposed over the substrate, and a luminescent layer disposed between the anode and the cathode wherein the luminescent layer includes a host and at least one dopant. The host of the luminescent layer is selected to include a solid organic material comprising a mixture of at least two components, one of which contains at least one perylene carbocyclic ring structure or at least one mono-aza-perylene or poly-aza-perylene ring structure and is capable of forming both monomer state and an aggregate state.

145 Claims, 4 Drawing Sheets

OTHER PUBLICATIONS

"Red organic light-emitting diodes using an emitting assist dopant" by Yuji Hamada et al., 1999 American Institute of Physics, Sep. 20, 1999, pp. 1682-1684.

"Improving the efficiency and stability of organic light emitting devices by using mixed emitting layers" by Zoran D. Popovic, et al, SPIE Conference on Organic Light-Emitting Materials and Devices, San Diego, California Jul. 1998, SPIE vol. 3476, pp. 68-73.

"Electroluminescence of doped organic thin films" by C.W. Tang et al., Journal Applied Physics 65 (9), May 1, 1989, pp. 3610-3616.

"Double injection electroluminescence in anthracene" by J. Dresner, RCA Review Jun. 1969, p. 322-334.

J. Kalinowski et al "Voltage-induced evolution of emission spectra in organic light-emitting diodes", J. of Appl. Phys. Amer. Ins. of Physics, NY V. 83, No. 8, Apr. 15, 1998, pp. 4242-4248.

H. Kjima et al, "A structural study for highly efficient electroluminescene cells using perylene-doped organic materials", J. Elelctrochem.Soc., vol. 144, 1997, pp. 3628-3633.

* cited by examiner

AGGREGATE ORGANIC LIGHT EMITTING DIODE DEVICES WITH IMPROVED OPERATIONAL STABILITY

CROSS REFERENCE TO RELATED APPLICATIONS

Reference is made to commonly assigned U.S. patent application Ser. No. 10/131,801 filed Apr. 24, 2002 (now abandoned) by Viktor V. Jarikov, entitled "Organic Light-Emitting Diode Devices With Improved Operational Stability"; and commonly assigned U.S. patent application Ser. No. 10/690,940 filed Oct. 22, 2003 by Tukaram K. Hatwar et al., entitled "A Stabilized White-Light-Emitting OLED Device"; the disclosures of which are herein incorporated by reference.

FIELD OF THE INVENTION

The present invention relates to organic light emitting diode devices and more particularly to the design of the composition of the organic layers for improvements in operational stability.

BACKGROUND OF THE INVENTION

Organic light emitting diodes (OLED), also known as organic electroluminescent (EL) devices, are a class of electronic devices that emit light in response to an electrical current applied to the device. The structure of an OLED device generally includes an anode, an organic EL medium, and a cathode. The term, organic EL medium, herein refers to organic materials or layers of organic materials disposed between the anode and the cathode in the OLED device. The organic EL medium can include low molecular weight compounds, high molecular weight polymers, oligimers of low molecular weight compounds, or biomaterials, in the form of a thin film or a bulk solid. The medium can be amorphous or crystalline. Organic electroluminescent media of various structures have been described in the prior art. Dresner, in RCA Review, 30, 322 (1969), described a medium comprising a single layer of anthracene film. Tang et al., in Applied Physics Letters, 51, 913 (1987), Journal of Applied Physics, 65, 3610 (1989), and commonly assigned U.S. Pat. No. 4,769,292, reported an EL medium with a multi-layer structure of organic thin films, and demonstrated highly efficient OLED devices using such a medium. In some OLED device structures the multi-layer EL medium includes a hole-transport layer adjacent to the anode, an electron-transport layer adjacent to the cathode, and disposed in between these two layers, a luminescent layer. Furthermore, in some preferred device structures, the luminescent layer is constructed of a doped organic film comprising an organic material as the host and a small concentration of a fluorescent compound as the dopant. Improvements in EL efficiency, chromaticity, and stability have been obtained in these doped OLED devices by selecting an appropriate dopant-host composition. The dopant, being the dominant emissive center, is selected to produce the desirable EL colors. Examples of the doped luminescent layer reported by Tang et al. in commonly assigned U.S. Pat. No. 4,769,292 and by Chen et al. in commonly assigned U.S. Pat. No. 5,908,581 are: tris(8-quinolinol)-aluminum (AlQ) host doped with coumarin dyes for green emitting OLEDs; and AlQ doped with 4-dicyanomethylene-4H-pyrans (DCMs) for orange-red emitting OLEDs. Shi et al., in commonly assigned U.S. Pat. No. 5,593,788, disclosed that a long operational life was obtained in an OLED device by using a quinacridone compound as the dopant in an AlQ host. Bryan et al., in commonly assigned U.S. Pat. No. 5,141,671, disclosed a luminescent layer containing perylene or a perylene derivative as a dopant in a blue emitting host. They showed that a blue emitting OLED device with an improved operational stability was obtained. In both disclosures, the incorporation of selected fluorescent dopants in the luminescent layer is found to improve substantially the overall OLED device performance parameters. Co-doping of luminescent layer with anthracene derivatives results in devices with better stability as shown in JP 99273861 and JP 284050. Doping the hole-transport layer with materials that impede hole-transport and co-doping hole-transport materials into electron-transporting AlQ leads to the improved device lifetimes, Popovic et al. Thin Solid Films 2000, 363, 6; SPIE 1998, 3476, 68.

The most common formulation of the doped luminescent layer includes only a single dopant in a host matrix. However, in a few instances, incorporation of more than one dopant in the luminescent layer was found to be beneficial in improving stability. Using a luminescent layer containing rubrene, a yellow emitting dopant, and DCJ, 4-(dicyanomethylene)-2-methyl-6-[2-(4-julolidyl)ethenyl]-4H-pyran, a red emitting dopant, in an AlQ host, it is possible to produce a red emitting OLED device with improved operational stability, Hamada et al. in Applied Phys. Lett. 75, 1682 (1999); EP 1162674. Here rubrene functions as a co-dopant in mediating energy transfer from the AlQ host to the DCJ emitter. Generally, in dual dopant systems, it has been noted that the operational stability tends to increase compared to that of the single dopant systems.

Although EL efficiency, color, and stability have been improved significantly using doped luminescent layers of various compositions, the problem of low operational stability persists. Insufficient stability presents the greatest obstacle for many desirable practical applications.

SUMMARY OF THE INVENTION

It is an object of the present invention to provide OLED devices with improved operational stability.

It is another object of the present invention to provide OLED devices with improved luminance efficiency.

It is another object of the present invention to provide a color OLED device with improved color chromaticity.

It is a further object of the present invention to provide specifically OLED devices with improved operational stability, luminance efficiency, and chromaticity.

These objects are achieved in an organic light emitting device comprising a substrate, an anode and a cathode disposed over the substrate, and a luminescent layer disposed between the anode and the cathode wherein the luminescent layer includes a host and at least one dopant, the host of the luminescent layer is selected to include a solid organic material comprising a mixture of at least two components, one of which is capable of forming both monomer state and an aggregate state.

These objects are further achieved in an organic light emitting device, comprising:
 a) a substrate;
 b) an anode and a cathode disposed over the substrate;
 c) a luminescent layer disposed between the anode and the cathode wherein the luminescent layer includes a host and at least one dopant;

d) the host of the luminescent layer being selected to include a solid organic material comprising a mixture of at least two components wherein:
   i) the first component of the mixture is an organic compound containing at least one perylene carbocyclic ring structure or at least one mono-aza-perylene or poly-aza-perylene ring structure that is capable of transporting either electrons or holes or both and is capable of forming both monomer state and an aggregate state and further is capable of forming the aggregate state either in the ground electronic state or in the excited electronic state that results in a different absorption or emission spectrum or both relative to the absorption or emission spectrum or both of the monomer state, respectively, or the first component of the mixture is an organic compound containing at least one perylene carbocyclic ring structure or at least one mono-aza-perylene or poly-aza-perylene ring structure that is capable of forming the aggregate state whose presence results in a quantum yield of luminescence of the monomer state being different relative to the quantum yield of luminescence of the monomer state in the absence of the aggregate state, and
   ii) the second component of the mixture is an organic compound that upon mixing with the first host component is capable of forming a continuous and substantially pin-hole-free layer; and
e) the dopant of the luminescent layer being selected to produce light from the light emitting device.

An advantage of the present invention is that, with an appropriate selection of the first and second host components and the dopants in the luminescent layer, OLED devices with extraordinarily long lifetimes are produced.

Another advantage of the present invention is that it provides OLED devices with high operational stability, lower drive voltage, excellent luminance efficiency and color chromaticity, and with luminance efficiency and color chromaticity essentially independent of the current density.

Another advantage of the present invention is that it provides OLED devices that are suitable for high-brightness and long-lifetime lighting and display applications.

BRIEF DESCRIPTION OF THE DRAWINGS

The drawings are necessarily of a schematic nature, since the individual layers are too thin and the thickness differences of the various elements too great to permit depiction to scale or to permit convenient proportionate scaling.

DETAILED DESCRIPTION OF THE INVENTION

Figure 1:
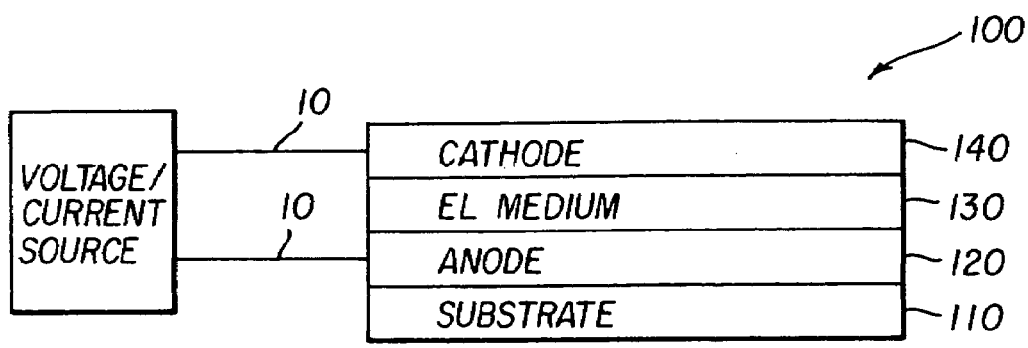
FIG. 1 is schematic structure of an OLED with an organic EL medium.

FIG. 1 illustrates the structure of an OLED device of the simplest construction practiced in the present invention. In this structure, OLED device 100 includes an anode 120, an EL medium 130, and a cathode 140, disposed upon a substrate 110. In operation, an electrical current is passed through the OLED by connecting an external current or voltage source with electrical conductors 10 to the anode and the cathode, causing light to be emitted from the EL medium. The light can exit through either the anode or the cathode or both as desired and depending on their optical transparencies. The EL medium includes a single layer or a multi-layer of organic materials.

Figure 2:
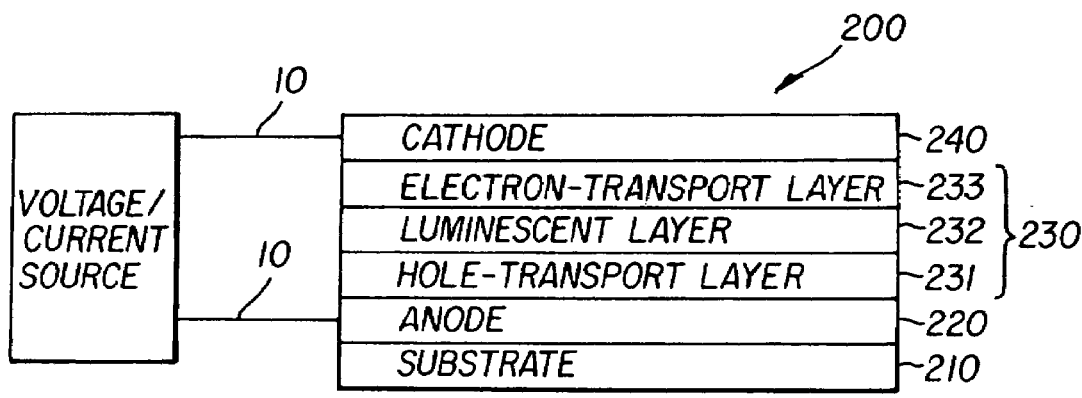
FIG. 2 and FIG. 3 are two schematic OLED structures showing two different configurations of the organic EL medium.

FIG. 2 illustrates the structure of another OLED device of the present invention. In this structure, OLED device 200 includes a substrate 210 and an EL medium 230, disposed between anode 220 and cathode 240. EL medium 230 includes a hole-transport layer 231 adjacent to the anode, an electron-transport layer 233 adjacent to the cathode, and a luminescent layer 232 disposed between the hole-transport layer and the electron-transport layer. In operation, an electrical current is passed through the OLED device by connecting an external current or voltage source with electrical conductors 10 to the anode and the cathode. This electrical current, passing through the EL medium, causes light to be emitted primarily from the luminescent layer 232. Hole-transport layer 231 carries the holes, that is, positive electronic charge carriers, from the anode to the luminescent layer. Electron-transport layer 233 carries the electrons, that is, negative electronic charge carriers, from the cathode to the luminescent layer 232. The recombination of holes and electrons produces light emission, that is, electroluminescence, from the luminescent layer 232.

Figure 3:
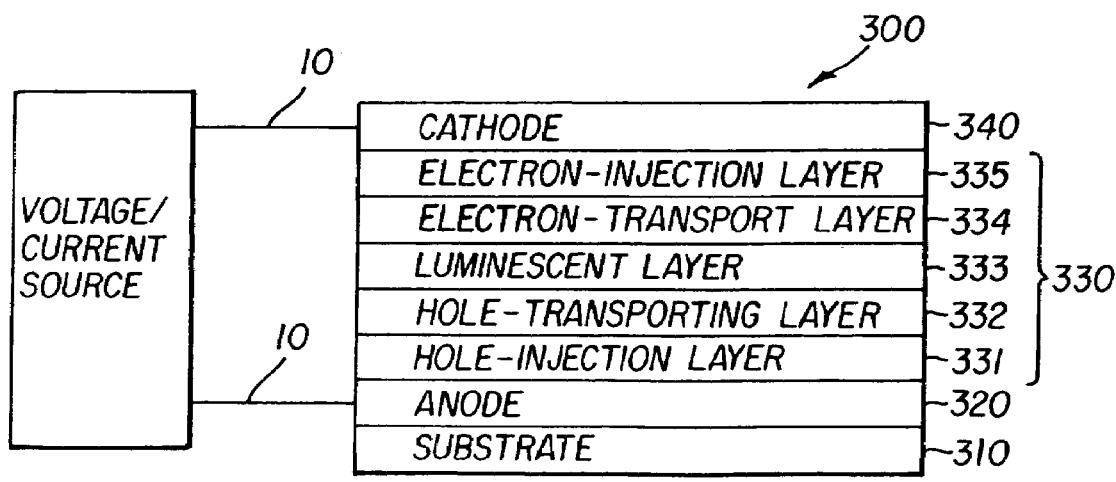

FIG. 3 illustrates yet another structure of an OLED device of the present invention. In this structure, OLED device 300 includes a substrate 310 and an EL medium 330 disposed between anode 320 and cathode 340. EL medium 330 includes a hole-injection layer 331, a hole-transport layer 332, a luminescent layer 333, an electron-transport layer 334, and an electron-injection layer 335. Similarly to OLED device 200 of FIG. 2, the recombination of electrons and holes produces emission primarily from the luminescent layer 333. The provision of the hole-injection layer 331 and the electron-injection layer 335 serves to reduce the barriers for carrier injection from the respective electrodes. Consequently, the drive voltage required for the OLED device can be reduced.

Figure 4:
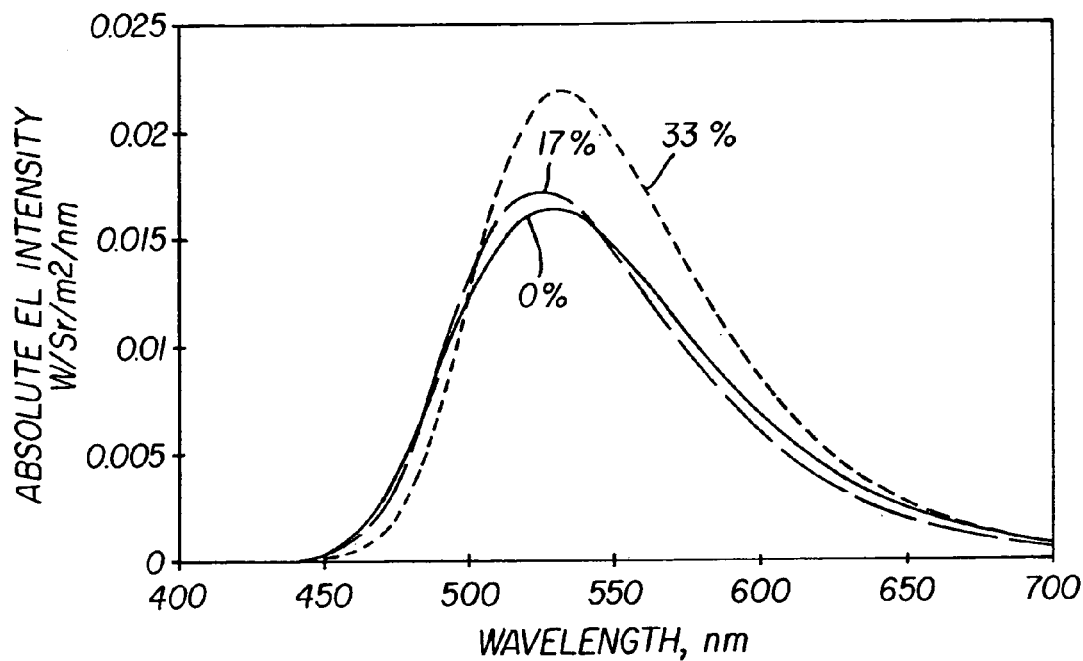
FIG. 4 shows electroluminescence spectra of an OLED device where the light emitting layer is composed of dibenzo[b,k]perylene and AlQ$_3$; current density is 20 mA/cm$^2$.

FIG. 4 shows the absolute EL spectra of an OLED device where the light emitting layer is composed of dibenzo[b,k]perylene and AlQ$_3$. It can be seen that the EL spectra signal major involvement of an aggregate state of dibenzo[b,k]perylene in EL production. Thus, the EL spectrum is composed primarily of the emission spectrum of dibenzo[b,k]perylene in its aggregate state while a small portion of EL comes from the emission of AlQ$_3$.

Figure 5:
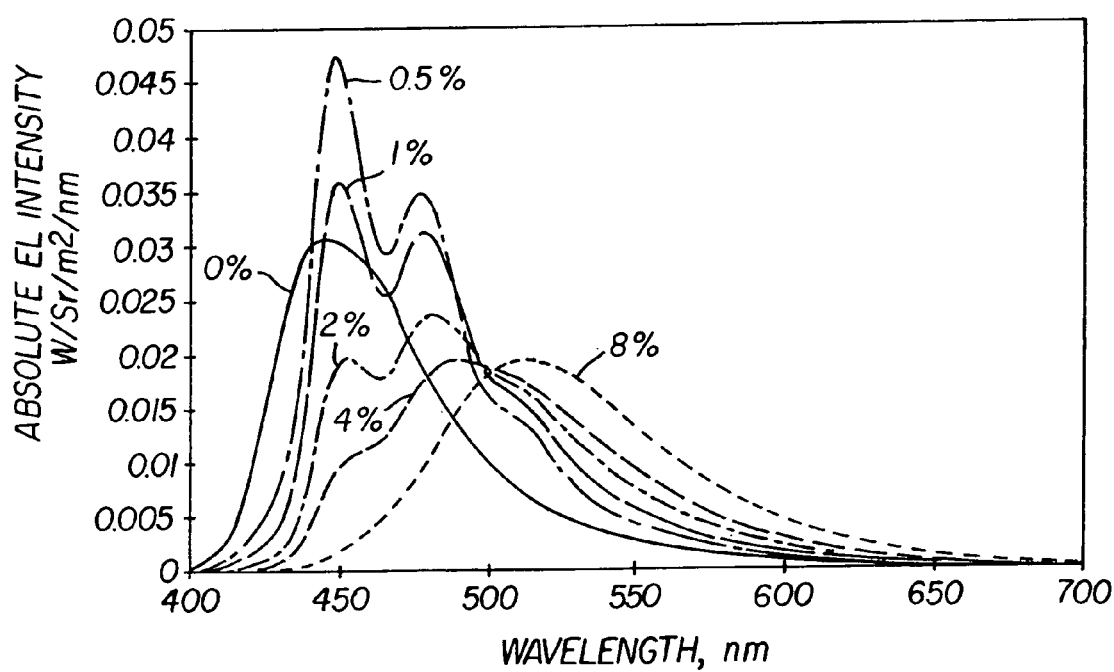
FIG. 5 shows electroluminescence spectra of an OLED device where the light emitting layer is composed of dibenzo[b,k]perylene and TBADN; current density is 20 mA/cm$^2$.

FIG. 5 shows the absolute EL spectra of an OLED device where the light emitting layer is composed of dibenzo[b,k]

perylene and TBADN. The EL spectra signal that formation of an aggregate state of dibenzo[b,k]perylene occurs in a nonpolar TBADN environment as well as in polar AlQ$_3$ environment. With increasing concentration of dibenzo[b,k] perylene the aggregate contribution to the overall EL drastically increases. Thus, the EL spectrum is composed primarily of the emission spectrum of dibenzo[b,k]perylene in its monomer state in the 0.5% case, while in the 8% case the emission is almost solely that of dibenzo[b,k]perylene in its aggregate state.

Figure 6:
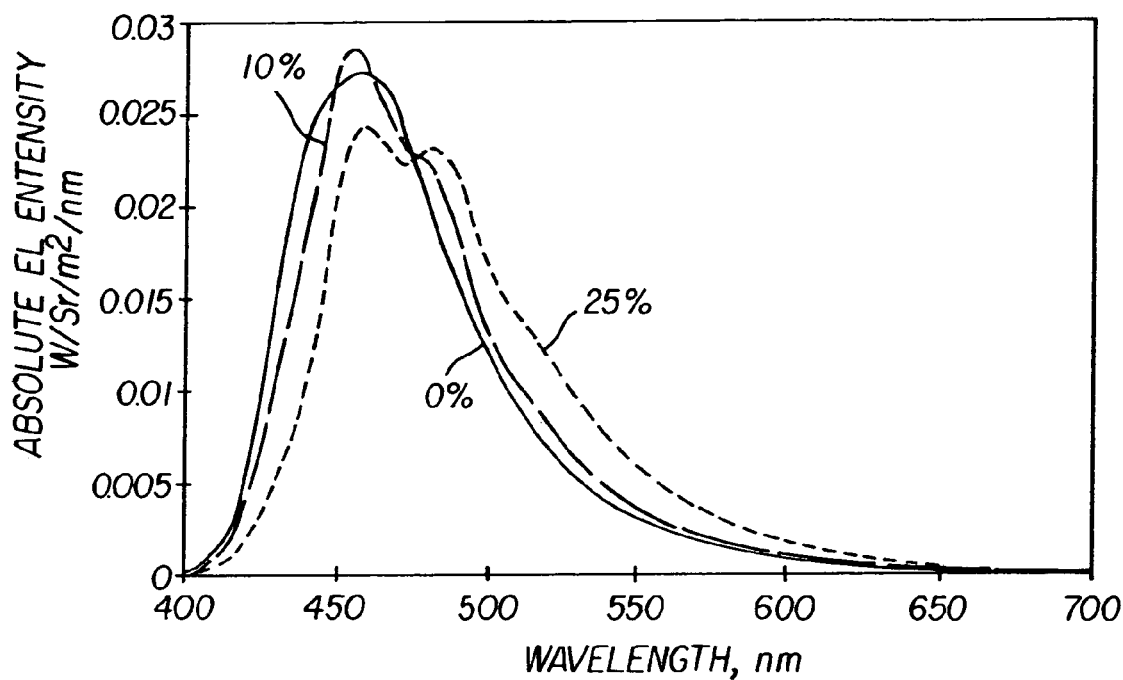
FIG. 6 shows electroluminescence spectra of an OLED device where the light emitting layer is composed of benzo[ghi]perylene and TBADN; current density is 20 mA/cm$^2$.

FIG. 6 shows the absolute EL spectra of an OLED device where the light emitting layer is composed of benzo[ghi] perylene and TBADN. The EL spectra signal that formation of an aggregate state of benzo[ghi]perylene occurs. With increasing concentration of benzo[ghi]perylene the aggregate contribution to the overall EL increases. The EL spectra are composed primarily of the emission spectrum of benzo[ghi]perylene in its aggregate state with some contribution of the monomer state emission and possibly little emission of TBADN.

Figure 7:
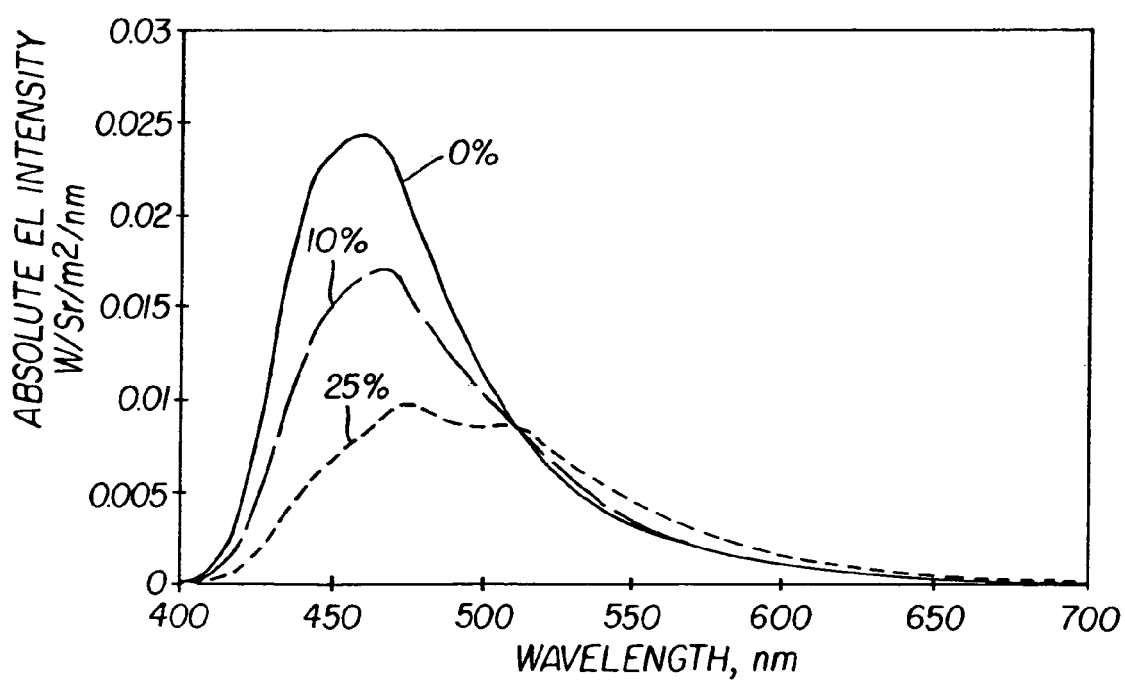
FIG. 7 shows electroluminescence spectra of an OLED device where the light emitting layer is composed of coronene and TBADN; current density is 20 mA/cm$^2$.

FIG. 7 shows the absolute EL spectra of an OLED device where the light emitting layer is composed of coronene and TBADN. The EL spectra signal that formation of an aggregate state of coronene occurs. With increasing concentration of coronene the aggregate contribution to the overall EL increases. The EL spectra are composed primarily of the emission spectrum of coronene in its aggregate state with some contribution of the emission of TBADN.

Figure 8:
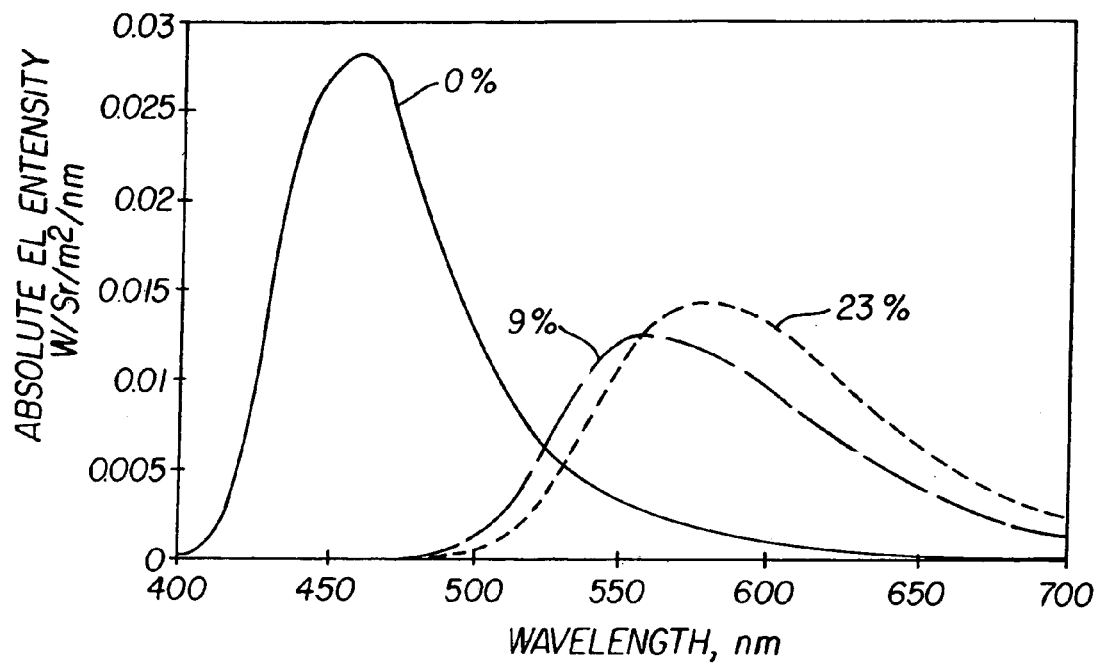
FIG. 8 shows electroluminescence spectra of an OLED device where the light emitting layer is composed of peropyrene (dibenzo[cd,lm]perylene) and TBADN; current density is 20 mA/cm$^2$.

FIG. 8 shows the absolute EL spectra of an OLED device where the light emitting layer is composed of peropyrene (dibenzo[cd,lm]perylene) and TBADN. The EL spectra signal that formation of an aggregate state of peropyrene occurs. With increasing concentration of peropyrene the aggregate contribution to the overall EL drastically increases. The EL spectra are composed primarily of the emission spectrum of peropyrene in its aggregate state.

Figure 9:
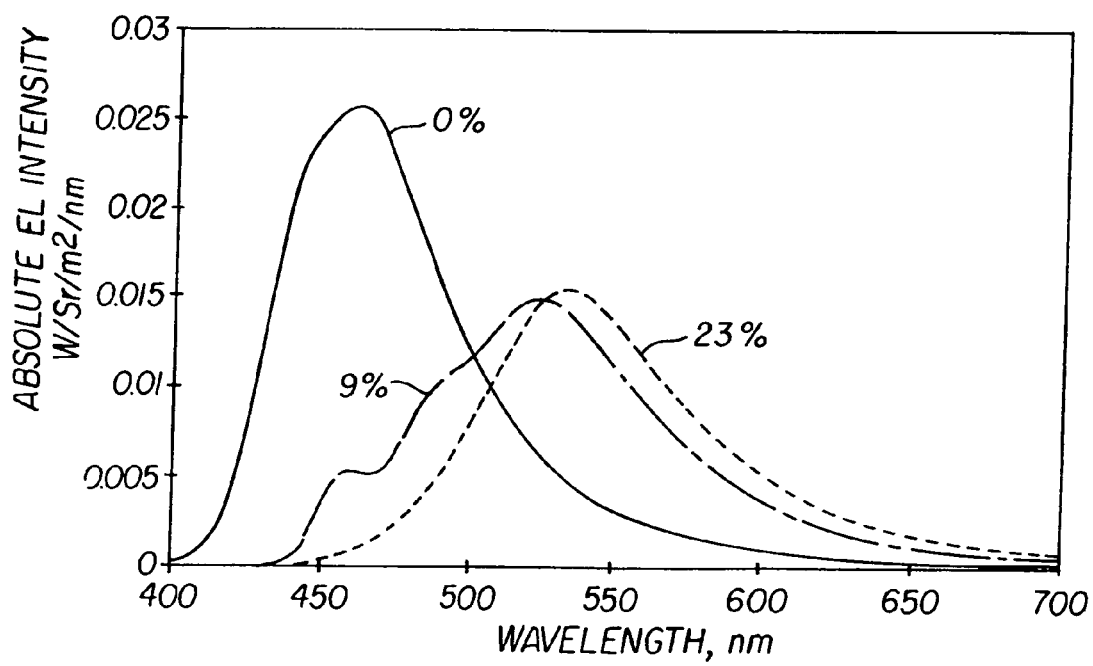
FIG. 9 shows electroluminescence spectra of an OLED device where the light emitting layer is composed of perylene and TBADN; current density is 20 mA/cm$^2$.

FIG. 9 shows the absolute EL spectra of an OLED device where the light emitting layer is composed of perylene and TBADN. The EL spectra signal that formation of an aggregate state of perylene occurs. With increasing concentration of perylene the aggregate contribution to the overall EL drastically increases. The EL spectra are composed primarily of the emission spectrum of perylene in its aggregate state.

According to the present invention, the luminescent layer (either layer 232 of FIG. 2 or layer 333 of FIG. 3) is primarily responsible for the electroluminescence emitted from the OLED device. One of the most commonly used formulations for this luminescent layer is an organic thin film including a host and one or more dopants. The host serves as the solid medium or matrix for the transport and recombination of charge carriers injected from the anode and the cathode. The dopant, usually homogeneously distributed in the host in small quantity, provides the emission centers where light is generated. Following the teaching of the prior art, the present invention uses a luminescent layer including a host and a dopant, but it distinguishes over the prior art that the host of the present invention is a mixture having at least two components, each component having specific electronic properties. The selection of these host components and compatible dopant materials is in accordance with the following criteria:

1. The host is a solid organic thin film comprising a mixture of at least two components;
2. The first component of the mixture is an organic compound that is capable of transporting either electrons or holes or both;
3. The first component of the mixture is capable of forming both monomer state and an aggregate state;
4. The first component of the mixture is capable of forming the aggregate state either in the ground electronic state or in the excited electronic state;
5. The first component of the mixture is capable of forming the aggregate state that results in a different absorption or emission spectrum or both relative to the absorption or emission spectrum or both of the monomer state, respectively (the aggregate state can emit or absorb or both to the red or to the blue of the emission or absorption spectrum or both of the monomer state, respectively);
6. The first component of the mixture is capable of forming the aggregate state whose presence results in a quantum yield of luminescence of the monomer state being different relative to the quantum yield of luminescence of the monomer state in the absence of the aggregate states (the quantum yield of luminescence for the monomer state can be either enhanced or reduced);
7. The first component of the mixture is an organic compound containing at least one perylene carbocyclic ring structure or at least one mono-aza-perylene or poly-aza-perylene ring structure;
8. The second component of the mixture is an organic compound that upon mixing with the first host component is capable of forming a continuous and substantially pin-hole-free layer; and
9. The dopant is an organic luminescent compound capable of accepting the energy released from the recombination of electrons and holes in either the first or second host components, and emitting the energy as light.

Following the selection criteria of this invention, OLED devices have been constructed having excellent operational stability. Importantly, for red devices the luminance efficiency measured in candelas per ampere significantly increases, compared to the system without the first component, and remains constant over a large range of brightness or current densities. In addition, the color chromaticity is greatly improved and the drive voltage is reduced. This is a distinct advantage over the prior art, where such operational stability improvements over comparative examples combined with such long lifetimes have never been demonstrated, the luminance efficiency often decreases, or otherwise varies, with increasing brightness or current density, color chromaticity is often compromised, and drive voltage often increases. Another important advantage is that the chromaticity also remains essentially constant, independent of the brightness or current density. Thus, the problem of color shift with brightness in an OLED device is also eliminated.

Preferred materials for the first host component of the luminescent layer of this invention include a class of compounds which, for the purpose of this invention, will be referred to as organic compounds containing at least one perylene carbocyclic ring structure or at least one mono-aza-perylene or poly-aza-perylene ring structure. The organic compounds containing at least one perylene ring structure comprise a large family of polycyclic hydrocarbons (PAH) and combinations of two or more PAH that contain at least one perylene ring structure in their structural formula. The organic compounds containing at least one mono-aza-perylene or poly-aza-perylene ring structure comprise a large family of N-atom containing heterocyclic hydrocarbons (aza-polycyclic hydrocarbons, a-PAH) and combinations of two or more a-PAH or at least one PAH and at least one a-PAH that contain at least one mono-aza-perylene or poly-aza-perylene ring structure in their structural formula. Essentially any not overly sterically crowded and more or less flat and rigid molecule, or one having sterically available flat and rigid part, that contains at least one perylene ring structure has a propensity to undergo aggregation and form an aggregate state and as such is included in the list of preferred materials for the first host component of the luminescent layer of this invention. Possible exceptions include compounds that undergo known unfavorable chemical reactions either thermally, photochemically, or upon electrochemical oxidation or reduction in an OLED device. For example, 1,3-diphenylisobenzofuran readily undergoes Diels-Alder reactions as well as rearrangement and condensation reactions; Aryl-CH$_2$-Aryl' bridges have labile hydrogen atoms; esters undergo dissociation and decarboxylation reactions, alcohols and acids undergo deprotonation, etc. Another example of an exception that depends on the nature of the use of the material in an OLED device can include certain heterocyclic molecules such as imidazoles, triazoles, oxadiazoles, pyridines, phenanthrolines, and others, which are known to undergo certain chemical transformations in an OLED device upon their electrochemical oxidation (hole injection) that leads to short operational lifetimes. Another example of possible exception includes molecules containing chloro-, bromo-, or iodo-substituents which, upon electrochemical oxidation or reduction, undergo possible cleavage or dissociation reactions that lead to short operational stabilities of an OLED device. PAH compounds containing at least one perylene ring structure and a-PAH compounds containing at least one mono-aza-perylene or poly-aza-perylene ring structure and absorbing light in the UV, near UV, and visible region up to 450 nm are preferred materials for the first host component of a blue-emitting OLED device and blue layer of a white-emitting OLED device. PAH compounds containing at least one perylene ring structure and a-PAH compounds containing at least one mono-aza-perylene or poly-aza-perylene ring structure and absorbing light in the UV, near UV, and visible region up to 490 nm are preferred materials for the first host component of a blue-green-emitting OLED device and blue-green layer of a white-emitting OLED device. PAH compounds containing at least one perylene ring structure and a-PAH compounds containing at least one mono-aza-perylene or poly-aza-perylene ring structure and absorbing light in the UV, near UV, and visible region up to 520 nm are preferred materials for the first host component of a green-emitting OLED device and green layer of a white-emitting OLED device. PAH compounds containing at least one perylene ring structure and a-PAH compounds containing at least one mono-aza-perylene or poly-aza-perylene ring structure and absorbing light in the UV, near UV, and visible region up to 580 nm are preferred materials for the first host component of a yellow-orange-emitting OLED device and yellow-orange layer of a white-emitting OLED device. PAH compounds containing at least one perylene ring structure and a-PAH compounds containing at least one mono-aza-perylene or poly-aza-perylene ring structure and absorbing light in the UV, near UV, and visible region up to 630 nm are preferred materials for the first host component of a red-emitting OLED device and red layer of a white-emitting OLED device.

Unless otherwise specifically stated, use of the term "substituted" or "substituent" means any group or atom other than hydrogen. Unless otherwise provided, when a group (including a compound or complex) containing a substitutable hydrogen is referred to, it is also intended to encompass not only the unsubstituted form, but also form further substituted with any substituent group or groups as herein mentioned, so long as the substituent does not destroy properties necessary for utility. Suitably, a substituent group can be fluorine or can be bonded to the remainder of the molecule by an atom of carbon, silicon, oxygen, nitrogen, phosphorous, sulfur, selenium, or boron. The substituent can be, for example, fluoro; nitro; hydroxyl; cyano; carboxyl; or groups which can be further substituted, such as alkyl, including straight or branched chain or cyclic alkyl, such as methyl, trifluoromethyl, ethyl, t-butyl, 3-(2,4-di-t-pentylphenoxy)propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyi, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which can be substituted and which contain a 3 to 7 membered heterocyclic ring composed of carbon atoms and at least one hetero atom selected from the group including of oxygen, nitrogen, sulfur, phosphorous, or boron. such as 2-furyl, 2-thienyl, 2-benzimidazolyloxy or 2-benzothiazolyl; quaternary ammonium, such as triethylammonium; quaternary phosphonium, such as triphenylphosphonium; and silyloxy, such as trimethylsilyloxy.

If desired, the substituents can themselves be further substituted one or more times with the described substituent groups. The particular substituents used can be selected by those skilled in the art to attain the desired desirable properties for a specific application and can include, for example, electron-withdrawing groups, electron-donating groups, and steric groups.

The list of PAH and a-PAH useful as building blocks and parent structures for compounds containing at least one perylene ring structure or at least one mono-aza-perylene or poly-aza-perylene ring structure or substituted derivatives thereof includes:

1. Perylene
2. Benzo[a]perylene
3. Benzo[b]perylene
4. Benzo[ghi]perylene
5. Dibenzo[b,k]perylene
6. Dibenzo[b,pqr]perylene
7. Dibenzo[b,ghi]perylene
8. Dibenzo[a,ghi]perylene
9. Phenanthro[2,1,10,9,8,7-pqrstuv]pentaphene (Tribenzo[cd,ghi,lm]perylene)
10. Dibenzo[bc,kl]coronene
11. Tribenzo[a,ef,no]coronene
12. Benzo[qr]naphtho[2,1,8,7-fghi]pentacene (Tribenzo[b,ghi,k]perylene)
13. Tribenzo[b,n,pqr]perylene
14. Tribenzo[b,e,ghi]perylene
15. Tribenzo[a,e,ghi]perylene
16. Tribenzo[a,ghi,k]perylene
17. Tribenzo[a,ghi,o]perylene
18. Ovalene
19. Dibenzo[fg,ij]pentaphene (Dibenzo[b,n]perylene)
20. Dibenzo[b,e]perylene
21. Coronene
22. Benzo[a]coronene
23. Naphtho[2,3-a]coronene
24. Aceperylene
25. Bisanthrene (bisanthene)
26. Peropyrene (dibenzo[cd,lm]perylene)
27. Dibenzo[a,j]coronene
28. Naphtho[1,2-b]perylene
29. Dibenzo[de,st]pentacene (Naphtho[2',3':2,3]perylene)
30. Naphtho[2,1-b]perylene
31. Tetrabenzo[a,f,j,o]perylene
32. Tetrabenzo[bc,efkl,no]coronene
33. Tetrabenzo[a,fk,n]perylene
34. Pyreno[1,10,9-abc]coronene
35. Naphtho[8,1,2-bcd]perylene
36. Dibenzo[a,j]perylene
37. Tetrabenzo[bc,ef,hi,kl]coronene
38. Anthra[2,3-a]coronene
39. Tribenzo[fgh,pqr,za1b1]trinaphthylene
40. Tribenzo[b,ghi,n]perylene
41. Dibenzo[a,g]coronene
42. Hexabenzo[a,d,g,j,m,p]coronene
43. Dibenzo[bc,ef]coronene
44. Naphtho[8,1,2-abc]coronene
45. Perylo[3,2,1,12-pqrab]perylene
46. Hexabenzo[bc,efhi,kl,no,qr]coronene (hexa-peri-benzocoronene)
47. Dibenzo[ij,rst]phenanthro[9,10,1,2-defg]pentaphene
48. Phenaleno[1,2,3-de]quinoline (3-Azaperylene)
49. Benzo[1,2,3-de:4,5,6-d'e']diquinoline (3,9-Diazaperylene)
50. Phenanthro[3,4,5,6-jklmn]thebenidine (aza-coronene)
51. Phenanthridino[2,1,10,9-jklmn]thebenidine (diaza-coronene)
52. Benzo[b]phenanthro[3,4,5,6-jklmn]thebenidine (aza-benzo[a]coronene)
53. Phenaleno[1,2,3-kl]acridine
54. 3,11-Dimethyl-benzo[1,2,3-kl:4,5,6-k'l']diacridine
55. Benzo[1,2,3-kl:4,5,6-k'l']diacridine
56. Pyreno[9,10,1-def:4,5,6-d'e'f']diisoquinoline
57. Phenaleno[1,2,3-de]isoquinoline
58. Benzo[1,2,3-de:4,5,6-d'e']diisoquinoline When a molecule can have two or more substituents, the substituents can be joined together to form a ring such as a fused ring unless otherwise provided. Generally, the previously described groups and substituents thereof can include those having up to 48 carbon atoms, typically 1 to 36 carbon atoms and usually less than 24 carbon atoms, but greater numbers are possible depending on the particular substituents selected.

Examples of fused ring subtituents includes but is not limited to: ace, indeno, 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP,

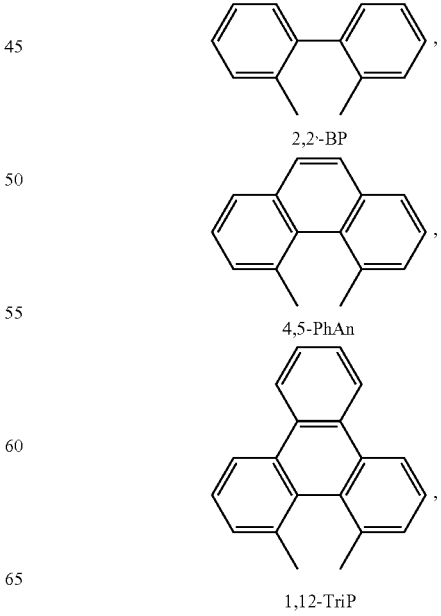

2,2'-BP 4,5-PhAn 1,12-TriP

-continued
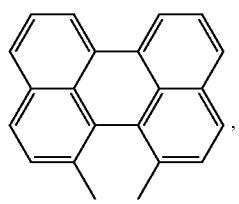
1,12-Per
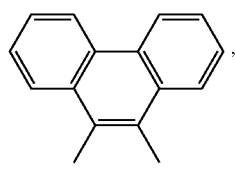
9,10-PhAn
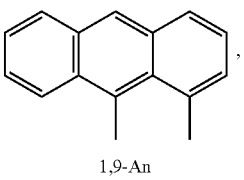
1,9-An
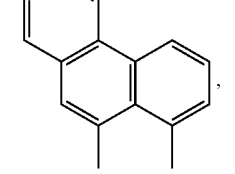
1,10-PhAn
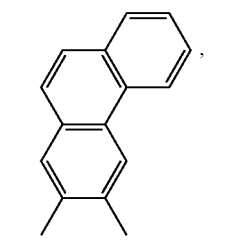
2,3-PhAn
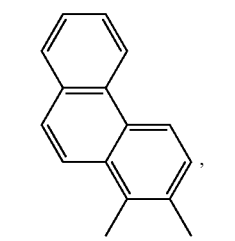
1,2-PhAn
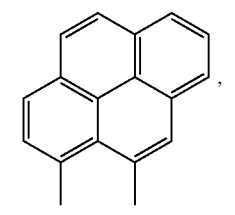
1,10-Pyr
-continued
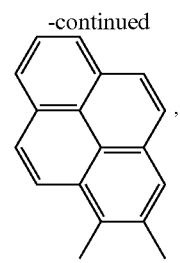
1,2-Pyr
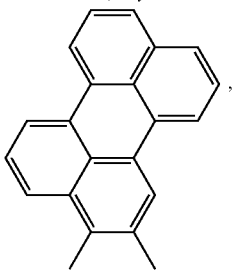
2,3-Per
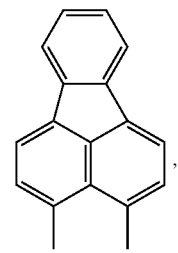
3,4-FlAn
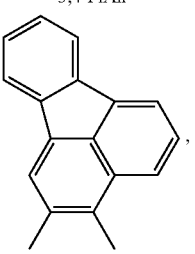
2,3-FlAn
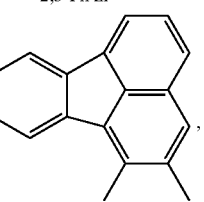
1,2-FlAn
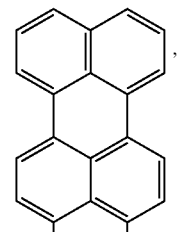
3,4-Per

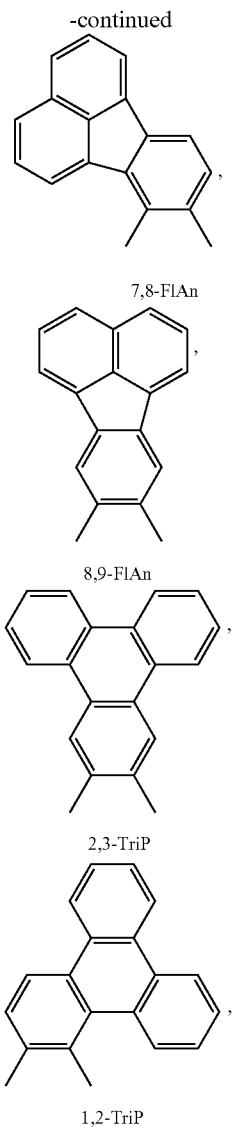

7,8-FlAn 8,9-FlAn 2,3-TriP 1,2-TriP (where bonds that do not form a cycle indicate points of attachment) derivatives.

Further examples of preferred materials for the first host component of the luminescent layer of this invention includes substituted or unsubstituted derivatives of:
59. Perylene
60. Benzo[a]perylene
61. Benzo[b]perylene
62. Benzo[ghi]perylene
63. Dibenzo[b,k]perylene
64. Dibenzo[b,pqr]perylene
65. Dibenzo[b,ghi]perylene
66. Dibenzo[a,ghi]perylene
67. Phenanthro[2,1,10,9,8,7-pqrstuv]pentaphene (Tribenzo[cd,ghi,lm]perylene)
68. Dibenzo[bc,kl]coronene
69. Tribenzo[a,ef,no]coronene
70. Naphtho[3,2,1,8,7-defgh]pyranthrene
71. Benzo[qr]naphtho[2,1,8,7-fghi]pentacene (Tribenzo[b,ghi,k]perylene)
72. Tribenzo[b,n,pqr]perylene
73. Tribenzo[b,e,ghi]perylene
74. Tribenzo[a,e,ghi]perylene
75. Tribenzo[a,ghi,k]perylene
76. Tribenzo[a,ghi,o]perylene
77. Ovalene
78. Dibenzo[fg,ij]pentaphene (Dibenzo[b,n]perylene)
79. Dibenzo[b,e]perylene
80. Coronene
81. Aceperylene
82. Bisanthrene (bisanthene)
83. Peropyrene (dibenzo[cd,lm]perylene)
84. Benzo[fg]naphtho[1,2,3-qr]pentacene
85. Tetrabenzo[a,d,j,m]coronene
86. Benzo[st]naphtho[2,1,8,7-defg]pentacene
87. Benzo[uv]naphtho[2,1,8,7-defg]pentacene (1,12-Benzo[naphtho-2",3":4,5-perylene])
88. Benzo[uv]naphtho[2,1,8,7-defg]pentaphene
89. Benzo[uv]naphtho[2,1,8,7-fghi]hexacene
90. Benzo[a]naphtho[2,3-j]coronene
91. Dibenzo[a,j]coronene
92. Benzo[pqr]naphtho[1,2-b]perylene
93. Benzo[pqr]naphtho[2,1-b]perylene
94. Benzo[ghi]naphtho[2,1-b]perylene
95. Benzo[ghi]naphtho[1,2-b]perylene
96. Naphtho[1,2-b]perylene
97. Dibenzo[de,st]pentacene (Naphtho[2',3':2,3]perylene)
98. Naphtho[2,1-b]perylene
99. Dinaphtho[3,2,1-fg:3',2',1'-qr]pentacene
100. Tetrabenzo[a,fj,o]perylene
101. Tetrabenzo[bc,ef,kl,no]coronene
102. Benzo[fg]benzo[8,9]phenaleno[1,2,3,4,5-rstuv]pentaphene
103. Anthra[1,2,3-uv]benzo[fg]pentaphene
104. Tetrabenzo[a,f,k,n]perylene
105. Dinaphtho[3,2,1-fg:1',2',3'-ij]pentaphene
106. Benzo[e]phenanthro[1,10,9,8-opqra]perylene
107. Dibenzo[kl,rst]naphtho[2,1,8,7-defg]pentaphene
108. Benzo[pqr]dinaphtho[8,1,2-bcd:2',1',8'-lmn]perylene
109. Pyreno[1,10,9-abc]coronene
110. Naphtho[8,1,2-bcd]perylene
111. Benzo[qr]naphtho[2,1,8,7-defg]pentacene
112. Anthra[2,1,9,8,7-defghi]benzo[qr]pentacene
113. Benzo[j]naphtho[8,1,2-abc]coronene
114. Benzo[de]naphtho[2,1,8,7-qrst]pentacene
115. Tribenzo[de,ij,rst]pentaphene
116. Benzo[a]naphtho[2,1,8-cde]perylene
117. Benzo[ij]naphtho[2,1,8,7-defg]pentaphene
118. Benzo[a]naphtho[2,1,8-lmn]perylene
119. Dinaphtho[2,1,8,7-defg:2',1',8',7'-opqr]pentacene-(1,14,7,8-Dibenzoperopyrene; 2,3,3',2'-Dipyrenylene; Dinaphtho[8,1,2-bcd:8',1',2'-klm]perylene)
120. Dinaphtho[2,1,8,7-defg:2',1',8',7'-ijkl]pentaphene-(1,14:10,11-Dibenzoperopyrene; 2,4:9,11-Dinaphthoperylene)
121. Anthra[2,1,9,8,7-defghi]benzo[op]pentacene
122. Dinaphtho[1,8-ab:8',1',2',3'-fghi]perylene
123. Dibenzo[ghi,lm]naphtho[1,8-ab]perylene
124. Tetrabenzo[de,hi,op,st]pentacene (1,9:5,10-Di(peri-naphthylene)anthracene)
125. Benzo[lm]naphtho[1,8-ab]perylene
126. Benzo[lm]phenanthro[5,4,3-abcd]perylene
127. Dibenzo[a,j]perylene
128. Tetrabenzo[fg,ij,pq,uv]pentaphene
129. Tetrabenzo[bc,ef,hi,kl]coronene
130. Dibenz[bc,uv]ovalene
131. Benzo[bc]naphth[2,1,8,7-stuv]ovalene 132. Pentapheno[2,1,14,13,12,11-defghijkl]pyreno[2,1,10,9,8,7-pqrstuv]pentaphene (Circumpyrene)
133. Anthra[2,3-a]coronene
134. Phenanthro[2,3-a]coronene
135. Tetrabenzo[b,fgh,pqr,za1b1]trinaphthylene
136. Tribenzo[fgh,pqr,za1b1]trinaphthylene
137. Dibenzo[pqr,za1b1]naphtho[7,8,1,2,3-defgh]trinaphthylene
138. Diphenanthro[3,4,5,6-efghi:3',4',5',6'-uvabc]ovalene
139. Dibenzo[cd,n]naphtho[3,2,1,8-pqra]perylene
140. Dibenzo[de,ij]naphtho[7,8,1,2,3-pqrst]pentaphene
141. Benzo[qr]phenanthro[2,1,10,9-fghi]pentacene
142. Tribenzo[b,ghi,n]perylene
143. Dibenzo[a,g]coronene
144. Hexabenzo[a,d,gj,m,p]coronene
145. Benzo[cd]naphtho[3,2,1,8-pqra]perylene
146. Dibenzo[bc,ef]coronene
147. Phenanthro[5,4,3,2-abcde]perylene
148. Benzo[pqr]naphtho[8,1,2-bcd]perylene
149. Naphtho[8,1,2-abc]coronene
150. Dinaphtho[8,1,2-abc:8',1',2'-jkl]coronene
151. Benzo[lmn]naphtho[2,1,8-qra]perylene
152. Dibenzo[ghi,n]naphtho[8,1,2-bcd]perylene
153. Dibenzo[a,ghi]naphtho[2,1,8-lmn]perylene
154. Dibenzo[de,ij]phenanthro[2,1,10,9,8,7-pqrstuv]pentaphene
155. Benz[4,10]anthra[1,9,8-abcd]coronene
156. Perylo[3,2,1,12-pqrab]perylene
157. Dibenzo[de,ij]naphtho[3,2,1,8,7-rstuv]pentaphene
158. Dibenzo[de,ij]naphtho[7,8,1,2,3-pqrst]pentaphene
159. Benzo[a]coronene
160. Naphtho[2,3-a]coronene
161. Benzo[ghi]naphtho[cde]perylene
162. Naphtho[8,1,2-bcd]perylene
163. Terrylene
164. Anthra[1,9,8-abcd]benzo[hi]coronene
165. Anthra[2,3-a]coronene
166. Anthra[3,2,1,9-pqra]benzo[cd]perylene
167. Anthra[9,1,2-abc]coronene
168. Anthra[9,1,2-bcd]perylene
169. Anthrodianthrene
170. Benz[4,10]anthra[1,9,8-abcd]coronene
171. Benz[a]ovalene
172. Benz[d]ovalene
173. 1.14-Benzobisanthene
174. 1.14-Benzodinaphtho[1".7",2,4],[7"'.1"',11.13]bisanthene
175. Benzo[3,4]phenanthro[2,1,10,9,8,7-pqrstuv]pentaphene
176. Benzo[a]coronene
177. Benzo[a]naphtho[1,2,3,4-ghi]perylene
178. Benzo[a]naphtho[2,1,8-cde]perylene
179. Benzo[a]naphtho[2,1,8-lmn]perylene
180. Benzo[a]naphtho[8,1,2-klm]perylene
181. Benzo[b]naphtho[1,2,3,4-pqr]perylene
182. Benzo[bc]naphtho[1,2,3-ef]coronene
183. Benzo[bc]naphtho[3,2,1-ef]coronene
184. Benzo[cd]naphtho[3,2,1,8-pqra]perylene
185. Benzo[e]phenanthro[1,10,9,8-opqra]perylene
186. Benzo[e]phenanthro[2,3,4,5-pqrab]perylene
187. Benzo[ef]phenaleno[9,1,2-abc]coronene
188. Benzo[g]naphtho[8,1,2-abc]coronene
189. Benzo[ghi]cyclopenta[cd]perylene
190. 1H-Benzo[ghi]cyclopenta[pqr]perylene
191. Benzo[ghi]naphtho[1,2-b]perylene
192. Benzo[ghi]naphtho[2,1-a]perylene
193. Benzo[ghi]naphtho[2,1-b]perylene
194. Benzo[ghi]naphth[2',1',8',7':5,6,7]aceanthryleno[10,1,2-abcd]perylene (Circumanthracene)
195. Benzoo]naphtho[8,1,2-abc]coronene
196. Benzo[lm]naphtho[1,8-ab]perylene
197. Benzo[lm]phenanthro[5,4,3-abcd]perylene
198. Benzo[lmn]naphtho[2,1,8-qra]perylene
199. Benzo[m]diphenanthro[1,10,9-abc:1',10',9'-ghi]coronene
200. Benzo[m]naphtho[8,1,2-abc]coronene
201. Benzo[p]naphtho[8,1,2-abc]coronene
202. Benzo[pqr]dinaphtho[8,1,2-bcd:2',1',8'-lmn]perylene
203. Benzo[pqr]naphtho[1,2-b]perylene
204. Benzo[pqr]naphtho[2,1-b]perylene
205. Benzo[pqr]naphtho[8,1,2-bcd]perylene
206. Benzo[qrs]naphtho[3,2,1,8,7-defgh]pyranthrene
207. o-meso-Benzodianthrene
208. p-meso-Benzodianthrene
209. 1,12-Benzoperylene
210. 1,2-Benzoperylene
211. 2,3-Benzoperylene
212. 1,2-Benzperylene
213. 1,1'-Bicoronene
214. Ceranthrene
215. homeo-Cerodianthrene
216. Cyclopenta[1,2-a:3,4,5-b'c']dicoronene
217. Cyclopenta[cd]perylene
218. 11H-Cyclopenta[ghi]perylene
219. Dibenz[e,ghi]indeno[1,2,3,4-pqra]perylene
220. 3.4,11,12-Dibenzobisanthene
221. Dibenzo[a,cd]naphtho[8,1,2,3-fgbi]perylene
222. Dibenzo[a,d]coronene
223. Dibenzo[a,f]perylene
224. Dibenzo[a,g]coronene
225. Dibenzo[a,ghi]naphtho[2,1,8-cde]perylene
226. Dibenzo[a,ghi]naphtho[2,1,8-lmn]perylene
227. Dibenzo[a,ghi]naphtho[8,1,2-klm]perylene
228. Dibenzo[a,ghi]perylene
229. Dibenzo[a,j]coronene
230. Dibenzo[a,j]difluoreno[2,1,9-cde:2',1',9'-lmn]perylene
231. Dibenzo[aj]perylene
232. Dibenzo[a,jk]phenanthro[8,9,10,1,2-cdefgh]pyranthrene
233. Dibenzo[a,n]perylene
234. Dibenzo[a,o]perylene
235. Dibenzo[b,ghi]perylene
236. Dibenzo[b,k]perylene
237. Dibenzo[b,n]perylene
238. Dibenzo[b,pqr]perylene
239. Dibenzo[bc,ef]coronene
240. Dibenzo[bc,kl]coronene
241. Dibenzo[cd,k]naphtho[3,2,1,8-pqra]perylene
242. Dibenzo[cd,lm]perylene
243. Dibenzo[cd,n]naphtho[3,2,1,8-pqra]perylene
244. Dibenzo[e,ghi]perylene
245. Dibenzo[efhi]naphtho[8,1,2-abc]coronene
246. Dibenzo[efno]naphtho[8,1,2-abc]coronene
247. Dibenzo[fg,ij]phenanthro[2,1,10,9,8,7-pqrstuv]pentaphene
248. Dibenzo[fg,ij]phenanthro[9,10,1,2,3-pqrst]pentaphene
249. Dibenzo[fg,ij]triphenyleno[1,2,3,4-rst]pentaphene
250. Dibenzo[ghi,lm]naphtho[1,8-ab]perylene
251. Dibenzo[ghi,n]naphtho[8,1,2-bcd]perylene
252. Dibenzo[ghi,pqr]perylene
253. Dibenzo[b,n]perylene
254. Dibenzo[hi,kl]naphtho[8,1,2-abc]coronene
255. Dibenzo[hi,op]dinaphtho[8,1,2-cde:2',1',8'-uva]pentacene 256. Dibenzo[h,s]peropyrene
257. Dibenzo[ij,rst]phenanthro[9,10,1,2-defg]pentaphene
258. Dibenzo[ijk,tuv]peropyrene
259. Dibenzo[j,lm]naphtho[1,8-ab]perylene
260. Dibenzo[j,lm]phenanthro[5,4,3-abcd]perylene
261. Dibenzo[kl,no]naphtho[8,1,2-abc]coronene
262. Dibenzo[kl,rst]naphtho[2,1,8,7-defg]pentaphene
263. Dibenzo[j,lm]naphtho[ab]perylene
264. Dibenzo[o,rst]dinaphtho[2,1-a:8', 1',2'-cde]pentaphene
265. Dibenzo[uv,a1b1]benzo[5,6]naphthaceno[2,1,12,11,10,9-fghijklm]heptacene
266. 2,3,10,11-Dibenzoperylene
267. 2,3,8,9-Dibenzoperylene
268. 1.12,2.3-Dibenzoperylene
269. 1.12,4.5-Dibenzoperylene
270. Dicyclopenta[aj]coronene
271. Di-fluorantheno[3.5,4.6],[4".6",9.11]coronene
272. Dinaphtho[1,2-b:2',1'-n]perylene
273. Dinaphtho[1,2,3-cd,1',2',3'-lm]perylene
274. Dinaphtho[1,2,3-cd,3',2',1'-lm]perylene
275. Dinaphtho[1,2-b,2',1'-n]perylene
276. Dinaphtho[1,8-ab:8',1',2',3'-fghi]perylene
277. Dinaphtho[2,1-a:2',1'-j]perylene
278. Dinaphtho[2,1,8-cde,2',1',8'-lmn]perylene
279. Dinaphtho[2,1,8-fgh:3',2',1',8',7'-rstuv]pentaphene
280. Dinaphtho[2,1,8-fgh:7',8',1',2',3'-pqrst]pentaphene
281. Dinaphtho[2,1,8,7-hijk:2',1',8',7'-wxyz]heptacene
282. Dinaphtho[8,1,2-abc:2',1',8'-efg]coronene
283. Dinaphtho[8,1,2-abc:2',1',8'-hij]coronene
284. Dinaphtho[8,1,2-abc:2',1',8'-klm]coronene
285. Dinaphtho[8,1,2-abc:2',1',8'-nop]coronene
286. Dinaphtho[8,1,2-abc:8',1',2'-ghi]coronene
287. Dinaphtho[8,1,2-abc:8',1',2'-jkl]coronene
288. Diphenanthro[5,4,3-abcd:5',4',3'-jklm]perylene
289. 2,9-Diphenylcoronene
290. Dipyreno[1'.3',4.6],[10".2",9.11]coronene
291. 2,3,3',2'-Dipyrenylene
292. 1.12,2.3,4.5,6.7,8.9,10.11-Hexabenzocoronene
293. Indeno[1,2,3-cd]perylene
294. Naphth[2,1,8-uva]ovalene
295. Naphth[2',1',8',7':4,10,5]anthra[1,9,8-azbcd]coronene (Circobiphenyl)
296. Naphthaceno[2,1,12,11-opqra]naphthacene
297. Naphthaceno[4,5,6,7,8-defghij]naphthacene
298. peri-Naphthacenonaphthacene
299. Naphtho[1,2,3,4-ghi]perylene
300. 9H-Naphtho[1,2,3-cd]perylene
301. Naphtho[1,2-a]coronene
302. Naphtho[1,2-b]perylene
303. Naphtho[2,1-a]perylene
304. Naphtho[2,1-b]perylene
305. Naphtho[2,1-b]picene
306. Naphtho[2,1-c:7,8-c']diphenanthrene
307. Naphtho[2,3-a]coronene
308. Naphtho[2'.8',2.4]coronene
309. Naphtho[8,1,2-abc]coronene
310. Ovalene
311. Periflanthene
312. Perinaphthene
313. 2,3-Peri-naphthylene-pyrene
314. Perylo[3,2,1,12-pqrab]perylene
315. Phenanthro[1,10,9-abc]coronene
316. Phenanthro[1,10,9,8-opqra]perylene
317. Phenanthro[1,2,3,4-ghi]perylene
318. Phenanthro[10,1,2-abc]coronene
319. Phenanthro[2,1,10,9,8,7-pqrstuv]pentaphene
320. Phenanthro[3,4,5,6-bcdef]ovalene
321. Phenanthro[5,4,3,2-abcde]perylene
322. 7-Phenylbenzo[a]coronene
323. Pyreno[1,10,9-abc]coronene
324. Pyreno[10,1,2-abc]coronene
325. Pyreno[2,1-b]picene
326. Pyreno[5,4,3,2,1-pqrst]pentaphene
327. Tetrabenzo[a,c,hi,mn]naphthacene
328. Tetrabenzo[a,c,hi,qr]pentacene
329. Tetrabenzo[a,cj,l]naphthacene
330. Tetrabenzo[a,c,l,n]pentacene
331. Tetrabenzo[a,cd,f,lm]perylene
332. Tetrabenzo[a,cdj,lm]perylene
333. Tetrabenzo[a,e,j,o]peerylene
334. Tetrabenzo[a,f,j,o]perylene
335. Tetrabenzo[a,f,k,n]perylene
336. Tetrabenzo[bc,ef,hi,kl]coronene
337. Tetrabenzo[bc,ef,kl,no]coronene
338. Tetrabenzo[de,h,kl,rst]pentaphene
339. Tetrabenzo[de,hi,mn,qr]naphthacene
340. Tetrabenzo[de,hi,op,st]pentacene
341. Tetrabenzo[de,jk,op,uv]pentacene
342. Tetrabenzo[de,lm,uv,a1b1]heptacene
343. tetrabenzo[de,lm,st,c1d1]heptacene
344. Tetrabenzo[fg,ij,pq,uv]pentaphene
345. Tetrabenzo[a,c,hi,qr]pentacene
346. Tetrabenzo[gh,jk,tu,wx]pyranthrene
347. N,N,N',N'-Tetraphenyl-tetrabenzo[a,cdj,lm]perylene-1,10-diamine
348. Tribenzo[a,cd,lm]perylene
349. Tribenzo[a,e,ghi]perylene
350. Tribenzo[a,ef,hi]coronene
351. Tribenzo[a,ef,no]coronene
352. Tribenzo[a,fj]perylene
353. Tribenzo[a,ghi,k]perylene
354. Tribenzo[a,hi,kl]coronene
355. Tribenzo[a,jk,v]phenanthro[8,9,10,1,2-cdefgh]pyranthrene
356. Tribenzo[b,e,ghi]perylene
357. Tribenzo[b,n,pqr]perylene
358. Tribenzo[fg,ij,o]benzo[5,6]naphthaceno[10,11,12,1,2,3-qrstuvwx]hexaphene
359. Tribenzo[fg,q,vwx]benzo[5,6]naphthaceno[2,1,12,11,10-ijklmno]hexaphene
360. Tribenzo[jk,qr,uv]naphtho[2,1,8,7-defg]pentacene
361. Phenaleno[1,2,3-de]quinoline (3-Azaperylene)
362. Benzo[1,2,3-de:4,5,6-d'e']diquinoline (3,9-Diazaperylene)
363. Dinaphtho[1',2':2,3;2",1":10,1]perylo[1,12]furan
364. Diphenaleno[9',1',2':3,4,5:9",1",2":9,10,1]coroneno[1,2-c:7,8-c']difuran
365. Phenanthro[3,4,5,6-jklmn]thebenidine (aza-coronene)
366. Phenanthridino[2,1,10,9-jklmn]thebenidine (diaza--coronene)
367. Benzo[b]phenanthro[3,4,5,6-jklmn]thebenidine (aza--benzo[a]coronene)
368. 11aH-Benzo[fg]naphth[2',1',8',7':4,10,5]anthra[1,9,8-ijkl]thebenidine
369. 11aH-Pyreno[1',10',9',8':9,10,11,12]chryseno[6,5,4-defg]quinoline
370. Benzo[3",4"]chryseno[1",2":4',5']thieno[2',3':7,8]phenaleno[1,2,3-de]quinoline
371. Phenaleno[1,2,3-kl]acridine
372. 3,11-Dimethyl-benzo[1,2,3-kl:4,5,6-k'l']diacridine
373. 2,8-Di-4-morpholinyl-benzo[1,2,3-de:4,5,6-d'e']diquinoline-1,7-dicarbonitrile
374. Benzo[fg]benzo[6,7]phenanthridino[2,1,10,9-jklmn]thebenidine 375. Diphenaleno[1,2,3-ij:1',2',3'-i' j']anthra[1,9,8-cdef:4,10,5-c'd'e'f]di[2,7]naphthyridine
376. Benzo[1,2,3-kl:4,5,6-k'l']diacridine
377. Dibenzo[3,4:5,6]pyreno[2,1,10-def:7,8,9-d'e'f]diisoquinoline
378. Pyreno[9,10,1-def:4,5,6-d'e'f]diisoquinoline
379. Diphenanthro[3,4,5-mnab:5',4',3'-hijk]thebenidine
380. Benzo[b]pyrido[4',3',2':4,10]anthra[9,1-hi]thebenidine
381. Benzo[b]pyrido[4',3',2':4,10]anthra[1,9-hi]thebenidine
382. Phenaleno[1,2,3-de]isoquinoline
383. Benzo[lmn][3,8]phenanthrolino[2,1,10,9-defgh][3,8]phenanthroline
384. Benzo[1,2,3-de:4,5,6-d'e']diisoquinoline
385. Benzo[b]naphth[1',2',3':1,8]isoquino[5,4-hi]thebenidine Any of the above listed PAH and a-PAH containing at least one perylene ring structure or at least one mono-aza-perylene or poly-aza-perylene ring structure, and any compounds formed by the combination of one or more of the above listed PAH and a-PAH, which may or may not be chemically linked, are useful as the first host component, and importantly, the compounds do not have to be film forming materials at poop temperature. The mixture of the second host component and the first host component must be capable of forming continuous amorphous films.

In PAH and a-PAH compounds, containing at least one perylene ring structure or at least one mono-aza-perylene or poly-aza-perylene ring structure, which are formed by combination of at least two PAH, or at least two a-PAH, or at least one PAH and at least one a-PAH, the constituent PAH and a-PAH may or may not be not chemically connected together via a single chemical bond or linked via a saturated or unsaturated hydrocarbon group including alkenyl, alkynyl, PAH, a-PAH, and heterocycle or by a heteroatom N, O, or S. Examples of useful compounds formed by chemically connected combination of two or more the same or different PAH (aforementioned PAH 1 through 47), or two or more the same or different a-PAH (aforementioned a-PAH 48 through 58), or at least one PAH and at least one a-PAH include substituted or unsubstituted derivatives of:

386. Pyrene-coronene
387. Pyrene-benzene-perylene
388. Perylene-benzene-perylene
389. Perylene-perylene
390. Pyrene-perylene
391. Benzo[a]pyrene-perylene
392. Coronene-perylene
393. Benzo[ghi]perylene-pyrene
394. Naphthopyrene-coronene
395. Perylene-naphthacene
396. Naphthacene-dibenzo[b,k]perylene
397. Dibenzo[b,k]perylene-perylene
398. Fluoranthene-dibenzo[b,k]perylene
399. Fluoranthene-perylene
400. Anthanthrene-dibenzo[b,k]perylene
401. Anthracene-perylene
402. Coronene-anthracene
403. Triphenylene-benzo[ghi]perylene
404. Triphenylene-perylene
405. Perylene-acridine
406. Perylene-carbazole
407. Dibenzo[b,k]perylene-oxadiazole
408. Perylene-imidazole
409. Benzo[ghi]perylene-pyridine
410. Pyridine-perylene
411. Coronene-naphthyridine
412. Quinoline-perylene
413. Quinoline-dibenzo[b,k]perylene
414. Benzofuran-dibenzo[b,k]perylene
415. Dibenzo[b,d]furan-perylene
416. Isoquinoline-coronene
417. Acridine-benzo[ghi]perylene In the above examples 386 through 417, a hyphen represents a single chemical bond or a linkage via a saturated or unsaturated hydrocarbon group including alkenyl, alkynyl, PAH, a-PAH, and heterocycle or by a heteroatom N, O, or S between PAH and a-PAH moieties. Useful compounds include compounds such as PAH and a-PAH groups linked by one or more hydrocarbon groups.

Particularly preferred materials for the first host component of the luminescent layer of this invention include benzenoid compounds of the following structures:

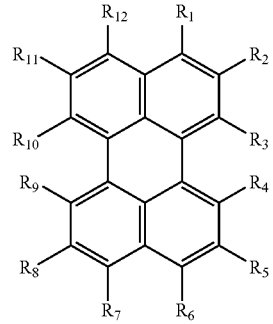

(a)

wherein:
substituents $R_1$ through $R_{12}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{12}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{12}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

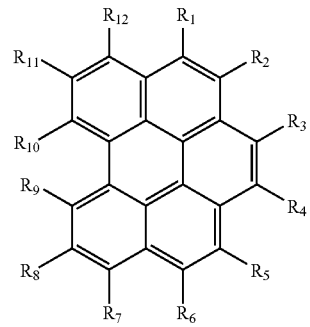

(b)

wherein:

substituents $R_1$ through $R_{12}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{12}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{12}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (c)

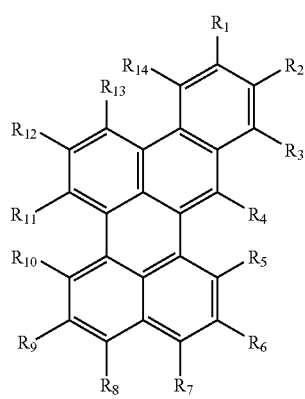

wherein:

substituents $R_1$ through $R_{14}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (d)

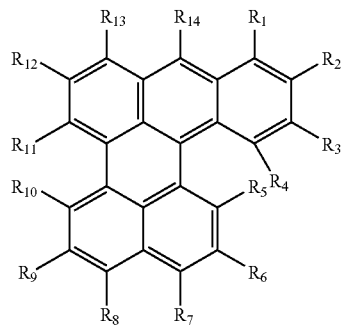

(e)

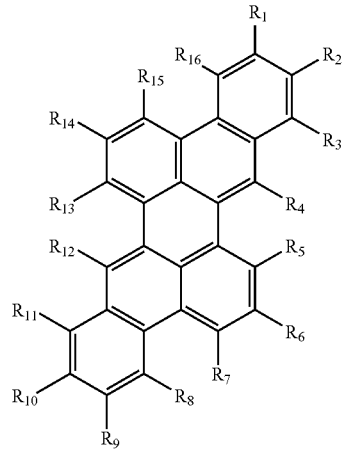

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

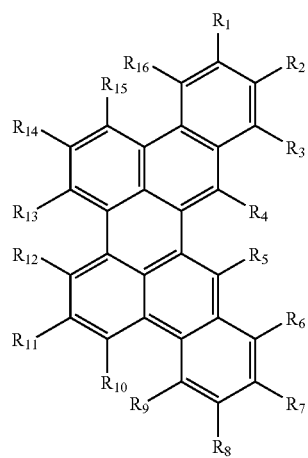

(f)

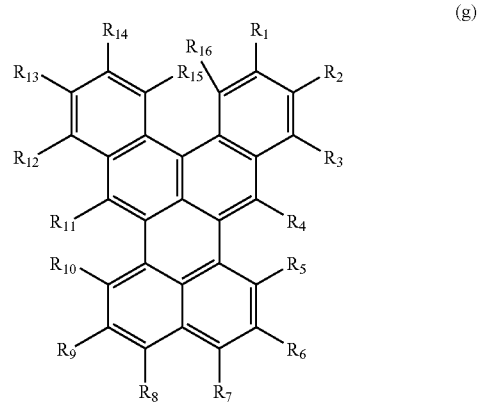

(g)

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

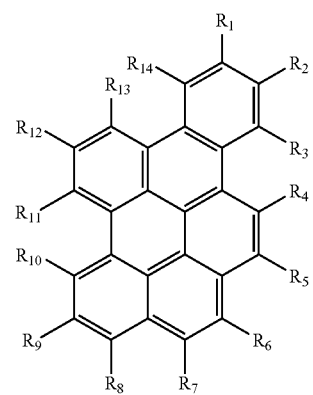

(h)

wherein:

substituents $R_1$ through $R_{14}$ are each individually hydrogen, fluoro, cyano, alkoxy, aryloxy, diarylamino, arylalkylamino, dialkylamino, trialkylsilyl, triarylsilyl, diarylalkyl-silyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

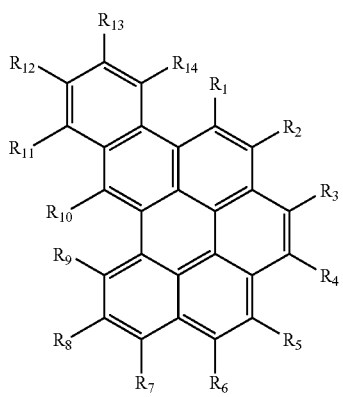

(i)

wherein:

substituents $R_1$ through $R_{14}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

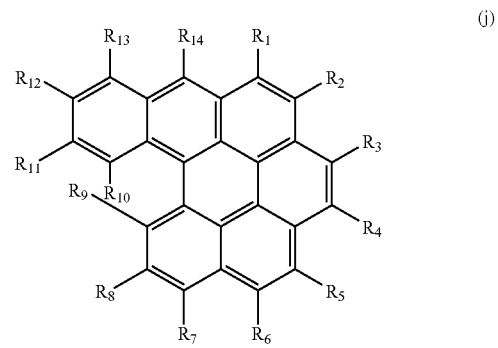

(j)

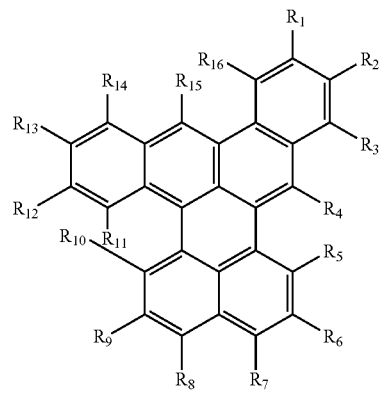

(k)

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

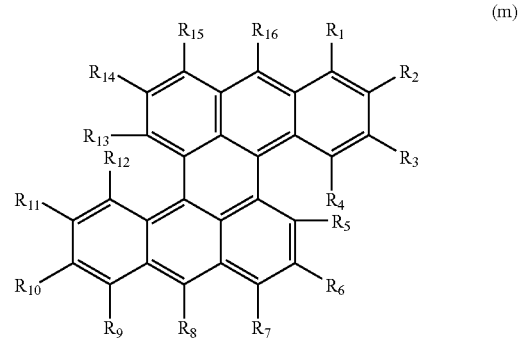

(m)

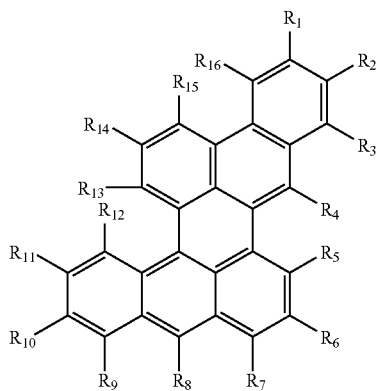

(l)

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

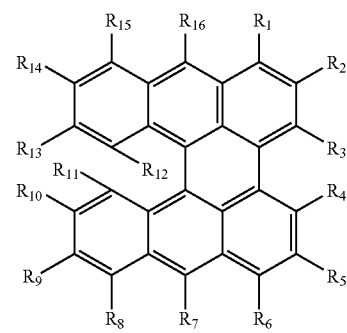

(n)

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent R₁ through R₁₆ substituents form an annelated benzo-, naphtho-, anthra-, phenanthro-, fluorantheno-, pyreno-, triphenyleno-, or peryleno-substituent or its alkyl or aryl substituted derivative; or any two R₁ through R₁₆ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

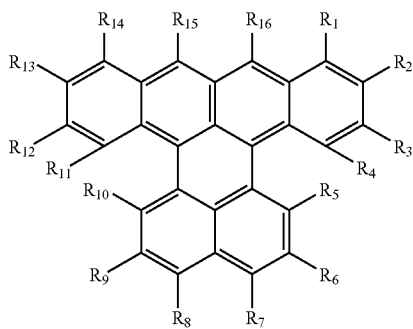

(o)

wherein:

substituents R₁ through R₁₆ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent R₁ through R₁₆ substituents form an annelated benzo-, naphtho-, anthra-, phenanthro-, fluorantheno-, pyreno-, triphenyleno-, or peryleno-substituent or its alkyl or aryl substituted derivative; or any two R₁ through R₁₆ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

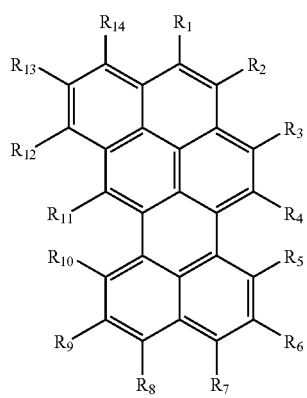

(p)

wherein:

substituents R₁ through R₁₄ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent R₁ through R₁₄ substituents form an annelated benzo-, naphtho-, anthra-, phenanthro-, fluorantheno-, pyreno-, triphenyleno-, or peryleno-substituent or its alkyl or aryl substituted derivative; or any two R₁ through R₁₄ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

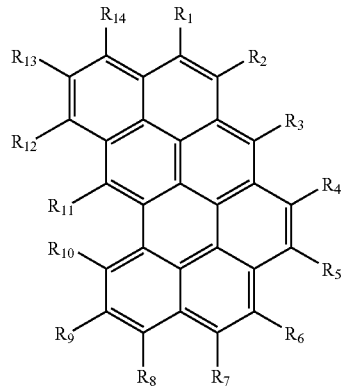

(q)

wherein:

substituents R₁ through R₁₄ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent R₁ through R₁₄ substituents form an annelated benzo-, naphtho-, anthra-, phenanthro-, fluorantheno-, pyreno-, triphenyleno-, or peryleno-substituent or its alkyl or aryl substituted derivative; or any two R₁ through R₁₄ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

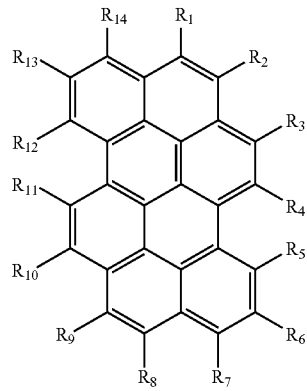

(r)

wherein:

substituents $R_1$ through $R_{14}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

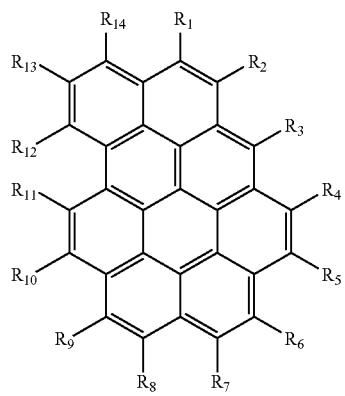

(s)

wherein:

substituents $R_1$ through $R_{14}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

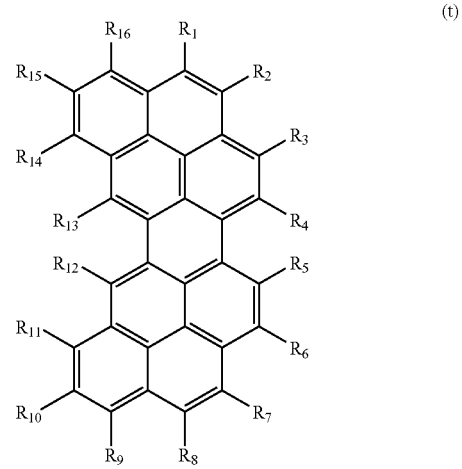

(t)

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (u)

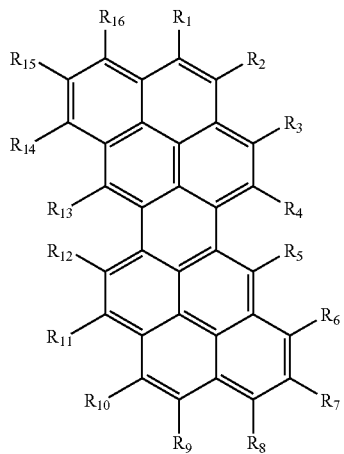

wherein:
substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (v)

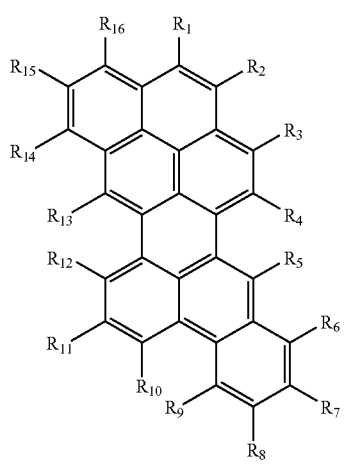

wherein:
substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (w)

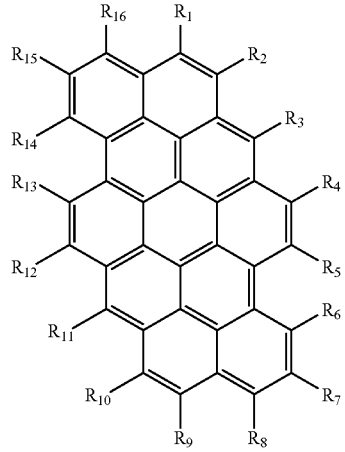

wherein:
substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

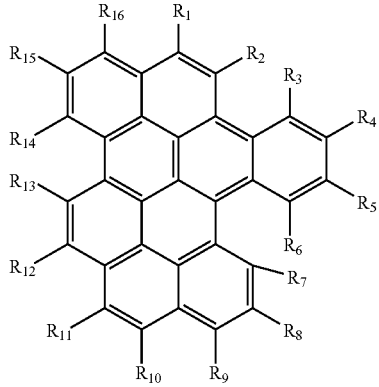

(x)

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

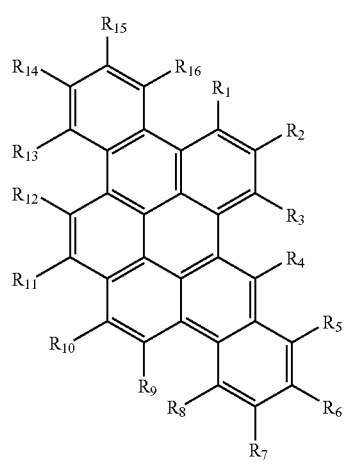

(y)

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

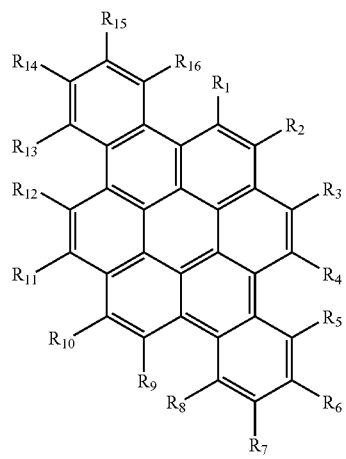

(z)

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (aa)

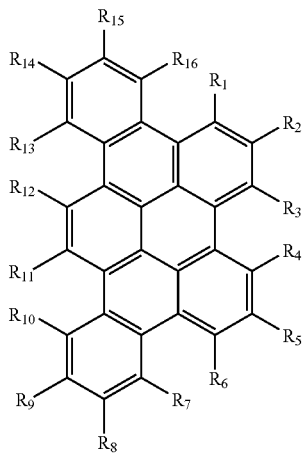

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (ab)

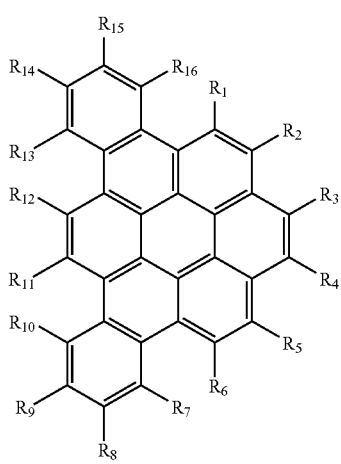

(ac)

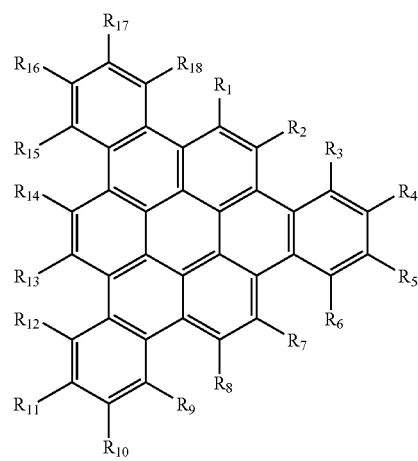

wherein:

substituents $R_1$ through $R_{18}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{18}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{18}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (ad)

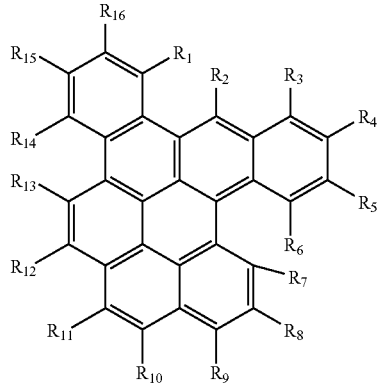

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (ae)

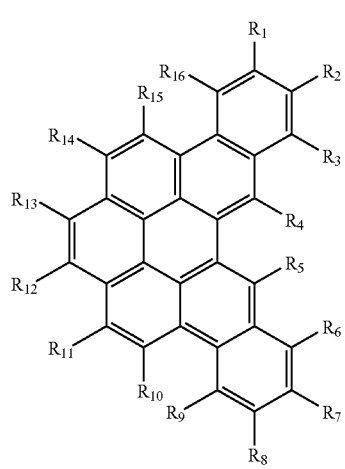

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (af)

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (ag)

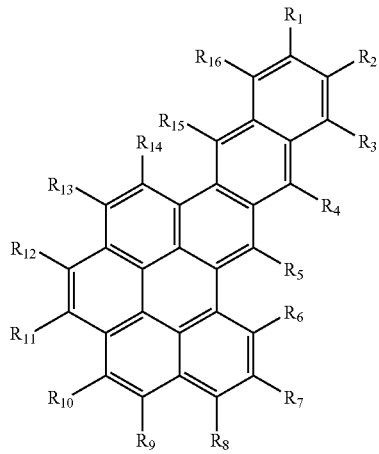

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (ah)

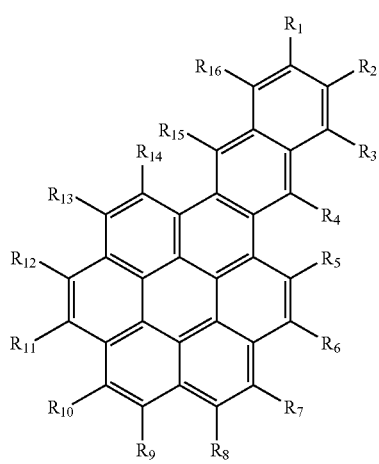

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (ai)

wherein:

substituents $R_1$ through $R_{18}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{18}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{18}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

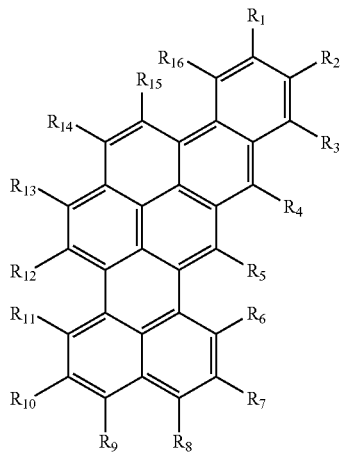

(aj)

wherein:

substituents R₁ through R₁₆ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent R₁ through R₁₆ substituents form an annelated benzo-, naphtho-, anthra-, phenanthro-, fluorantheno-, pyreno-, triphenyleno-, or peryleno-substituent or its alkyl or aryl substituted derivative; or any two R₁ through R₁₆ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (ak)

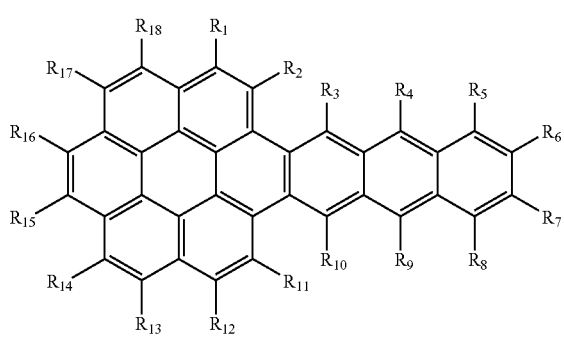

wherein:

substituents R₁ through R₁₈ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent R₁ through R₁₈ substituents form an annelated benzo-, naphtho-, anthra-, phenanthro-, fluorantheno-, pyreno-, triphenyleno-, or peryleno-substituent or its alkyl or aryl substituted derivative; or any two R₁ through R₁₈ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (al)

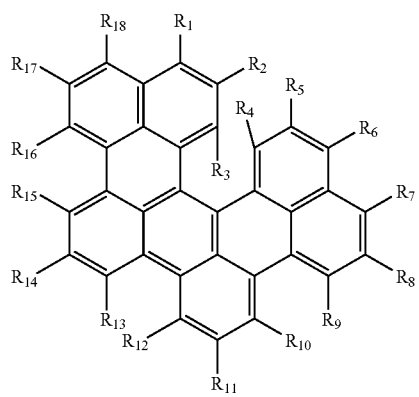

wherein:

substituents R₁ through R₁₈ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent R₁ through R₁₈ substituents form an annelated benzo-, naphtho-, anthra-, phenanthro-, fluorantheno-, pyreno-, triphenyleno-, or peryleno-substituent or its alkyl or aryl substituted derivative; or any two R₁ through R₁₈ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (am)

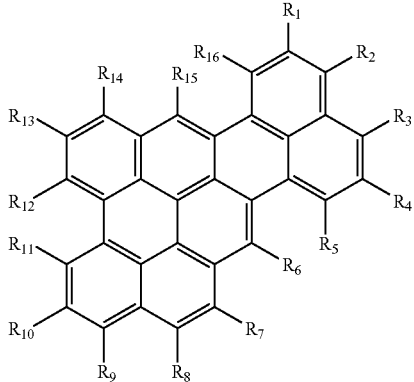

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (an)

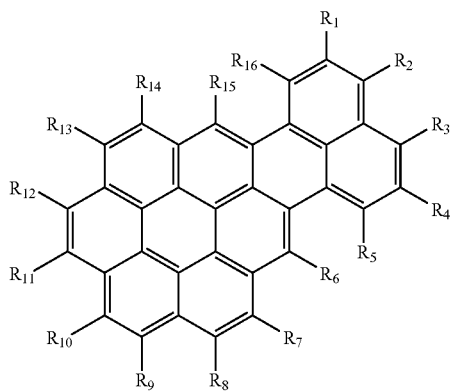

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (ao)

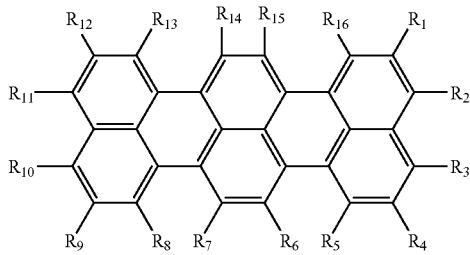

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (ap)

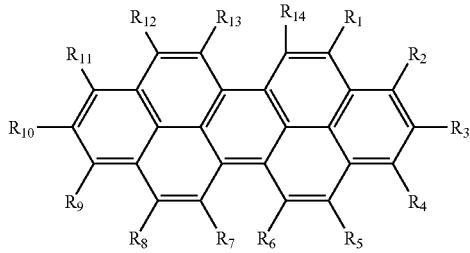

wherein:

substituents $R_1$ through $R_{14}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

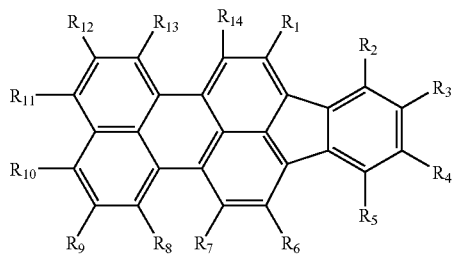

(aq)

wherein:

substituents $R_1$ through $R_{14}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

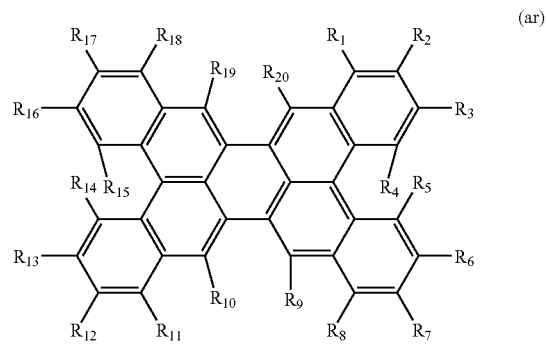

(ar)

wherein:

substituents $R_1$ through $R_{20}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{20}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{20}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

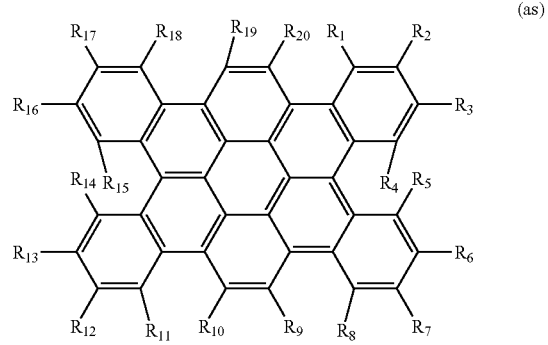

(as)

wherein:

substituents $R_1$ through $R_{20}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{20}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{20}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

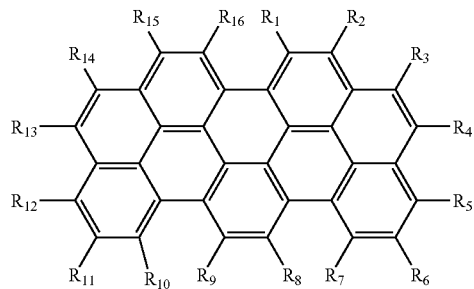

(at)

wherein:
substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

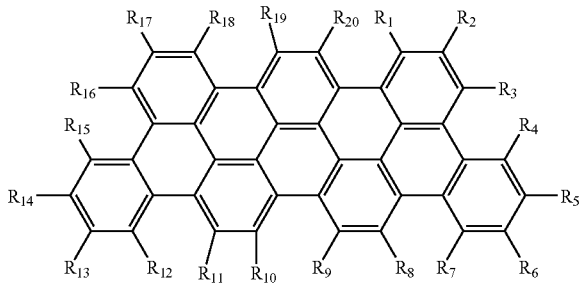

(au)

wherein:
substituents $R_1$ through $R_{20}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{20}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{20}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

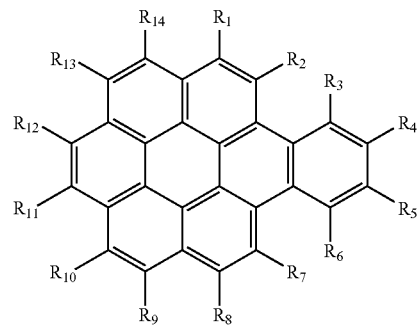

(av)

wherein:
substituents $R_1$ through $R_{14}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (aw)

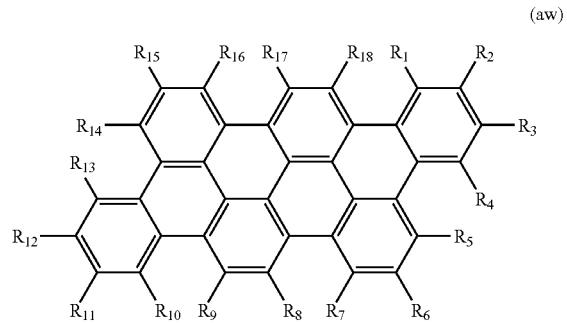

wherein:

substituents $R_1$ through $R_{18}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{18}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{18}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (ax)

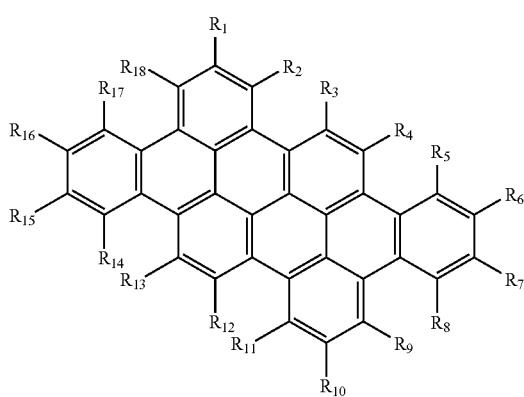

wherein:

substituents $R_1$ through $R_{18}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{18}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{18}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (ay)

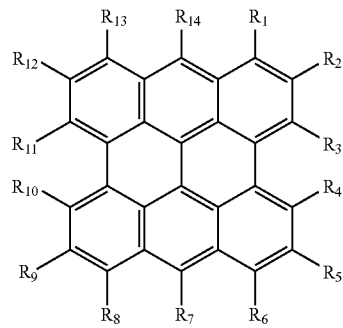

wherein:

substituents $R_1$ through $R_{14}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

53

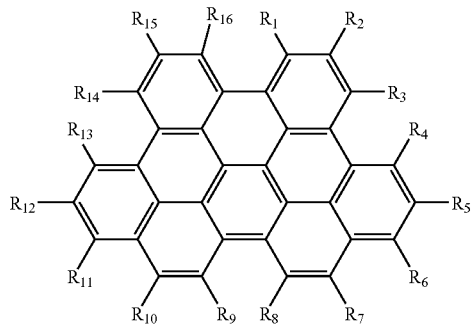
(az)

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (aaa)

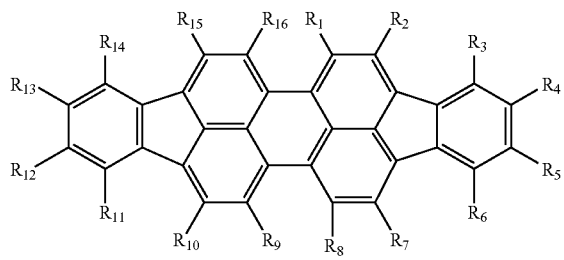

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or

54 peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (aab)

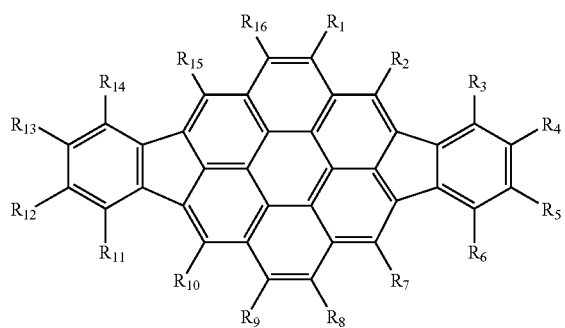

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (aac)

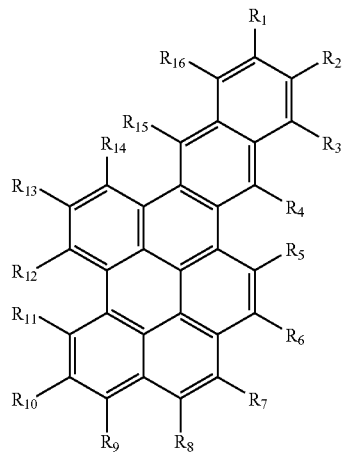

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

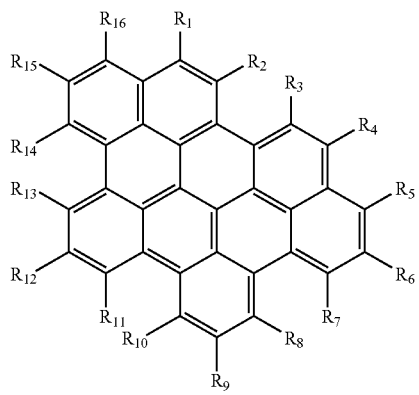

(aad)

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

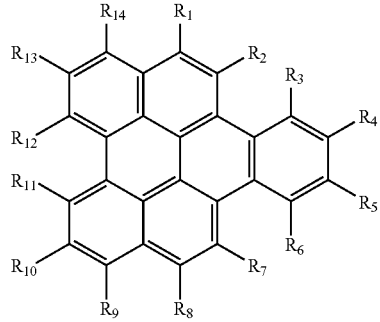

(aae)

wherein:

substituents $R_1$ through $R_{14}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

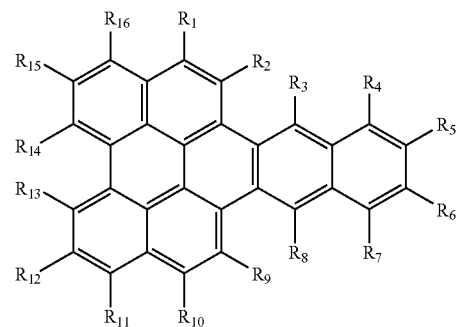

(aaf)

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (aag)

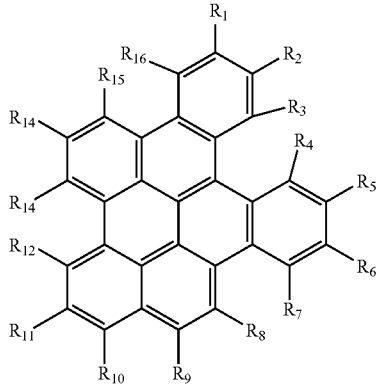

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (aah)

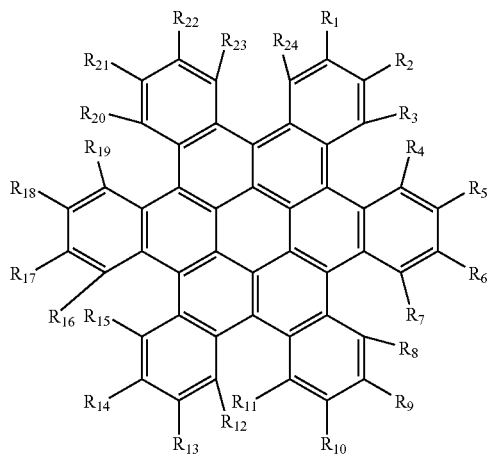

wherein:

substituents $R_1$ through $R_{24}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{24}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{24}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (aai)

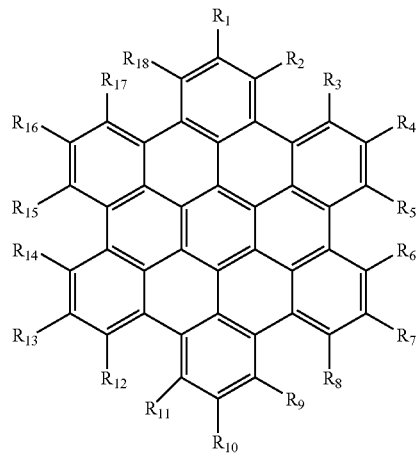

wherein:

substituents $R_1$ through $R_{18}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{18}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{18}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

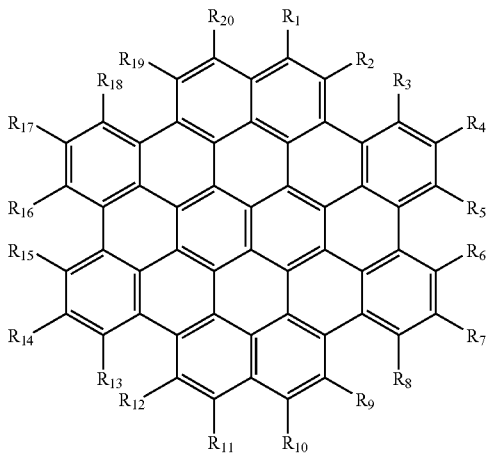

(aaj)

wherein:

substituents $R_1$ through $R_{20}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{20}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{20}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

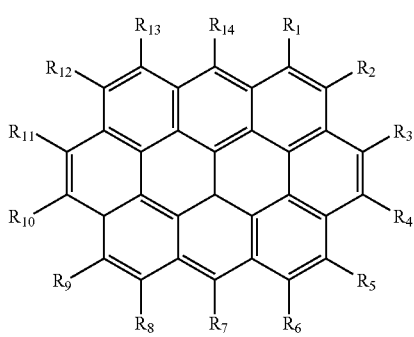

(aak)

wherein:

substituents $R_1$ through $R_{14}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or

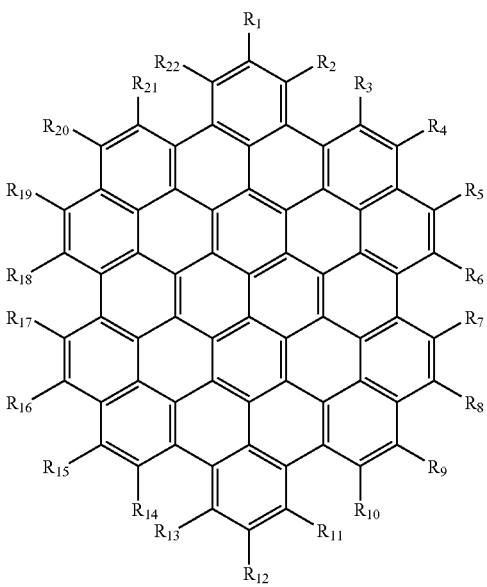

(aal)

wherein:

substituents $R_1$ through $R_{22}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{22}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{22}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (aam)

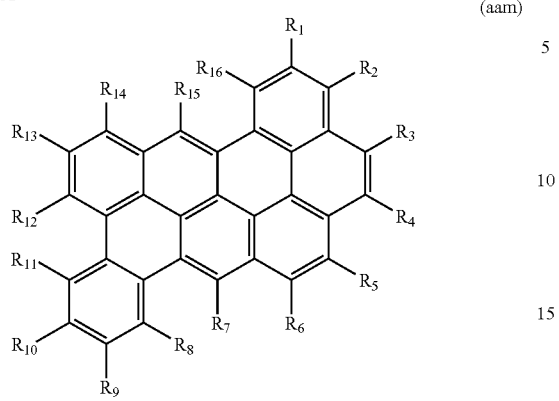

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (aan) PAH (or a-PAH) compounds that can be drawn using only fully aromatic benzene (or aza-benzene) rings so as to form graphite-like segments in the following fashion:

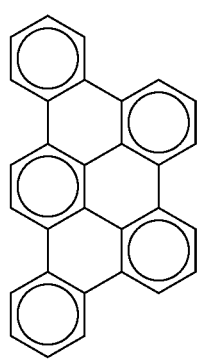
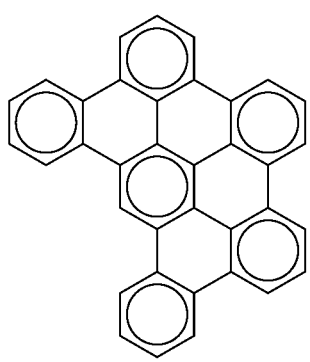

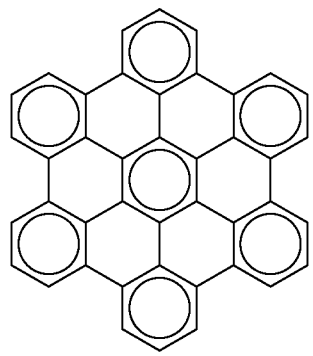
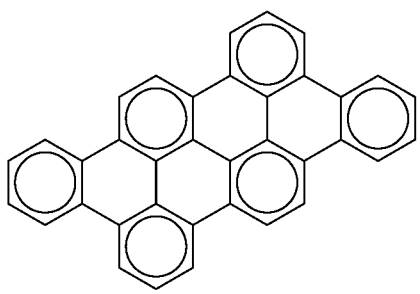
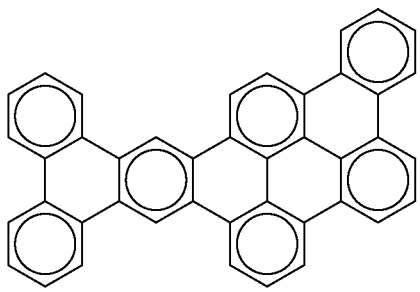
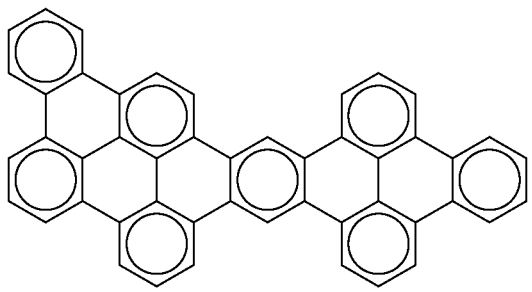
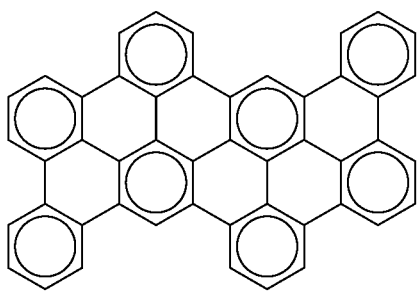

-continued
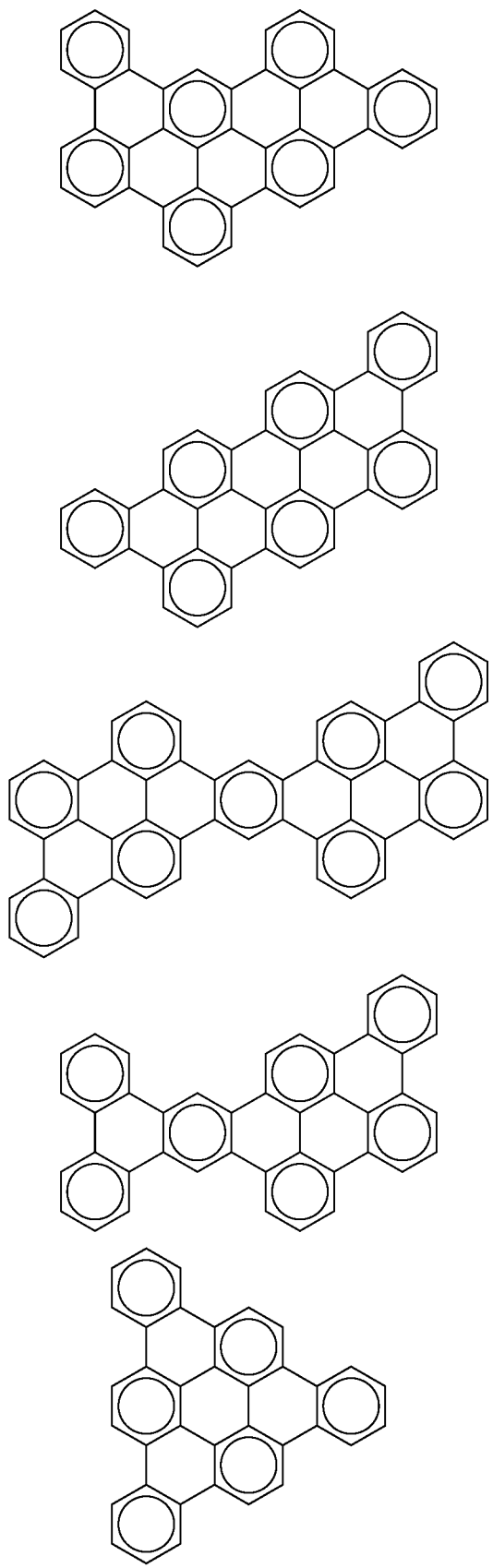
-continued
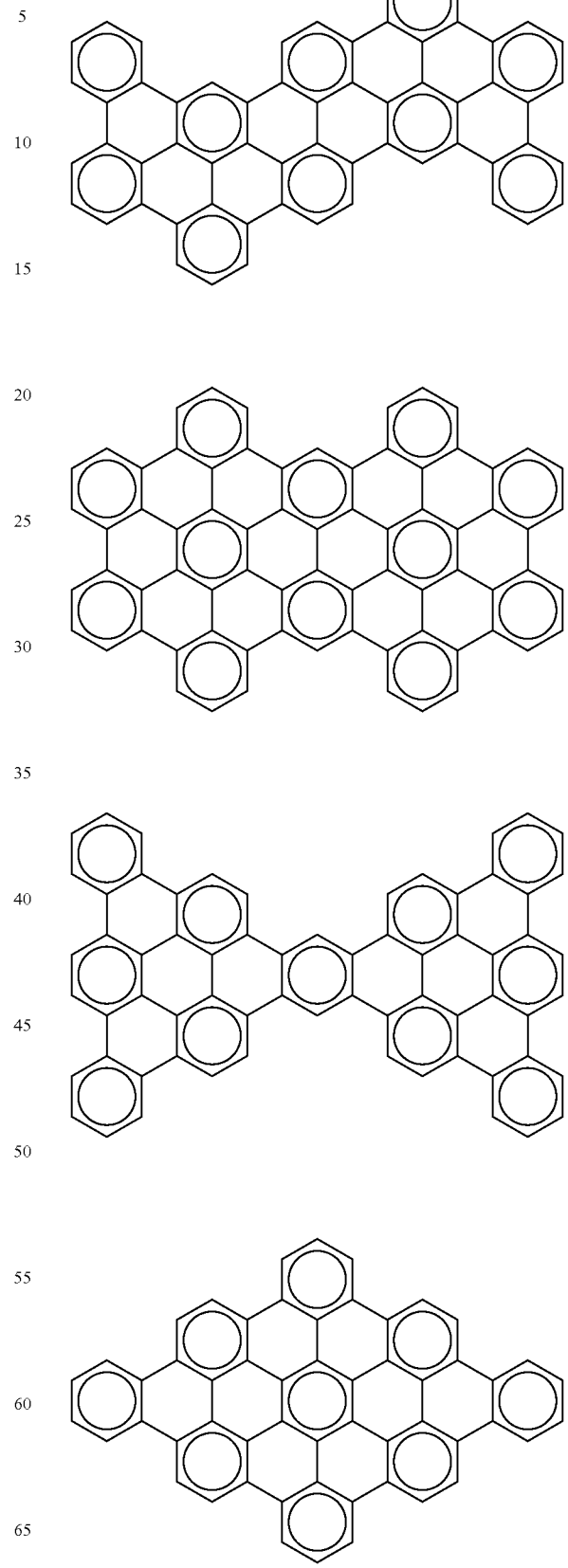

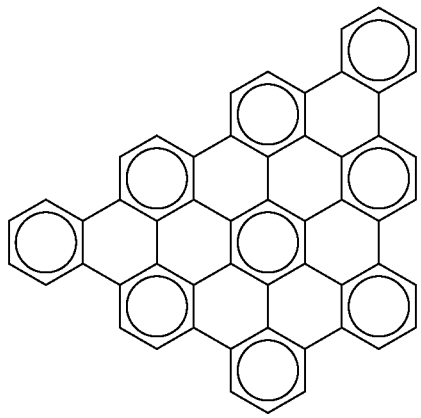

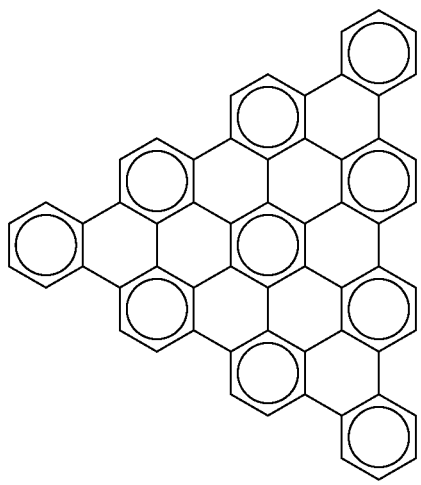

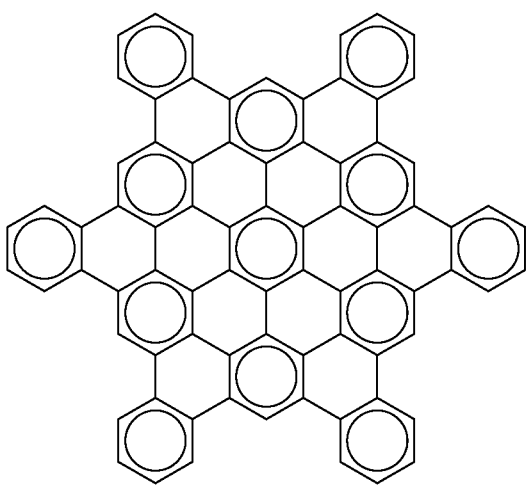

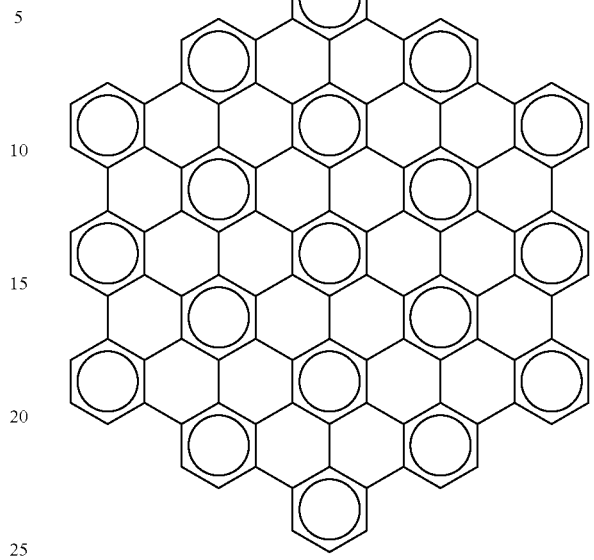

wherein:

substituents in each position for each compound and analogous compounds of the homological series are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent substituents form an annelated benzo-, naphtho-, anthra-, phenanthro-, fluorantheno-, pyreno-, triphenyleno-, or peryleno-substituent or its alkyl or aryl substituted derivative; or any two substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative; or (aao) any of the compounds 1 through 417.

One particular selection criterion for the first host component is that the compounds containing at least one perylene ring structure or at least one mono-aza-perylene or poly-aza-perylene ring structure or derivatives thereof should have a molecular structure that enables it to form both monomer state and aggregate state. Polycyclic hydrocarbons can interact with each other by ways of various forces including van der Waals effects, dipole interactions, etc. Interaction between two molecules can lead to aggregation. Initially a dimer can be formed. Further association leads to aggregate formation including many molecules. The properties of the aggregate can differ from those of the monomer. Interactions among polycyclic hydrocarbons that produce an aggregate state can induce absorption spectral shifts and distinct changes in band shape as well as changes in redox properties relative to the monomer. The aggregate state can be formed by at least two molecules of the same compound, such as the first host component, or by at least two molecules of two different compounds, such as the first and second host components or first component and the luminescent dopant. All these aggregate states are useful in the present invention. However, the following discussion will be focused on the first case. The monomer state is defined as a state where molecules of the first host component do not interact with each other in either ground or excited electronic state and thus behave as single molecules in a solid solution of the second component. Thus, in particular their absorption and emission processes involve just one molecule. The absence of the interaction can evolve e.g. due to the intrinsic lack of forces that enable the interaction, distances between the molecules being too large, improper geometry, steric hindrance, and other reasons. The aggregate state is defined as a state formed by an interaction, for example such as commonly known in the art van der Waals forces or by commonly known in the art charge-transfer interactions, of at least two molecules. It has physical and chemical properties different from those of the monomer state. In particular, two or more molecules can participate in cooperative absorption or emission or both, that is absorption or emission or both can only be understood as arising from molecular complexes or molecular aggregates. When two or more molecules act cooperatively to absorb a photon, it is said that the absorption aggregate exists in the ground electronic state. When two or more molecules act cooperatively to emit a photon, it is said that the exciplex, or a molecular complex or molecular aggregate, exists in the excited electronic state. The absorption aggregate need not form an exciplex upon excitation and the exciplex need not emit to produce a ground state aggregate. Thus, the aggregate state can exist in either ground electronic state or excited electronic state or both. An aggregate state can be only weakly associated in the ground electronic state (the energy of van der Waals interactions ~1–3 kcal/mol) but more strongly associated in its excited electronic state (the energy of van der Waals interactions ~3–10 kcal/mol). The simplest aggregate state in the ground electronic state is often called a dimer, that is an aggregate state formed by two molecules in their ground electronic states. The aggregate state in the excited electronic state is called an excimer and in the simplest case is formed by two molecules one of which prior to formation of the exciplex was in the ground electronic state and the other was in the excited electronic state. One of the most commonly observed features of aggregate states is that either their absorption spectrum or their emission spectrum or both are shifted compared to the absorption spectrum or emission spectrum or both, respectively, of the monomer state. The shift can occur to the red or to the blue. On the other hand, the absorption or emission spectra or both of aggregate states can contain new features such as peaks and shoulders positioned to either red or blue compared to the absorption or emission spectrum or both of the monomer state, respectively. Another most commonly observed characteristic of aggregate states is that the intensity and sometimes the position (wavelength) of the new or shifted absorption or emission or both depend on concentration of molecules that form the aggregate state. With increasing concentration, the intensity of shifted absorption or emission features or both can increase due to the increasing concentration of the aggregate states, while the position, or wavelength, can shift too due to the increase in the size (number of molecules involved in the formation) of the aggregate states. Another common characteristic of aggregate states which is observed in the absence of readily detectable changes in the monomer absorption or emission spectrum or both is the change in the intensity (quantum yield of luminescence) of the monomer emission. For reference, these definitions can be found in N. J. Turro, Modern Molecular Photochemistry, University Science Books, Sausalito, Calif. 1991.

For some organic compounds, their molecular structure is such that their aggregates in excited electronic states are emissive, and thus can be readily observed by measuring fluorescence emission spectra as a function of concentration. PAH compounds containing at least one perylene ring structure and a-PAH compounds containing at least one mono-aza-perylene or poly-aza-perylene ring structure are some of the most prominent examples of such organic compounds (see for example FIGS. 4–9; Table 1). Among these, compounds that form emissive and highly emissive aggregate states are potentially the most useful as first host components. However, there are many organic compounds that form aggregate states which are not emissive or only weakly emissive. Formation of completely or essentially non-emissive aggregate states (that is those with the quantum yield of luminescence of zero or near zero) can lead to a decrease in the efficiency of electroluminescence and photoluminescence due to insufficient efficiency of electronic excitation energy transfer to the luminescent dopant. Nevertheless, for certain types of compounds, especially the ones listed above, the quantum yield of luminescence of an aggregate state is most often found to be non-zero. This can be sufficient to sustain a sufficient rate of electronic excitation energy to the luminescent dopant, if the latter acts as a sufficiently strong acceptor in the well known in the art Foerster energy transfer process. Therefore, such compounds would not compromise the electroluminescence efficiency and could also be useful as first host components. Their use would result not only in improved operational lifetimes but also in excellent EL efficiencies. On the other hand, if the acceptor (luminescent dopant) of the excitation energy transfer is strong and its concentration is sufficiently high so that the quantum efficiency of the energy transfer is ~100% then even if the quantum yield of luminescence of the donor decreases by 10–15 times (given that everything else remains equal) the quantum efficiency of the energy transfer, and thus of the acceptor luminescence, decreases only by ~10%.

Another important criteria for selection of compounds as first host components is that the aggregate states of this compound should have spectroscopic characteristics, namely absorption and emission spectra, excited state lifetime, quantum yield of luminescence, and oscillator strength, such that efficient transfer of electronic excitation energy to the luminescent dopant of appropriate color is insured.

Many of the PAH compounds containing at least one perylene ring structure and a-PAH compounds containing at least one mono-aza-perylene or poly-aza-perylene ring structure found useful as the first host component in the present invention have a flat rigid geometry, which encourages formation of aggregate states. Many representative benzenoids, such as perylene, coronene, benzo[ghi] perylene, ovalene, etc., their mono-aza- and poly-aza-analogs, and their mono- and poly-substituted benzo, naphtho, anthra, phenanthro, triphenyleno, and other derivatives have been shown in the common literature to possess a pronounced propensity for aggregate state formation. The aggregate states of these compounds are extensively characterized in common literature. If the PAH compounds containing at least one perylene ring structure and a-PAH compounds containing at least one mono-aza-perylene or poly-aza-perylene ring structure are emissive in its monomer state, they are most often found to be emissive in their aggregate state also, especially in the solid solutions and in the absence of oxygen (exactly as found inside an OLED device). Other organic compounds meeting such a planar geometry criteria are useful as well.

Although aggregate states including two molecules are most often found and described in the literature, often it is found that compounds such as disclosed in the present invention are capable of forming aggregate states including not only two molecules, but of three, four, five, ten, hundred, thousand and more molecules as the volume % increases. With sufficiently high number of molecules of the first host component participating in the formation of an aggregate state, a domain could be formed where certain degree of order or degree of crystallinity could be found. The size of these domains could be in the range of nanometers (nanocrystalline domain) or even micrometers (microcrystalline domain).

Materials for the second host component of the luminescent layer of the present invention include organic compounds that are capable of forming a continuous and substantially pin-hole-free thin film upon mixing with the first host component. They can be polar, such as (i) the common host for green, yellow, orange, and red OLEDs AlQ$_3$ and other oxinoid and oxinoid-like materials and metal complexes, and (ii) common hosts of heterocyclic family for blue, blue-green, green, yellow, orange, and red OLEDs such as those based on oxadiazole, imidazole, pyridine, phenanthroline, triazine, triazole, quinoline and other moieties. They also can be nonpolar, such as (i) the common hosts of anthracene family for blue, blue-green, green, yellow, orange, and red OLEDs, such as 2-(1,1-dimethylethyl)-9,10-bis(2-naphthalenyl)anthracene (TBADN), 9,10-Bis[4-(2,2-diphenylethenyl)phenyl]anthracene, and 10,10'-Diphenyl-9,9'-bianthracene; (ii) common hosts of rubrene family for yellow, orange, and red OLEDs, such as rubrene and 5,6,11,12-tetrakis(2-naphthyl)tetracene; and (iii) common hosts of triarylamine family for blue, blue-green, green, yellow, orange, and red OLEDs such as NPB, TNB, and TPD. The second host component can have a bandgap that is less than, more than, or equal to that of the first host component in either its monomer state or aggregate state. The bandgap (or energy gap) is defined as the energy needed to bring an electron from the highest occupied molecular orbital to the lowest unoccupied molecular orbital of the molecule. When the bandgap of the first host component in its monomer state is approximately equal to that of the second host component and the dopant is absent, the photoluminescence (PL) and electroluminescence (EL) spectra are composed of the emission spectra of both species. This can be seen in FIGS. 4–9. When the bandgap of the first host component in its monomer state is approximately equal to that of the first host component in its aggregate state and to that of the second host component (while the dopant is absent), the PL and EL spectra are composed of the emission spectra of all three species. This also can be seen for example in FIGS. 4–9. When the bandgap of the first host component in its aggregate state is smaller than that of the second host component and the dopant is absent, the PL and EL spectra are dominated by the emission spectrum of the first host component in its aggregate state. This can be seen once again in FIGS. 4–9. Note that in all these cases the composition of the PL and EL spectra is also a subject to concentration, particularly of the aggregates of the first host component, and to quantum yield of luminescence and lifetime of the singlet excited states of all the species involved.

The necessary condition is that the bandgap of the luminescent dopant be smaller than the bandgap of the second host component, the bandgap of first host component in its monomer state, and the bandgap of the first host component in its aggregate state. This ensures that electronic excitation energy transfer from the first and second host components, resulting from the recombination of electrons and holes in the first and second host components, to the light-producing dopants is favorable.

Any one of the following three—second host component, the first host component in its monomer state, and the first host component in its aggregate state—can have the lowest bandgap between the three. The lowest bandgap material can also serve as a hole trap, an electron trap, or both, but so can the species that does not necessarily have the lowest bandgap. Trapping injected and transported carriers directly on the molecules of a single host component can be beneficial as it promotes electron-hole recombination in this host component, shortcutting the need for carrier recombination in the other host component which can have implications for the size, density distribution, and geometry of the recombination zone as well as operational stability of OLED devices. Under this condition, the other host component is needed for carrier transport only and not for charge carrier recombination.

The first preferred class of materials for the second host component is the oxinoid compounds. Exemplary of contemplated oxinoid compounds are those satisfying the following structural formula:

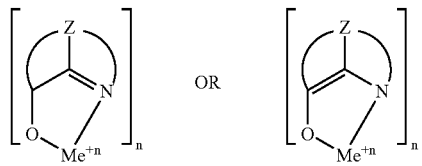

wherein:

Me represents a metal;

n is an integer of from 1 to 3; and

Z independently in each occurrence represents the atoms completing a nucleus having at least two fused aromatic rings.

From the foregoing it is apparent that the metal can be monovalent, divalent, or trivalent metal. The metal can, for example, be an alkali metal, such as lithium, sodium, rubidium, cesium, or potassium; an alkaline earth metal, such as magnesium, strontium, barium, or calcium; or an earth metal, such as boron or aluminum, gallium, and indium. Generally any monovalent, divalent, or trivalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is preferably maintained at 18 or less.

Illustrative of useful chelated oxinoid compounds and their abbreviated names are the following:

AlQ$_3$: Aluminum trisoxine [alias, tris(8-quinolinolato)aluminum(III)];

MgQ₂: Magnesium bisoxine [alias, bis(8-quinolinolato) magnesium(II)];

ZnQ₂: Bis[benzo{f}-8-quinolinolato]zinc (II);

Al₂O(2-MeQ)₄: Bis(2-methyl-8-quinolinolato)aluminum (III)-μ-oxo-bis(2-methyl-8-quinolinolato)aluminum(III);

InQ₃: Indium trisoxine [alias, tris(8-quinolinolato)indium];

Aluminum tris(5-methyloxine)[alias, tris(5-methyl-8-quinolinolato)aluminum(III)];

LiQ: Lithium oxine [alias, (8-quinolinolato)lithium(I)];

GaQ₃: Gallium oxine [alias, tris(8-quinolinolato)gallium (III)]; and

Zirconium oxine [alias, tetra(8-quinolinolato)zirconium (IV)].

The list further includes SCQ₃, BeBq₂ (bis(10-hydroxybenzo[h]quinolinato)-beryllium), Al(4-MeQ)₃, Al(2-MeQ)₃, Al(2,4-Me₂Q)₃, Al₂O(2-MeQ)₄, Ga(4-MeQ)₃, Ga(2-MeQ)₃, Ga(2,4-Me₂Q)₃, and Mg(2-MeQ)₂. The list of oxinoid compounds further includes metal complexes with two bi-dentate ligands and one mono-dentate ligand, for example Al(2-MeQ)₂(X) where X is any aryloxy, alkoxy, arylcaboxylate, and heterocyclic carboxylate group.

Another class of materials useful as the second host component includes structures having an anthracene moiety. Exemplary of contemplated anthracene compounds are those satisfying the following structural formula:

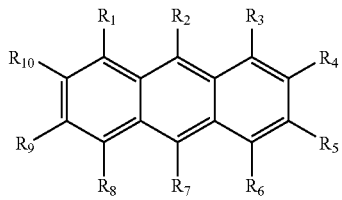

wherein:

substituents R₂ and R₇ are each individually and independently hydrogen, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; and substituents R₁ through R₁₀ excluding R₂ and R₇ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent R₁ through R₁₀ substituents excluding R₂ and R₇ form an annelated benzo-, naphtho-, anthra-, phenanthro-, fluorantheno-, pyreno-, triphenyleno-, or peryleno-substituent or its alkyl or aryl substituted derivative; or any two adjacent R₁ through R₁₀ substituents excluding R₂ and R₇ form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

Illustrative of useful anthracene compounds and their abbreviated names are the following:

2-(1,1-dimethylethyl)-9,10-bis(2-naphthalenyl)anthracene (TBADN);

9,10-bis(2-naphthalenyl)anthracene (ADN);

9,10-bis(1-naphthalenyl)anthracene;

9,10-Bis[4-(2,2-diphenylethenyl)phenyl]anthracene;

9,10-Bis([1,1':3',1''-terphenyl]-5'-yl)anthracene;

9,9'-Bianthracene;

10,10'-Diphenyl-9,9'-bianthracene;

10,10'-Bis([1,1':3',1''-terphenyl]-5'-yl)-9,9'-bianthracene;

2,2'-Bianthracene;

9,9',10,10'-Tetraphenyl-2,2'-bianthracene;

9,10-Bis(2-phenylethenyl)anthracene; or

9-Phenyl-10-(phenylethynyl)anthracene.

Another class of materials useful as the second host component includes structures having an amine moiety. Exemplary of contemplated amino compounds are those satisfying the following structural formula:

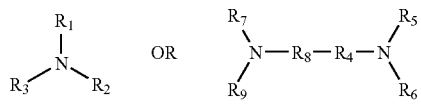

wherein:

substituents R₄ and R₈ are each individually and independently aryl, or substituted aryl of from 5 to 30 carbon atoms, heterocycle containing at least one nitrogen atom, or at least one oxygen atom, or at least one sulfur atom, or at least one boron atom, or at least one phosphorus atom, or at least one silicon atom, or any combination thereof; substituents R₄ and R₈ each or together ("R₄—R₈") representing an aryl group such as benzene, naphthalene, anthracene, tetracene, pyrene, perylene, chrysene, phenathrene, triphenylene, tetraphene, coronene, fluoranthene, pentaphene, ovalene, picene, anthanthrene and their homologs and also their 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituted derivatives; and substituents R₁ through R₉ excluding R₄ and R₈ are each individually hydrogen, silyl, alkyl of from 1 to 24 carbon atoms, aryl of from 5 to carbon atoms, substituted aryl, heterocycle containing at least one nitrogen atom, or at least one oxygen atom, or at least one sulfur atom, or at least one boron atom, or at least one phosphorus atom, of at least one silicon atom, or any combination thereof.

Illustrative of useful amino compounds and their abbreviated names are the following:

N,N'-Bis(N'',N''-diphenylaminonaphthalen-5-yl)-N,N'-diphenyl-1,5-diaminonaphthalene (CAS 503624-47-3);

1,1-Bis(4-di-p-tolylaminophenyl)-4-phenylcyclohexane;

1,1-Bis(4-di-p-tolylaminophenyl)cyclohexane;

1,5-Bis[N-(2-naphthyl)-N-phenylamino]naphthalene;

1,5-Bis[N-(1-naphthyl)-N-phenylamino]naphthalene;

2,6-Bis(di-p-tolylamino)naphthalene;

2,6-Bis[di-(1-naphthyl)amino]naphthalene;

2,6-Bis[N-(1-naphthyl)-N-(2-naphthyl)amino]naphthalene;

2,6-Bis[N,N-di(2-naphthyl)amine]fluorene;

4-(di-p-tolylamino)-4'-[4(di-p-tolylamino)-styryl]stilbene;
4,4"-Bis[N-(1-anthryl)-N-phenylamino]-p-terphenyl;
4,4"-Bis[N-(1-naphthyl)-N-phenylamino]p-terphenyl;
4,4',4"-tris[(3-methylphenyl)phenylamino]triphenylamine;
4,4'-Bis[N-(1-naphthyl)-N-(2-naphthyl)amino]biphenyl (TNB);
4,4'-Bis[N-(3-methylphenyl)-N-phenylamino]biphenyl (TPD);
4,4'-Bis(diphenylamino)quadriphenyl;
4,4'-Bis[N-(1-coronenyl)-N-phenylamino]biphenyl;
4,4'-Bis[N-(1-naphthyl)-N-phenylamino]biphenyl (NPB);
4,4'-Bis[N-(2-naphthacenyl)-N-phenylamino]biphenyl;
4,4'-Bis[N-(2-naphthyl)-N-phenylamino]biphenyl;
4,4'-Bis[N-(2-perylenyl)-N-phenylamino]biphenyl;
4,4'-Bis[N-(2-phenanthryl)-N-phenylamino]biphenyl;
4,4'-Bis[N-(2-pyrenyl)-N-phenylamino]biphenyl;
04,4'-Bis[N-(3-acenaphthenyl)-N-phenylamino]biphenyl;
4,4'-Bis[N-(8-fluoranthenyl)-N-phenylamino]biphenyl;
4,4'-Bis[N-(9-anthryl)-N-phenylamino]biphenyl;
4,4'-Bis[N-phenyl-N-(2-pyrenyl)amino]biphenyl;
4,4'-Bis {N-phenyl-N-[4-(1-naphthyl)-phenyl] amino}biphenyl;
Bis(4-dimethylamino-2-methylphenyl)-phenylmethane;
N,N,N',N'-Tetra(2-naphthyl)-4,4"-diamino-p-terphenyl;
N,N,N',N'-Tetraphenyl-4,4'-diaminobiphenyl;
N,N,N',N'-Tetra-p-tolyl-4-4'-diaminobiphenyl;
N,N,N',N'-tetra-1-naphthyl-4,4'-diaminobiphenyl;
N,N,N-Tri(p-tolyl)amine; or
N,N'-di-1-naphthalenyl-N,N'-diphenyl-4,4'-diaminobiphenyl N-Phenylcarbazole.

Another class of materials useful as the second host component includes structures having a fluorene moiety. Exemplary of contemplated fluorene compounds are those satisfying the following structural formula:

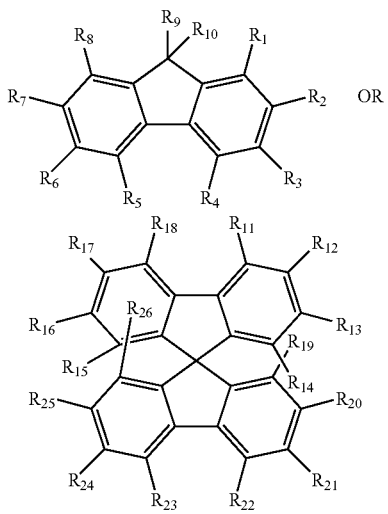

wherein:

substituents $R_1$ through $R_{25}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{25}$ substituents excluding $R_9$ and $R_{10}$ form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{25}$ substituents excluding $R_9$ and $R_{10}$ form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

Illustrative of useful fluorene compounds and their abbreviated names are the following:
2,2',7,7'-Tetraphenyl-9,9'-spirobi[9H-fluorene];
2,2',7,7'-Tetra-2-phenanthrenyl-9,9'-spirobi[9H-fluorene];
2,2'-Bis(4-N,N-diphenylaminophenyl)-9,9'-spirobi[9H-fluorene](CAS 503307-40-2);
4'-Phenyl-spiro[fluorene-9,6'-[6H]indeno[1,2-j]fluoranthene];
2,3,4-Triphenyl-9,9'-spirobifluorene;
11,11'-Spirobi[1H-benzo[b]fluorene];
9,9'-Spirobi[9H-fluorene]-2,2'-diamine;
9,9'-Spirobi[9H-fluorene]-2,2'-dicarbonitrile;
2',7'-Bis([1,1'-biphenyl]-4-yl)-N,N,N',N'-tetraphenyl-9,9'-spirobi[9H-fluorene]-2,7-diamine;
9,9,9',9',9",9"-Hexaphenyl-2,2':7',2"-ter-9H-fluorene;
2,7-Bis([1,1'-biphenyl]-4-yl)-9,9'-spirobi[9H-fluorene];
2,2',7,7'-tetra-2-Naphthalenyl-9,9'-spirobi[9H-fluorene]; or
9,9'-[(2,7-Diphenyl-9H-fluoren-9-ylidene)di-4,1-phenylene]bis-anthracene.

Another class of materials useful as the second host component includes structures having a naphthacene moiety. Exemplary of contemplated naphthacene compounds are those satisfying the following structural formula:

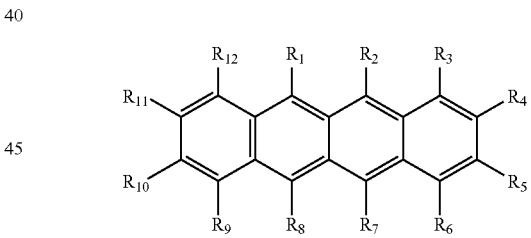

wherein:

substituents $R_1$ through $R_{12}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{12}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{12}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

Illustrative of useful naphthacene compounds and their abbreviated names are the following:
5,6,11,12-Tetraphenylnaphthacene (rubrene);
5,12-Bis(2-naphthyl)-6,11-diphenyltetracene;
5,12-Bis(2-mesityl)-6,11-diphenyltetracene;
5,12-Bis(1-naphthyl)-6,11-diphenyltetracene;
5,6,11,12-Tetrakis(2-naphthyl)tetracene;
10,10'-[(6,11-Diphenyl-5,12-naphthacenediyl)di-4,1-phenylene]bis[2,3,6,7-tetrahydro-1H,5H-benzothiazolo[5,6,7-ij]quinolizine;
9,10,15,16-Tetraphenyl-dibenzo[a,c]naphthacene;
5,6,13,14-Tetraphenylpentacene;
4,4'-(8,9-Dimethyl-5,6,7,10,11,12-hexaphenyl-1,4-naphthacenediyl)bis-benzonitrile;
4,4'-(8,9-Dimethoxy-5,6,7,10,11,12-hexaphenyl-1,4-naphthacenediyl)bis[N,N-diphenylbenzenamine];
1,2,3,5,6,11,12-Heptaphenylnaphthacene;
1,4,5,6,7,10,11,12-Octaphenylnaphthacene;
6,11-diphenyl-5,12-bis(4'-N,N-diphenylaminophenyl)naphthacene;
7,8,15,16-Tetraphenyl-benzo[a]pentacene;
2,3,5,6,11,12-Hexaphenylnaphthacene;
6,11-diphenyl-5,12-bis(4'-cyanophenyl)naphthacene;
6,11-diphenyl-5,12-bis(4'-(2-thienyl)phenyl)naphthacene; or
9,10,19,20-Tetraphenyl-tetrabenzo[a,cj,l]naphthacene.

Another class of materials useful as the second host component includes benzenoids that contain other heterocyclic structures. These structures include benzoxazolyl, and thio and amino analogs of benzoxazolyl of following general molecular structure:

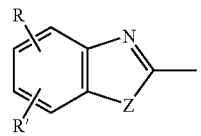

wherein:
Z is O, NR" or S; R and R', are individually hydrogen, alkyl of from 1 to 24 carbon atoms, aryl or hetero-atom substituted aryl of from 5 to 20 carbon atoms, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or atoms necessary to complete a fused aromatic ring; and R" is hydrogen; alkyl of from 1 to 24 carbon atoms; or aryl of from 5 to 20 carbon atoms. These structures further include alkyl, alkenyl, alkynyl, aryl, substituted aryl, benzo-, naphtho-, anthra-, phenanthro-, fluorantheno-, pyreno-, triphenyleno-, or peryleno-, 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, indeno, fluoro, cyano, alkoxy, aryloxy, amino, aza, heterocyclic, keto, or dicyanomethyl derivatives thereof.

The material selection criteria for the dopant in the luminescent layer are: 1) the dopant molecule has a high efficiency of fluorescence or phosphorescence in the luminescent layer, and 2) it has a bandgap (singlet bandgap for the case of fluorescent dopants and triplet bandgap for the case of phosphorescent dopants) smaller than that of the both first and second host materials, the first component being either in its monomer state or its aggregate state.

For red-emitting OLEDs, a preferred class of dopants of this invention is the DCM class and has the general formula:

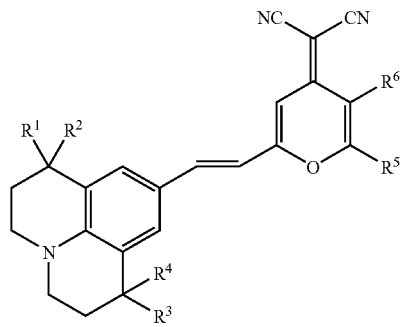

wherein:
$R^1$, $R^2$, $R^3$, and $R^4$ are individually alkyl of from 1 to 10 carbon atoms; $R^5$ is alkyl of from 2 to 20 carbon atoms, aryl, sterically hindered aryl, or heteroaryl; and $R^6$ is alkyl of from 1 to 10 carbon atoms, or a 5- or 6-membered carbocyclic, aromatic, or heterocyclic ring connecting with $R^5$.

These materials possess fluorescence efficiencies as high as unity in solutions and emit in the orange and red spectral region. Representative materials of this class and their abbreviated names include:

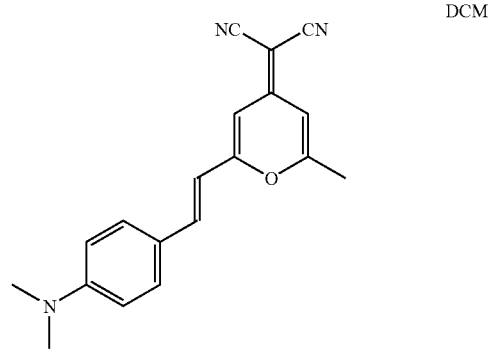

DCM

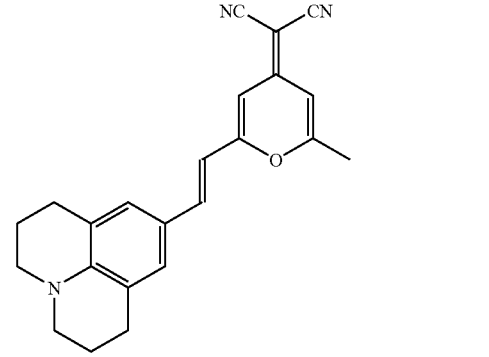

DCJ

-continued

DCJT
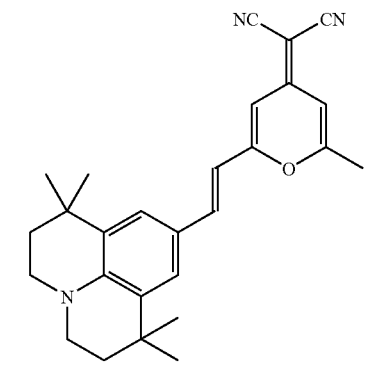

DCJTE
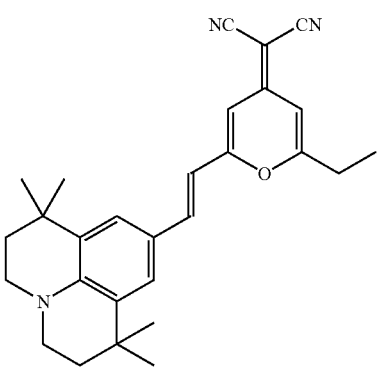

DCJTP
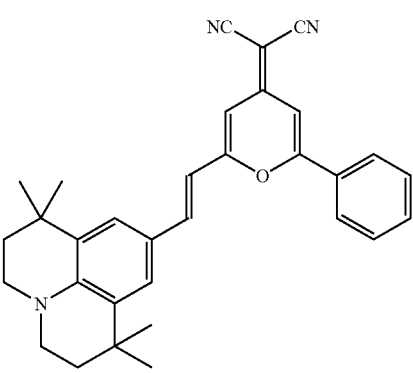

DCJTBz
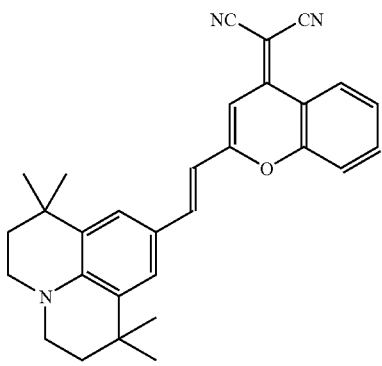

-continued

DCJTB
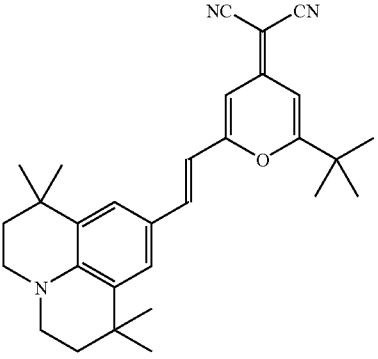

DCJTMes
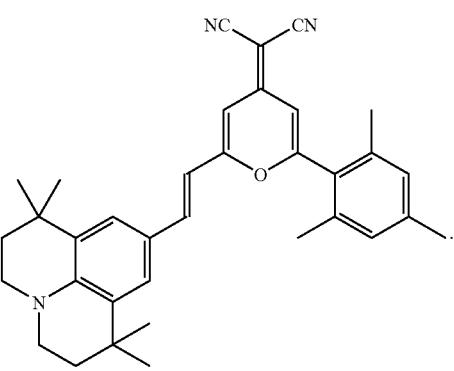

For red-emitting OLEDs, another preferred class of dopants of this invention comprises compounds having a periflanthene moiety:

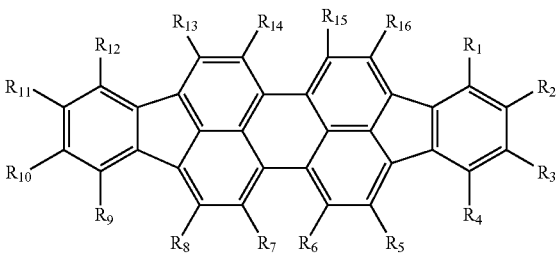

wherein:

substituents $R_1$ through $R_{16}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

These materials possess fluorescence efficiencies as high as unity in solutions and emit in the orange and red spectral region. One representative material of this class is:

Red 2

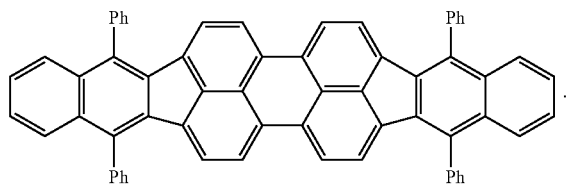

For green-emitting OLEDs, a class of fluorescent materials is useful as the dopants in the present invention, which includes compounds having a coumarin moiety:

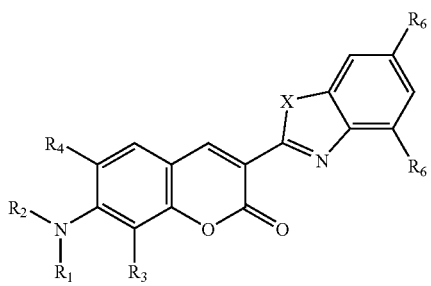

wherein:

X=S, O, or $NR_7$; $R_1$ and $R_2$ are individually alkyl of from 1 to 20 carbon atoms, aryl or carbocyclic systems; $R_3$ and $R_4$ are individually alkyl of from 1 to 10 carbon atoms, or a branched or unbranched 5 or 6 member substituent ring connecting with $R_1$ and $R_2$, respectively; $R_5$ and $R_6$ are individually alkyl of from 1 to 20 carbon atoms, which are branched or unbranched; and $R_7$ is any alkyl or aryl group.

These materials possess fluorescence efficiencies as high as unity in solutions. Representative materials of this class and their abbreviated names include:

C-545T

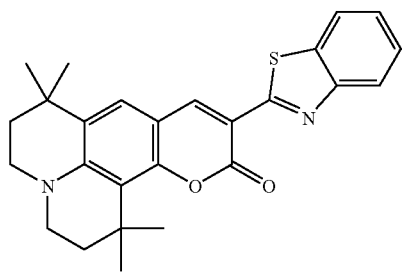

C-6

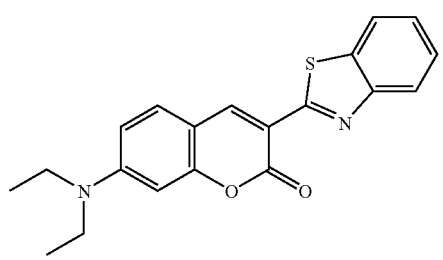

-continued

C-525T

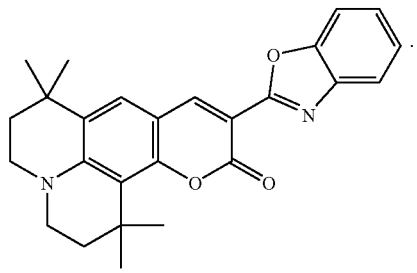

For green-emitting OLEDs, another class of fluorescent materials is useful as the dopants in the present invention, which includes compounds having a quinacridone moiety:

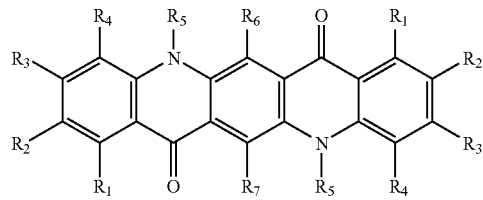

wherein:

substituents $R_1$ through $R_7$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_4$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_4$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

These materials possess fluorescence efficiencies as high as unity in solutions. Representative materials of this class and their abbreviated names include:

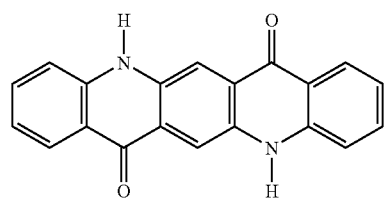

Quinacridone, QA

-continued

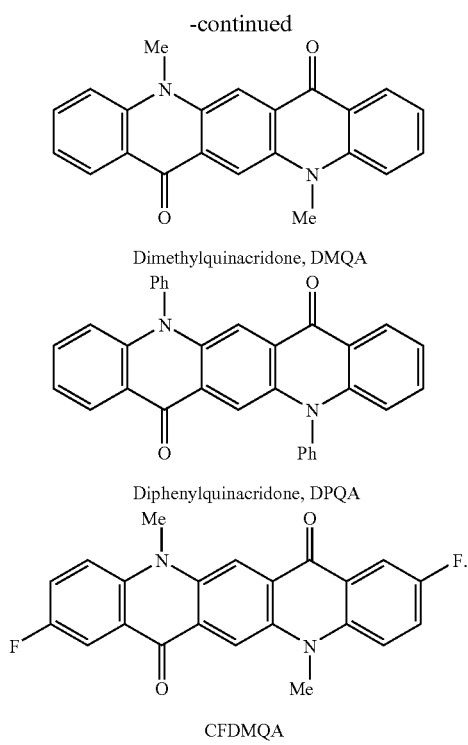

Dimethylquinacridone, DMQA

Diphenylquinacridone, DPQA

CFDMQA

For green, green-yellow, and yellow emitting OLEDs, another class of fluorescent materials is useful as the dopants in the present invention, which includes compounds having a DPMB (dipyridinomethene borate) moiety:

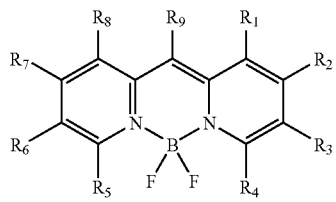

wherein:

substituents $R_1$ through $R_9$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_9$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_9$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

These materials possess fluorescence efficiencies as high as unity in solutions. Representative materials of this class include:

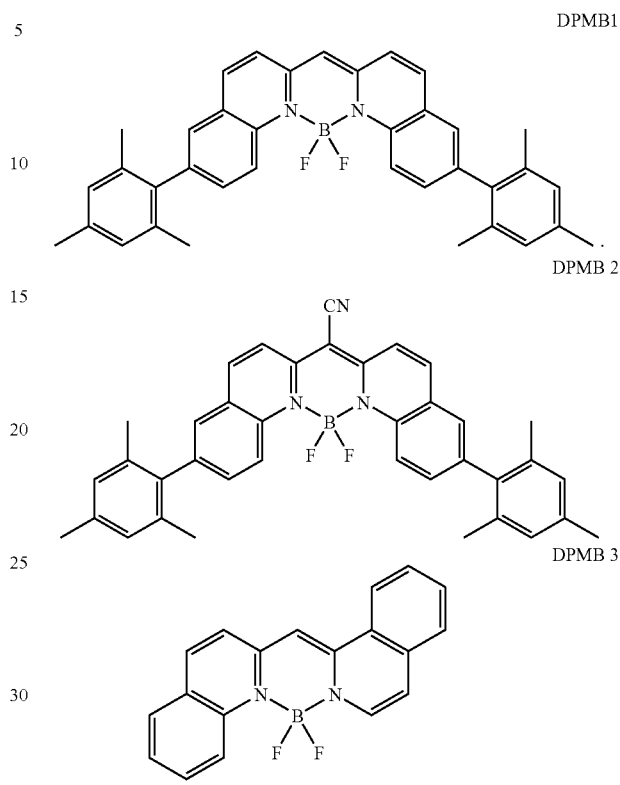

For yellow- and orange-emitting OLEDs, a preferred class of dopants for this invention includes compounds having an indenoperylene moiety:

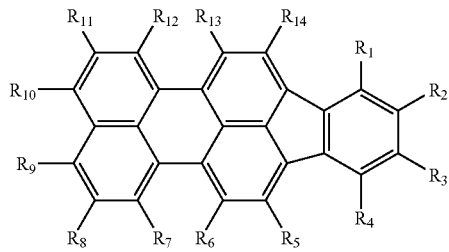

wherein:

substituents $R_1$ through $R_{14}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-

Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

These materials possess fluorescence efficiencies as high as unity in solutions. One representative material of this class is:

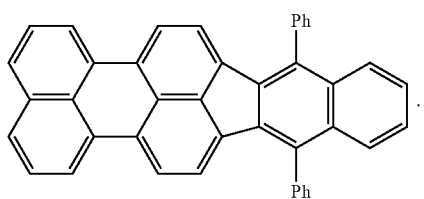

Yellow-green 2

For yellow- and orange-emitting OLEDs, another preferred class of dopants for this invention includes compounds having a naphthacene moiety:

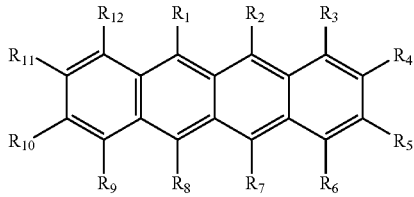

wherein:

substituents $R_1$ through $R_{12}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{12}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{12}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

These materials possess fluorescence efficiencies as high as unity in solutions and emit in the spectral region from greenish-yellow to red. Representative materials of this class and their abbreviated names include:

5,6,11,12-Tetraphenylnaphthacene (rubrene);
2,2'-[(6,11-diphenyl-5,12-naphthacenediyl)di-4,1-phenylene]bis(6-methylbenzothiazole) (Orange 2);
5,12-Bis(2-mesityl)-6,11-diphenyltetracene;
5,6,11,12-Tetrakis(2-naphthyl)tetracene;
10,10'-[(6,11-Diphenyl-5,12-naphthacenediyl)di-4,1-phenylene]bis[2,3,6,7-tetrahydro-1H,5H-benzothiazolo[5,6,7-ij]quinolizine;
5,6,13,14-Tetraphenylpentacene;
4,4'-(8,9-Dimethoxy-5,6,7,10,11,12-hexaphenyl-1,4-naphthacenediyl)bis[N,N-diphenylbenzenamine];
6,11-diphenyl-5,12-bis(4'-N,N-diphenylaminophenyl)naphthacene;
7,8,15,16-Tetraphenyl-benzo[a]pentacene; or
6,11-diphenyl-5,12-bis(4'-cyanophenyl)naphthacene.

For green-blue, blue-green, and blue-emitting OLEDs, a preferred class of dopants for this invention includes compounds having a substituted or unsubstituted BASB (bisaminostyrylbenzene) moiety:

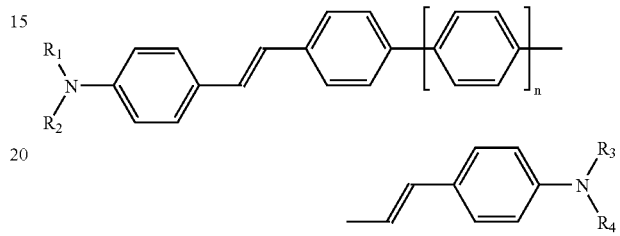

wherein:

each double bond can be either E or Z independently of the other double bond; substituents $R_1$ through $R_4$ are each individually and independently alkyl of from 1 to 24 carbon atoms, aryl, or substituted aryl of from 5 to 30 carbon atoms, heterocycle containing at least one nitrogen atom, or at least one oxygen atom, or at least one sulfur atom, or at least one boron atom, or at least one phosphorus atom, or at least one silicon atom, or any combination thereof; n is 0, 1, or 2; and substitution at other atoms is as previously described.

These materials possess fluorescence efficiencies as high as unity in solutions. Representative materials of this class include:

4-(Diphenylamino)-4'-[4-(diphenylamino)styryl]stilbene;
4-(Di-p-Tolylamino)-4'-[(di-p-tolylamino)styryl]stilbene (Blue-green 2);
4,4'-[(2,5-Dimethoxy-1,4-phenylene)di-2,1-ethenediyl]bis[N,N-bis(4-methylphenyl)benzenamine;
4,4'-(1,4-Naphthalenediyldi-2,1-ethenediyl)bis[N,N-bis(4-methyl-phenyl)benzenamine;
3,3'-(1,4-Phenylenedi-2,1-ethenediyl)bis[9-(4-ethylphenyl)-9H-carbazole;
4,4'-(1,4-Phenylenedi-2,1-ethenediyl)bis[N,N-diphenyl-1-naphthalenamine;
4,4'-[1,4-Phenylenebis(2-phenyl-2,1-ethenediyl)]bis[N,N-diphenyl-benzenamine];
4,4',4''-(1,2,4-Benzenetriyltri-2,1-ethenediyl)tris[N,N-diphenyl-benzenamine];
9,10-Bis[4-(di-p-tolylamino)styryl]anthracene; or
α,α'-(1,4-Phenylenedimethylidyne)bis[4-(diphenylamino)-1-naphthaleneacetonitrile.

Useful distyrylarylene derivatives are also described in U.S. Pat. No. 5,121,029.

For blue-emitting OLEDs, a preferred class of dopants for this invention includes compounds having a perylene moiety:

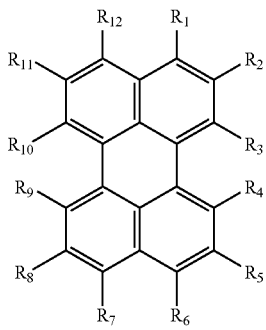

wherein:

substituents $R_1$ through $R_{12}$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{12}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{12}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

These materials possess fluorescence efficiencies as high as unity in solutions. Representative materials of this class include:
Perylene;
2,5,8,11-Tetra-tert-butylperylene (TBP);
2,8-Di-tert-Butylperylene;
Ovalene;
Dibenzo[b,ghi]perylene; or
Dibenzo[b,k]perylene.

For blue-emitting OLEDs, another preferred class of dopants for this invention includes compounds having a ADPMB (aza-DPMB) moiety:

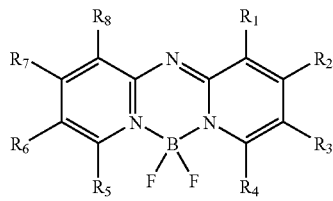

wherein:

substituents $R_1$ through $R_8$ are each individually hydrogen, fluoro, cyano, alkoxy, aryloxy, diarylamino, arylalkylamino, dialkylamino, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof, or any two adjacent $R_1$ through $R_8$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_8$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

These materials possess fluorescence efficiencies as high as unity in solutions. Representative materials of this class include:

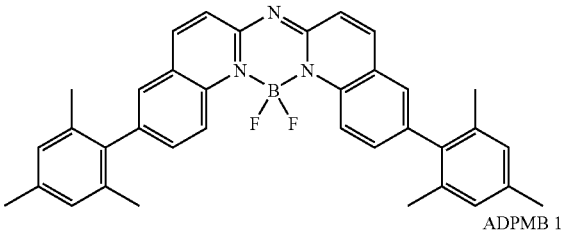

Blue 2

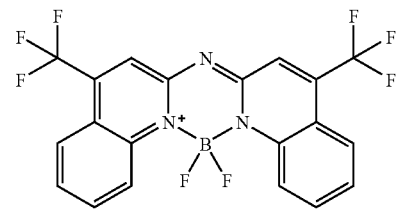

ADPMB 1

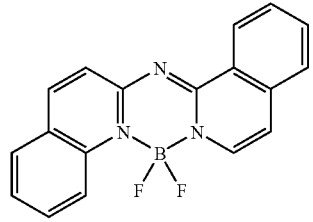

ADPMB 2

The composition of the luminescent layer of this invention is such that either the first host component or the second host component can constitute the largest volume fraction of the luminescent layer. The dopant usually constitutes the smallest volume fraction. The range for the first host component is from 1 to 99 volume % of the luminescent layer. The preferred range for the first host component is from 5 to 95% by volume. The range for the second host component is from 1 to 99 volume % of the luminescent layer. The preferred range for the second host component is from 5 to 95% by volume. The concentration range for the dopant is from 0.1% to 10% by volume. The preferred concentration range for the dopant is from 0.5% to 5% by volume. The thickness of the luminescent layer useful in this invention is between 50 Angstroms and 5000 Angstroms. A thickness in this range is sufficiently large to enable recombination of charge carriers and, therefore, electroluminescence to take place exclusively in this layer. A preferred range is between 100 Angstroms and 1000 Angstroms, where the overall OLED device performance parameters, including drive voltage, are optimal. Other host and emitting materials known to be of use include, but are not limited to, those disclosed in U.S. Pat. Nos. 4,768,292; 5,141,671; 5,150,006; 5,151,629; 5,405,709; 5,484,922; 5,593,788; 5,645,948; 5,683,823; 5,755,999; 5,928,802; 5,935,720; 5,935,721, and 6,020,078.

A useful method for forming the luminescent layer of the present invention is by vapor deposition in a vacuum chamber. This method is particularly useful for fabricating OLED devices, where the layer structure, including the organic layers, can be sequentially deposited on a substrate without significant interference among the layers. The thickness of each individual layer and its composition can be precisely controlled in the deposition process. To produce the desired composition of the luminescent layer, the rate of deposition for each component is independently controlled using a deposition rate monitor.

Another useful method for forming the luminescent layer of the present invention is by spin-coating or by ink-jet printing. This method is particularly useful for fabricating lower-cost OLED devices. Composition of the luminescent layer is determined by the concentration of each component in the solutions being coated.

When the desired electroluminescent light emission (EL) is viewed through anode, the anode should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode. For applications where EL emission is viewed only through the cathode, the transmissive characteristics of the anode are immaterial and any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable ways such as evaporation, sputtering, chemical vapor deposition, or electrochemical means. Anodes can be patterned using well known photolithographic processes. Optionally, anodes can be polished prior to application of other layers to reduce surface roughness so as to minimize shorts or enhance reflectivity.

When light emission is viewed solely through the anode, the cathode used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising the cathode and a thin electron-injection layer (EIL) in contact with an organic layer (e.g., an electron transporting layer (ETL)) which is capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in U.S. Pat. No. 5,677,572. Other useful cathode material sets include, but are not limited to, those disclosed in U.S. Pat. Nos. 5,059,861; 5,059,862; and 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. Nos. 4,885,211 and 5,247,190; JP 3,234, 963; U.S. Pat. Nos. 5,703,436; 5,608,287; 5,837,391; 5,677, 572; 5,776,622; 5,776,623; 5,714,838; 5,969,474; 5,739, 545; 5,981,306; 6,137,223; 6,140,763; and 6,172,459; EP 1 076 368; U.S. Pat. Nos. 6,278,236 and 6,284,393. Cathode materials are typically deposited by any suitable method such as evaporation, sputtering, or chemical vapor deposition. When needed, patterning can be achieved through many well known methods including, but not limited to, through-mask deposition, integral shadow masking as described in U.S. Pat. No. 5,276,380 and EP 0 732 868, laser ablation, and selective chemical vapor deposition.

Returning to FIG. 2, hole-transport layer 231 and electron-transport layer 233 provide the functions of transporting holes and electrons, respectively, to the luminescent layer 232. The use of these layers and their material compositions in OLED devices have been disclosed by Tang et al. in commonly assigned U.S. Pat. No. 4,769,292, the disclosure of which is herein incorporated by reference. The hole-transporting layer of the organic EL device contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al. U.S. Pat. No. 3,180,730. Other suitable triarylamines substituted with one or more vinyl radicals and/or comprising at least one active hydrogen containing group are disclosed by Brantley et al. U.S. Pat. Nos. 3,567, 450 and 3,658,520. A more preferred class of aromatic tertiary amines are those which include at least two aromatic tertiary amine moieties as described in U.S. Pat. No. 4,720, 432 and U.S. Pat. No. 5,061,569. A typical hole-transport layer includes the hole-transporting compounds such as N,N'-bis(1-naphthyl)-N,N'-diphenylbenzidine (NPB), N,N'-bis(1-naphthyl)-N,N'-bis(2-naphthyl)benzidine (TNB), and N,N'-bis(3-tolyl)-N,N'-diphenylbenzidine (TPD). Another class of useful hole-transporting materials includes polycyclic aromatic compounds as described in EP 1 009 041. Tertiary aromatic amines with more than two amine groups can be used including oligomeric materials. In addition, polymeric hole-transporting materials can be used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS.

Preferred thin film-forming materials for use in forming the electron-transporting layer of the organic EL devices of this invention are metal chelated oxinoid compounds, including chelates of oxine itself (also commonly referred to as 8-quinolinol or 8-hydroxyquinoline). Such compounds help to inject and transport electrons and exhibit both high levels of performance and are readily fabricated in the form of thin films. Exemplary of contemplated oxinoid compounds are those previously described.

Other electron-transporting materials include various butadiene derivatives as disclosed in U.S. Pat. No. 4,356,429 and various heterocyclic optical brighteners as described in U.S. Pat. No. 4,539,507. Benzazoles satisfying structural formula (G) are also useful electron transporting materials. Triazines are also known to be useful as electron transporting materials.

Returning to FIG. 3, hole-injection layer 331 and electron-injection layer 335 provide the functions of improving the hole-injection from the anode and electron-injection from the cathode 340, respectively. The use of a hole-injection layer in OLED devices has been disclosed by Van Slyke et al. in commonly assigned U.S. Pat. No. 4,720,432, the disclosure of which is herein incorporated by reference. Suitable materials for use in the hole-injecting layer include, but are not limited to, porphyrinic compounds as described in U.S. Pat. No. 4,720,432, plasma-deposited fluorocarbon polymers as described in U.S. Pat. No. 6,208,075, and some aromatic amines, for example, m-MTDATA (4,4',4''-tris[(3-methylphenyl)phenylamino]triphenylamine). Alternative hole-injecting materials reportedly useful in organic EL devices are described in EP 0 891 121 A1 and EP 1 029 909 A1. The use of an electron-injection layer has been disclosed by Hung et al. in commonly assigned U.S. Pat. No. 5,776,622, the disclosure of which is herein incorporated by reference.

The organic materials mentioned above are suitably deposited by any ways suitable for the form of the organic materials. In the case of small molecules, they are conveniently deposited through sublimation, but can be deposited by other ways such as from a solvent with an optional binder to improve film formation. If the material is a polymer, solvent deposition is usually preferred. The material to be deposited by sublimation can be vaporized from a sublimator "boat" often comprised of a tantalum material, e.g., as described in U.S. Pat. No. 6,237,529, or can be first coated onto a donor sheet and then sublimed in closer proximity to the substrate. Layers with a mixture of materials can utilize separate sublimator boats or the materials can be pre-mixed and coated from a single boat or donor sheet. Patterned deposition can be achieved using shadow masks, integral shadow masks (U.S. Pat. No. 5,294,870), spatially-defined thermal dye transfer from a donor sheet (U.S. Pat. Nos. 5,688,551; 5,851,709; and 6,066,357) and inkjet method (U.S. Pat. No. 6,066,357).

Most OLED devices are sensitive to moisture or oxygen, or both, so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as SiOx, Teflon, and alternating inorganic/polymeric layers are known in the art for encapsulation.

OLED devices of this invention can employ various well known optical effects in order to enhance its properties if desired. This includes optimizing layer thicknesses to yield maximum light transmission, providing dielectric mirror structures, replacing reflective electrodes with light-absorbing electrodes, providing anti glare or anti-reflection coatings over the display, providing a polarizing medium over the display, or providing colored, neutral density, or color conversion filters over the display. Filters, polarizers, and anti-glare or anti-reflection coatings can be specifically provided over the cover or as part of the cover.

The entire contents of the patents and other publications referred to in this specification are incorporated herein by reference.

Synthesis

Materials of the present invention can be prepared by methods commonly employed in the art. References to many of the benzenoid compounds can be found in E. J. Clar, "Polycyclic Hydrocarbons," v 1–2, New York, N.Y., Academic Press, 1964. There has been some confusion as to the structure of dibenzo[b,k]perylene prepared in the literature. A synthesis of this material is given below.

Dibenzo[b,k]perylene

To a stirred solution of 9-bromophenanthrene (50 g) in benzene (250 mL) was added solid aluminum chloride (50 g) gradually in portions. After the addition was complete, the mixture was heated at reflux for one hour, then cooled to ambient temperature. A slow addition of 2N HCl (250 mL) was then made (caution: exothermic). The resultant mixture was heated to reflux for an hour. Once cooled the mixture was filtered. The crude solid was washed with several portions of water and air-dried. The black solid (13.5 g) was placed in a soxhlet extractor and extracted with hot THF. The concentrated extracts were sublimed under a nitrogen flow at 300° C. and 640 mTorr to provide 1.2 g of dibenzo[b,k]perylene. The sample was pure by HPLC analysis (Keystone PAH, 5 micron, 100×3 mm).

WORKING EXAMPLES 1–10

Electroluminescence of Aggregates of Various PAH Compounds Containing at Least One Perylene Ring Structure OLED devices were prepared as follows. A glass substrate coated with about 850 Å transparent indium-tin-oxide (ITO) conductive layer was cleaned and dried using a commercial glass scrubber tool. The ITO surface was subsequently treated with an oxidative plasma to condition the surface as an anode. Over the ITO was deposited a 10 Å thick hole-injecting layer of fluorocarbon (CFx) by plasma-assisted deposition of $CHF_3$. The following layers were deposited in the following sequence by sublimation from heated crucible boats in a conventional vacuum deposition chamber under a vacuum of approximately $10^{-6}$ torr: (1) a hole-transport layer, 750 Å thick, including NPB, (2) a luminescent layer, 350 Å thick, including the first and second host components in certain ratio (indicated in Table 1) and not containing luminescent dopants, (3) an electron-transport layer, 350 Å thick, including $AlQ_3$, and (4) a cathode, approximately 2200 Å thick, including an alloy of magnesium and silver with a Mg:Ag volume ratio of about 10:1. Following that the devices were encapsulated in nitrogen atmosphere along with calcium sulfate as a desiccant.

The EL characteristics of these devices were evaluated using a constant current source and a photometer. The drive voltage, EL efficiency in cd/A and W/A, CIE coordinates, peak wavelength, $\lambda_{max}$, full spectral width at half-maximum, FWHM, and loss or gain in EL efficiency as current density, J, increases from 0.5 to 100 mA/cm$^2$, $\Delta$ cd/A vs J, at current densities ranging from relatively low, 0.5 mA/cm$^2$, to relatively high, 100 mA/cm$^2$, were measured. The EL efficiency in W/A, CIE coordinates, $\lambda_{max}$, FWHM, and description of the EL color and spectrum at 20 mA/cm$^2$ are given in Table 1.

As can be seen from Table 1 it is common for PAH compounds containing at least one perylene ring structure luminescent in their monomer state to form the aggregate states which are also luminescent in both polar and non-polar environments and electroluminescence for the aggregate states of these materials is readily observed. It further can be seen that the range of aggregate electroluminescence spans the whole visible spectrum and can be tuned by proper choice of materials.

FIGS. 4 through 9 illustrate photoluminescence and electroluminescence spectra for many of the Examples 1–10.

mately 10$^{-6}$ torr: (1) a hole-transport layer, either 750 or 1,500 Å thick, including NPB, (2) a luminescent layer, from 100 to 2,000 Å thick, including the 1$^{st}$ host component, 2$^{nd}$ host component, and most often a luminescent dopant, and (3) an electron-transport layer, from 0 to 500 Å thick, including AlQ$_3$. In some cases 1$^{st}$ host component was added also to the NPB hole-transporting layer, whole or part of it and with or without a luminescent dopant, or a part of the AlQ$_3$ electron-transporting layer, or both. In the cases of white OLEDs, structure utilizing two emissive layers was used where a part of the NPB hole-transporting layer doped with Orange 2 dopant served as a yellow-orange-emitting layer and TBADN doped with Blue-green 2 served as a blue-green-emitting layer.

The values for CIE coordinates and EL efficiency in W/A at mA/cm$^2$ and for operational stabilities expressed as values of T$_{90\%}$ and T$_{50\%}$ at RT-40 mA/cm$^2$ and 70° C.-20 mA/cm$^2$ for Working and Comparative Examples are shown in Table 2. Table 2 further lists the effects of addition of the 1$^{st}$ host component on the CIE coordinates, EL efficiency in W/A, and operational stability for Working Examples relative to the corresponding Comparative Examples.

TABLE 1

OLED data at 20 mA/cm$^2$: electroluminescence for aggregates of PAH compounds containing at least one perylene ring structure ($\lambda_{max}$ is peak wavelength, nm; FWHM is full spectral width at half-maximum, nm)

| Example # | 1$^{st}$ host component (1$^{st}$ hc)/2$^{nd}$ host component (2$^{nd}$ hc) | % 1$^{st}$ hc | Aggregate color/spectrum description | CIE$_x$ CIE$_y$ | $\lambda_{max}$/ FWHM nm | Efficiency W/A |
|---|---|---|---|---|---|---|
| 1 | Benzo[ghi]perylene/Alq | 40 | not readily visible in Alq | ~same as Alq | ~same as Alq | 1.3x higher than Alq |
| 2 | Benzo[ghi]perylene/TBADN | 25 | blue-green | ~0.200 0.300 | 480/~65 | 0.033 |
| 3 | Coronene/TBADN | 25 | blue-green; long tail into the red | ~0.300 0.400 | 510/~86 | ~0.012 |
| 4 | Perylene/Alq | 25 | green-yellowish | 0.420 0.550 | 540/88 | 0.018 |
| 5 | Perylene/TBADN | 25 | green; symmetric; pointy | 0.336 0.572 | 532/84 | 0.025 |
| 6 | 2,5,8,11-Tetra-tert-butylperylene/TBADN | 40 | blue-green; structured with long tail into the red | ~0.200 0.400 | 500/~65 | 0.017 |
| 7 | Peropyrene/TBADN | 25 | yellow; wide (DCJTB-like shape) | 0.504 0.487 | 576/108 | 0.027 |
| 8 | Dibenzo[b,k]perylene/Alq | 35 | not clearly visible in Alq | ~same as Alq | narrower than Alq | 1.2x higher than Alq |
| 9 | Dibenzo[b,k]perylene/TBADN | 10 | green, similar to perylene but bluer | 0.268 0.524 | 512/88 | 0.032 |
| 10 | Indeno[1,2,3-cd]perylene/Alq | 45 | red | ~0.660 0.330 | 640/~100 | 0.006 |

WORKING AND COMPARATIVE EXAMPLES 11–53

Stabilization Effects of Various Aggregate-Forming PAH Compounds Containing at Least One Perylene Ring Structure For thicknesses and concentrations of materials in multi-component layers of each device see Table 2. OLED devices were prepared similar to Examples 1–10. The following organic layers were deposited in the following sequence by sublimation from heated crucible boats in a conventional vacuum deposition chamber under a vacuum of approxi- Table 3 compiles various aging test data including aging at direct current conditions for Examples 11, 12, 13, 25, and 27-dibenzo[b,]-perylene as a first host component for red and green OLEDs.

As can be seen from Tables 2 and 3, working Examples 11 through 53 demonstrate from 50% to 10,000% improvements in lifetime relative to the respective Comparative Devices for a wide range of materials as 1$^{st}$ host components, various 2$^{nd}$ host components, various luminescent dopants of all colors, device configurations, compositions and thicknesses of emissive and charge-transporting layers, and testing conditions.

TABLE 2

OLED device data: red, yellow-orange, green, blue-green, blue, and white OLEDs.*,**
Dibenzo[b,k]perylene (DBP) as a first host component Red OLEDs
reference cells: 750 Å NPB | 300 Å Alq + 1-2% DCJTB | 300 Å Alq (no DBP)
sample cells: 750 Å NPB | varied thickness of Alq + 1-1.5% DCJTB + varied % of Dibenzo[b,k]perylene | 300 Å Alq

| 1st host component (1sthc) | 1st hc % | dopant % | EML thickness, Å | CIE$_x$, CIE$_y$ (ref.) | Effect on color | Efficiency, W/A (ref.) | Efficiency effect | Stability, AC @40 mA/cm² (ref.) T$_{90\%}$, h T$_{50\%}$, h | Stability, AC, 20 mA/cm² (ref.) T$_{90\%}$, h T$_{50\%}$, h | Stability effect at RT | Stability effect at 70° C. |
|---|---|---|---|---|---|---|---|---|---|---|---|
| Dibenzo[b,k]perylene | | | | | | | | | | | |

Example 11: 750 Å NPB | 400-252 Å Alq + 1-1.5% DCJTB + x% DBP | 300 Å Alq

| | 23 | 1.52 | 390 | 0.663, 0.334 (0.649, 0.347) | better | 0.041 (0.019) | +115% | 800(120) (1,000)* | 125(30) 3,000* (475) | 6.7x increase | 4-6x increase |
| | 31 | 1.38 | 435 | 0.664, 0.334 | better | 0.044 | +130% | 750 | 140 3,000*ii | 6.3x increase | 5-6x increase |

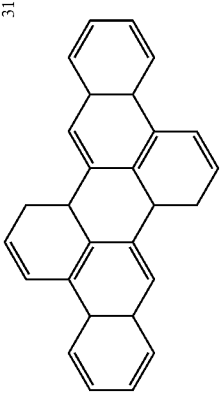

| | 38 | 1.26 | 480 | 0.664, 0.334 | better | 0.044 | +130% | 900 | 145 3,500* | 7.5x increase | 6-8x increase |
| | 43 | 1.14 | 525 | 0.660, 0.336 | better | 0.040 | +110% | 500 | 45 550 | 4.2x increase | none |

Example 12: 750 Å NPB | 400-525 Å Alq + 0.6-1.4% DCJTB + x% DBP | 300 Å Alq

| Dibenzo[b,k]perylene | 23 | 0.76 | 390 | 0.642, 0.354 | better | 0.045 | +120% | 540 | | ~5x increase | |
| | 31 | 0.69 | 435 | 0.645, 0.352 | better | 0.048 | +130% | 620 | | ~6x | |
| | 33 | 1.34 | 450 | 0.666, 0.332 | better | 0.042 | +100% | 640 | | ~6x increase | |
| | 38 | 0.63 | 480 | 0.645, 0.351 | better | 0.049 | +95% | 730 | | ~7x increase | |
| | 43 | 0.57 | 525 | 0.645, 0.351 | better | 0.051 | +120% | 720 | | ~7x increase | |

Example 13: 750 Å NPB | 450 Å Alq + 0.7% DCJTB + 35% DBP | 300 Å Alq

| Dibenzo[b,k]perylene | 35 | 0.67 | 450 | 0.640, 0.332 | better | 0.052 | +140% | 900* | | ~9x increase | |

Example 14: 750 Å NPB | 300 Å Alq + 1% DCJTB + x% DBP | 300 Å Alq

| Dibenzo[b,k]perylene | 20 | 1.0 | 308 | 0.623, 0.370 (0.610, 0.381) | better | 0.046 (0.031) | +50% | 1,100* (140) | 315 (60) 4,500* (800)* | 8x increase | 5.5x increase |
| | 30 | 1.0 | 303 | 0.630, 0.365 | better | 0.050 | +61% | 2,000* | 435 8,000* | ~14x increase | 10x increase |

Example 15: 750 Å NPB | 150-900 Å Alq + 1% DCJTB + 35% DBP | 500-0 Å Alq (reference cell has the same structure as sample cells but 300Å EML thickness)

| Dibenzo[b,k]perylene | 500 | 33 | 0.63 | 150 | 0.618, 0.376 | worse | 0.045 | −9% | 1,000* | 100 3,500 | none | 1.3–1.7x |

TABLE 2-continued

| ETL thickness, Å | | | | | | | | | | | |
|---|---|---|---|---|---|---|---|---|---|---|---|
| 400 | 33 | 0.62 | 305 | 0.630, 0.366 | small | 0.052 | ~0 | 900* | | none | decrease 1.1–1.3x |
| 300 | 33 | 0.64 | 450 | 0.635, 0.361 | ref. | 0.050 | ref. | 1,000* | | reference cell | decrease reference cell |
| 200 | 33 | 0.64 | 605 | 0.639, 0.357 | small | 0.047 | −6% | 1,200* | | ~1.2x increase | 1.1–1.6x increase |
| 100 | 33 | 0.63 | 755 | 0.640, 0.357 | small | 0.041 | −18% | 1,700* | | ~1.7x increase | 1.3–2.2x increase |
| 0 | 33 | 0.63 | 910 | 0.640, 0.357 | small | 0.037 | −26% | 2,500* | | ~2.5x increase | 2.3–2.7x increase (T80% ~1,500 h) (T80% ~2,000 h) |

Example 16: 750 Å NPB | 300–525 Å Rubrene-Alq 3:1 (as 2nd host component) + 0.5–1% DCJTB + x% DBP | 300 Å Alq

| | | | | | | | | | | | |
|---|---|---|---|---|---|---|---|---|---|---|---|
| 9 | 0.86 | 330 | 0.598, 0.394 (0.589, 0.402) | small | 0.029 (0.023) | +26% | | | 100 (80) | | |
| | | | 0.604, 0.389 | better | 0.032 | +39% | | | 200 | | ~1.3x increase |
| 17 | 0.83 | 360 | 0.610, 0.385 | better | 0.037 | +61% | | | 150 | | ~2.5x increase |
| 29 | 0.71 | 420 | 0.615, 0.382 | better | 0.043 | +87% | | | 300 | | ~2x increase |
| 38 | 0.63 | 480 | 0.617, 0.380 | better | 0.042 | +80% | | | 300 | | ~3.8x increase |
| 43 | 0.57 | 525 | | | | | | | | | ~3.8x increase |

Example 17: 750 Å NPB | 300 Å Alq + 1% DCJTB + x% DBP | 300 Å Alq
Dibenzo[b,k]perylene

| | | | | | | | | | | | |
|---|---|---|---|---|---|---|---|---|---|---|---|
| 20 | 1.0 | 303 | 0.627, 0.367 (0.608, 0.383) | better | 0.047 (0.037) | +27% | 380 (165) | ~5,000–10,000* (1,100)* | | 2–6x increase | |
| 30 | 1.0 | 305 | 0.632, 0.363 | better | 0.052 | +41% | 500 | ~5,000–10,000* | | 3–6x increase | |
| 40 | 1.0 | 304 | 0.635, 0.360 | better | 0.051 | +38% | 800 | | | ~5x increase | |
| 50 | 1.0 | 305 | 0.638, 0.357 | better | 0.049 | +32% | 700 | | | ~5x increase | |
| 60 | 1.0 | 300 | 0.643, 0.355 | better | 0.044 | +20% | 900 | | | ~6–8x increase | |

Example 18: 750 Å NPB | 200-900 Å Alq + 1% DCJTB + 35% DBP | 300 Å Alq (reference cell has 300 Å thick EML)
Dibenzo[b,k]perylene drive voltage

| | | | | | | | | | | | |
|---|---|---|---|---|---|---|---|---|---|---|---|
| 6.5 | 35 | 0.96 | 200 | 0.641, 0.354 | small | 0.035 | −15% | | | none | |
| 7.0 | 35 | 0.99 | 300 | 0.647, 0.349 | — | 0.041 | — | | | reference cell | |
| 7.5 | 35 | 1.04 | 400 | 0.651, 0.346 | small | 0.047 | +15% | | | 1.5x increase | |
| 8.4 | 35 | 1.01 | 500 | 0.652, 0.345 | small | 0.051 | +24% | | | 2x increase | |
| 10.0 | 35 | 1.04 | 700 | 0.656, 0.341 | better | 0.058 | +41% | | | 3x increase | |
| 11.7 | 35 | 1.04 | 900 | 0.660, 0.338 | better | 0.064 | +56% | | | 5x increase | |

TABLE 2-continued

Example 19: 750 Å NPB | 300 Å Rubrene (as the 2nd host component) + 0.5%
[structure: dibenzo[b,k]perylene with Ph substituents]
+ x% DBP | 300 Å Alq

| Dibenzo[b,k]perylene | | | | | | | | |
|---|---|---|---|---|---|---|---|---|
| | 10 | 0.44 | 305 | 0.639, 0.349 | better | 0.037 (0.033) | +12% | 850* (400) | 650 (350) | 2–4x increase | ~2x increase |
| | 20 | 0.44 | 303 | 0.644, 0.346 | better | 0.037 | +12% | 1,100* | 1,000 | 3–7x increase | ~3x increase |
| | 30 | 0.44 | 303 | 0.648, 0.342 | better | 0.038 | +15% | 1,400* | 2,000 | 3–10x increase | ~6x increase |
| | 40 | 0.44 | 300 | 0.655, 0.337 | better | 0.037 | +12% | 2,500* | 2,200 | 5–15x increase | ~7x increase |
| | 50 | 0.44 | 312 | 0.663, 0.332 | better | 0.033 | none | 4,000* | 3,500 | 8–30x increase | ~10x increase |

Example 20: EML is 300 Å Alq + 1.5% DCJTB; reference cell is 750 Å NPB |EML| 300 Å Alq

| 450 Å NPB|300 Å NPB + 1.5% DCJTB| EML|300 Å Alq | 0.25–8 | 0.9–1.0 | 375–405 | 0.640, 0.357 (0.637, 0.358) | ~0 | 0.022 (0.022) | none | 155 (125) | 1,400* (1,200)* | 100–400 (40) | 2x increase |
| 450 Å NPB|300 Å NPB + 1.5% DCJTB + 35% DBP|EML|300 Å Alq | | | | 0.642, 0.355 | small | 0.024 | +10% | 160 | 1,900* | | 2.5x increase |
| 450 Å NPB|300 Å NPB + 35% DBP|EML 300 Å Alq | | | | 0.626, 0.368¹ | worse | 0.023 | +5% | 200 | 2,200* | | 2.7x increase |
| 150 Å NPB|500 Å NPB + 35% DBP|100 Å NPB|EML|300 Å Alq | | | | 0.637, 0.359 | ~0 | 0.022 | none | 160 | 1,700* | | 2.4x increase |
| 750 Å NPB|EML|250 Å Alq + 35% DBP|50 Å Alq | | | | 0.635, 0.361 | ~0 | 0.020 | −10% | 135 | 1,500 | | 2.3x increase |

Example 21: 750 Å NPB | 375 Å Alq + 1% DCJTB + x% of mixture of dibenzo[b,k]perylene & dibenzo[b,h]perylene (as 1st host component) |375 Å Alq

| Mixture of dibenzo[b,k]- & dibenzo[b,h]perylene | | | | 0.626, 0.366 (0.620, 0.374) | small | 0.035 (0.038) | −8% | | | 1,200–5,000* (660) | 2–7x increase |
| 0.25% in Alq (no DCJTB) | 0.25 | 0 | 375 | 0.341, 0.548 | — | 0.020 | — | | | 1,300* | 2x increase |

Green OLEDs
reference cells: 750 Å NPB | 375 Å Alq + 0.5% C545T or DPQA (or CFDMQA) | 375 Å Alq (no DBP)
sample cells: 750 Å NPB | 450–575 Å Alq + 0.5% C545T or DPQA (or CFDMQA) + varied % of DBP | 375 Å Alq

| Example 22: 750 Å NPB | 450–575 Å Alq + 0.5% C545T + x% DBP | 375 Å Alq | | | | | | | | | | |
|---|---|---|---|---|---|---|---|---|---|---|---|
| Dibenzo[b,k]perylene | 17 | 0.47 | 450 | 0.289, 0.644 (0.287, 0.645) | ~0 | 0.059 (0.080) | −26% | 70 (5) | 5,000* (280) | | 18x increase |
| | 33 | 0.35 | 575 | 0.308, 0.635 | small | 0.060 | −25% | 95 | 14,500* | | 50x increase |

| Example 23: 750 Å NPB | 570 Å Alq + 0.2–0.4% C545T + 35% DBP | 375 Å Alq | | | | | | | | | | |
| Dibenzo[b,k]perylene | 35 | 0.18 | 571 | 0.334, 0.619 | — | 0.045 | — | 1,000* | 10,000–50,000* | | ~20–50x increase |
| | 35 | 0.42 | 570 | 0.340–0.369 0.611–0.584 | — | 0.042–0.032 | — | 1,000–1,300* | | | ~20–50x increase |

| Example 24: 750 Å NPB | 560 Å Alq + 0.35% C545T + 35% DBP | 375 Å Alq | | | | | | | | | | |
| Dibenzo[b,k]perylene | 33 | 0.36 | 565 | 0.328, 0.629 (0.285, 0.654) | strong | 0.055 (0067) | −18% | 900 | 20,000* | 300 (20) (350) | ~15x increase |

TABLE 2-continued

| | | | | | | | | | | |
|---|---|---|---|---|---|---|---|---|---|---|
| | 33 | 0.35 | 570 | 0.358–0.371 0.601–0.586 | — | 850–1,600 | 10,000–100,000* | 515 | ~10,000–20,000* | ~20–50x increase | ~20–50x increase |

Example 25: 750 Å NPB | 400–525 Å Alq + 0.3–0.45% DPQA + x% DBP | 375 Å Alq
Dibenzo[b,k]perylene

| | 9 | 0.44 | 412 | 0.312, 0.647 | ~0 | 700 (65) | (800) | 180–430 (35–75) | 5,000* (650) | 10.8x increase | 5–8x increase |
| | 17 | 0.41 | 450 | 0.326, 0.633 | small | 740 | 10,000–20,000* | 430–660 | 5,000–20,000* | ~13x increase | ~10–15x increase |
| | 29 | 0.35 | 525 | 0.343, 0.622 | strong | 1,000 | | 430 | | increase | increase |
| | 41 | 0.28 | 510 | 0.375, 0.597 | strong | 1,000 | | 340–920 | | | |

Example 26: 750 Å NPB | 375–410 Å Alq + 0.5% DPQA + x% DBP | 375 Å Alq
Dibenzo[b,k]perylene

| | 1 | 0.5 | 375 | 0.305, 0.642 (0.307, 0.649) | small | 230 (75) | 3,000* (800) | | | 3.4x increase | |
| | 2, 4 | 0.5 | 385 | 0.305, 0.643 | small | 350 | 4,000* | | | 5x increase | |
| | 7, 9 | 0.48 | 410 | 0.308, 0.643 | small | 540 | 7,000* | | | 8.8x increase | |

Example 27: 750 Å NPB | 450 Å Alq + 0.4% DPQA + 15% DBP | 375 Å Alq
Dibenzo[b,k]perylene

| | 16 | 0.38 | 454 | 0.328, 0.625 | — | 970 | 7,000–25,000* | | | ~9x increase | |

Example 28: 750 Å NPB | 375–400 Å Alq + 0.5% CFDMQA + x% of mixture of dibenzo[b,k]perylene & dibenzo[b,h]perylene | 375 Å Alq
Mixture of dibenzo[b,k]- &

| | 0.2 | 0.53 | 375 | 0.321, 0.629 (0.316, 0.633) | small | 80 (40) | 1,500* (850) | 50 (15) | 800 (400) | 1.4x increase | 2x increase |
| dibenzo[b,h]perylene | 1–8 | 0.53–0.49 | 380–405 | 0.330, 0.620 | small | 130 | 2,000* | 30–90 | 750–1,200* | 3–5x increase | ~3x increase |
| 0.25% in Alq (no CFDMQA) | 0.3 | 0 | 375 | 0.342, 0.547 | — | 150 | 3,000* | 50 | 2,000* | 4x increase | 5x increase |

Example 29: 750 Å NPB | 250 Å TBADN + 0.5% CFDMQA + x% mixture of dibenzo[b,k]perylene & dibenzo[b,h]perylene 350 Å Alq
Mixture of dibenzo[b,k]- &

| | 0.25–1 | 0.5 | 255 | 0.285, 0.570 (0.263, 0.568) | better | 50 (25) | 1,250* (550) | 20 (10) | 700 (270) | 2.3x increase | 2.6x increase |
| dibenzo[b,h]perylene | 4–8 | 0.5–0.47 | 265 | 0.315, 0.600 | red edge is up | 10 | 800* | 15 | 950 | 1.5x increase | 3.5x increase |

Example 30: 750 Å NPB | 375 Å Alq + 0 or 0.5% C545T + 0 or 33% DBP | 375 Å Alq
375 Å Alq, undoped

| | | | | 0.348, 0.563 | — | 100 | | | | undoped ref. cell | |
| 375 Å Alq + 33% DBP | | | | 0.368, 0.583 | small | 1,000* | | | | 10x increase | |
| 375 Å Alq + 33% DBP + 0.5% C545T | | | | 0.324, 0.628 | worse than 0% DBP | 1,000* | | | | ~10x increase | |
| 50 Å Alq + 33% DBP + 0.5% C545T| | | | 0.349, 0.603 | more host EL | 1,200* | | | | ~10x increase | |
| 325 Å Alq + 33% DBP | | | | 0.358, 0.593 | more | 950* | | | | ~10x increase | |
| 160 Å Alq + 33% DBP|50 Å Alq + 33% D BP + 0.5% C545T|60 Å Alq + 33% DBP | | | | | | | | | | | |
| 325 Å Alq + 33% DBP| | | | 0.361, 0.592 | more host EL | 1,300* | | | | ~10x increase | |
| 50 Å Alq + 33% DBP + 0.5% C545T | | | | | | | | | | | |

Blue OLEDs
Example 31: 750 Å NPB | 300–340 Å TBADN + 1.5% TBP + x% Dibenzo[b,k]perylene | 450 Å Alq
Dibenzo[b,k]perylene

| | 1 | 1.5 | 310 | 0.166, 0.297 (0.151, 0.260) | green-ish EL | 150 (90) | 700 (580) | | | 1.2x increase | |
| | 8 | 1.35 | 335 | 0.268, 0.524 | green | 525 | | | | 6x increase | |

TABLE 2-continued (Blue 2) + x% Dibenzo[b,k]perylene | 350 Å Alq

Example 32: 750 Å NPB | 200 Å TBADN + 0.75%
Dibenzo[b,k]perylene

| x% | | | | | | | | | |
|---|---|---|---|---|---|---|---|---|---|
| 0.35 | 0.73 | 200 | | small | 0.149, 0.136 (0.149, 0.126) | 0.053 (0.054) | none | 120 (80) | 900* (800)* | insignificant |
| 0.5 | 0.74 | 205 | | mild | 0.152, 0.153 | 0.053 | none | 130 | 1,000* | 1.25x increase |
| 1–4 | 0.69 | 210 | | strong | 0.162–0.225, 0.202–0.427 | 0.044–0.031 | −18 to −42% | 170–365 | 1,200–3,500* | 1.5–4.4x increase |

Example 33: 750 Å NPB | 200 Å TBADN + x% Dibenzo[b,k]perylene | 400 Å Alq (reference cell contains no DBP and 1% TBP)

| | | | | | | | | | |
|---|---|---|---|---|---|---|---|---|---|
| 0.5 | 0 | 200 | | better | 0.154, 0.154 (0.144, 0.179) | 0.044 (0.041) | +7% | 35 (120) | 700* (750)* | ~0 |
| 1 | 0 | 200 | | worse | 0.162, 0.201 | 0.041 | 0 | 45 | 1,000* | 1.3x increase |
| 2 | 0 | 200 | | greenish | 0.181, 0.292 | 0.035 | −14% | 55 | 2,000* | 2.7x increase |
| 4 | 0 | 200 | | blue-green | 0.208, 0.384 | 0.031 | −24% | 55 | ~5,000* | 6.7x increase |

Example 34: 750 Å NPB | 200 Å TBADN + 0.25% mixture of dibenzo[b,k]perylene & dibenzo[b,h]perylene | 350 Å Alq

| | | | | | | | | | |
|---|---|---|---|---|---|---|---|---|---|
| 0.3 | 0 | 250 | | | 0.154, 0.170 | 0.042 | — | 200 | 1,000* | 2x increase |

Mixture of dibenzo[b,k]- & dibenzo[b,h]perylene

Example 35: 1,500 Å NPB | 200 Å TBADN + 2.5% 4-(di-p-tolylamino)-4'-[(di-p-tolylamino)styryl]stilbene (Blue-green 2) + x% DBP | 350 Å Alq

| | | | | | | | | | |
|---|---|---|---|---|---|---|---|---|---|
| 0.55 | 2.4 | 210 | | small | 0.189, 0.372 (0.185, 0.365) | 0.073 (0.075) | ~0 | 600 (275) | | 2.5x increase |
| 0.88 | 2.4 | 210 | | small | 0.191, 0.372 | 0.071 | −5% | 800* | | 3x increase |
| 1.72 | 2.4 | 210 | | red edge increase | 0.201, 0.384 | 0.062 | −17% | 1,000* | | 4x increase |
| 4.20 | 2.3 | 215 | | dopant + aggregate EL | 0.234, 0.447 | 0.053 | −29% | 1,500* | | 5.5x increase |
| 9.33 | 2.2 | 225 | | aggregate EL | 0.295, 0.515 | 0.042 | −44% | 2,200* | | 7.10x increase |

Example 36: 1,500 Å NPB + x% DBP | EML is 200 Å TBADN + 2% 4-(di-p-tolylamino)-4'-[(di-p-tolylamino)styryl]stilbene (Blue-green 2) + 0.5% DBP | 200 Å Alq + xx% DBP + 150 Å Alq

| | | | | | | | | | |
|---|---|---|---|---|---|---|---|---|---|
| 1500 Å NPB + 1% DBP|EML| | | | | 0.187, 0.271 | 0.040 | — | 250 (150) | 1,500* | 1.7x increase |
| 200 Å Alq|150 Å Alq | | | | | | | | | | |
| 1500 Å NPB|EML| | | | | 0.174, 0.243 | 0.047 | — | 300 | | 2x increase |
| 200 Å Alq + 0.5% DBP|150 Å Alq | | | | | | | | | | |
| 1500 Å NPB|EML| | | | | 0.174, 0.249 | 0.045 | — | 300 | 1,500* | 2x increase |
| 200 Å Alq + 1.0% DBP|EML| | | | | | | | | | |
| 1500 Å NPB + 0.5% DBP|EML| | | | | 0.178, 0.255 | 0.035 | — | 550 | 2,500* | 4x increase |
| 200 Å Alq + 0.5% DBP|150 Å Alq | | | | | | | | | | |

TABLE 2-continued

Example 37: 1,300 Å NPB | 200 Å NPB + 2% (Orange 2) | 200 Å TBADN + 2% 4-(di-p-tolylamino)-4'-[(di-p-tolylamino)styryl]stilbene (Blue-green 2) + x% DBP | 350 Å Alq (DBP in blue-green EML)

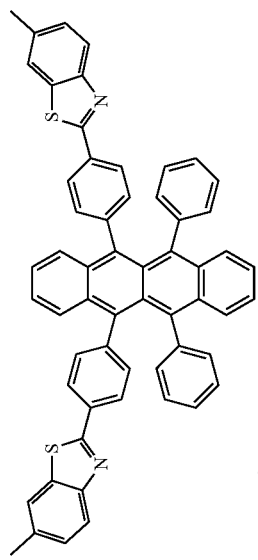

Dibenzo[b,k]perylene

| x | | | CIE | | T50 | |
|---|---|---|---|---|---|---|
| 0.5 | 2|2 | 200 | 0.257, 0.328 (0.252, 0.326) | small | 0.053 (0.051) | ~0 |
| 1.0 | 2|2 | 200 205 | 0.277, 0.367 | ~30% less blue | 0.050 | ~0 | 40 (35) | 550* (400)* | 1.4x increase |
| | | | | | | | 45 | 900* | 2.3x increase |
| 2.0 | 2|2 | 200 205 | 0.301, 0.425 | 1.7x less blue | 0.046 | −10% | 80 | 1,300 | 3.3x increase |
| 5.2 | 2|2 | 200 210 | 0.343, 0.504 | 2x less blue | 0.043 | −16% | 150 | 1,700* | 4.3x increase |
| 9.7 | 2|2 | 200 220 | 0.372, 0.540 | ~no blue | 0.044 | −14% | 200 | ~4,000* | 10x increase |

Example 38: 1,300 Å NPB | 200–250 Å NPB + 2% Orange 2 + x% DBP | 200 Å TBADN + 2% Blue-green 2 + 0.5% DBP | 200 Å Alq (DBP in yellow-orange EML)
Dibenzo[b,k]perylene

| 1 | 2.5|2.5 | 200 | 0.384, 0.387 (0.356, 0.374) | 15% less blue | 0.044 (0.045) | ~0 | 150 (30) | 2,500* (1,000)* | 2.5x increase |
| 2.5 | 2.5|2.5 | 210 200 | 0.439, 0.426 | 3x less blue | 0.044 | ~0 | 200 | 3,500* | 3.5x increase |
| 5 | 2.5|2.5 | 215 200 | 0.463, 0.442 | 4x less blue | 0.045 | none | 170 | ~5,200* | 5x increase |
| 10 | 2.4|2.5 | 225 200 | 0.487, 0.455 | 6.7x less blue | 0.046 | ~0 | 120 | ~7,000* | 7x increase |
| 25 | 2.0|2.5 | 255 200 | 0.452, 0.435 | 3.5x less blue | 0.045 | none | 100 | ~7,000* | ~7x increase) |

Example 39: 1,300 Å NPB | 200 Å NPB + 2% Orange 2 + x% DBP | 200 Å TBADN + 2% Blue-green 2 + 0.5% DBP | 200 Å Alq + xx% DBP < 150 Å Alq (DBP in yellow-orange EML, blue EML, and in ETL; reference cell has no DBP in any layer)

| 200 Å NPB + 0.5% DBP|200 Å TBADN + 2% OP31 + 0.5% DBP|350 Å Alq | | | 0.359, 0.378 (0.290, 0.334) | ~2x less blue/ more orange | 0.052 (0.048) | +8% | 135 (75) | 1,500* (800)* | 1.9x increase |
| 200 Å NPB + 1.0% DBP|200 Å TBADN + 2% OP31 + 0.5% DBP|350 Å Alq | | | 0.375, 0.391 | ~3.5x less blue | 0.052 | +8% | 150 | 2,000* | 2.5x increase |
| 200 Å NPB|200 Å TBADN + 2% OP31 + 0.5% DBP|200 Å Alq + 0.5% DBP|150 Å Alq | | | 0.322, 0.360 | ~1.6x less | 0.049 | ~0 | 115 | 1,600* | 2x increase |

TABLE 2-continued

| | | | | | | | |
|---|---|---|---|---|---|---|---|
| 200 Å NPB\|200 Å TBADN + 2% OP31 + 0.5% DBP\|200 Å Alq + 1.0% DBP\|150 Å Alq | | | 0.332, 0.358 | blue or more orange ~1.7x less blue or more orange | 0.047 | ~0 | 120 | 2,000* | 2.5x increase |
| 200 Å NPB + 1.0% DBP\|200 Å TBADN + 2% OP31 + 0.5% DBP\|200 Å Alq + 0.5% DBP\|150 Å Alq | | | 0.400, 0.421 | ~4x less blue | 0.045 | –6% | 180 | 2,500* | 3.1x increase |
| Example 40: 1,300 Å NPB \| 200 Å NPB + 2.5% Orange 2 \| 200 Å TBADN + 2.5% Blue-green 2 \| 200 Å Alq + x% DBP \| 150 Å Alq (DBP in ETL) | | | | | | | | | |
| Dibenzo[b,k]perylene | 1–5 | 2.5\|2.5 | 0.467, 0.436 (0.462, 0.433) | small; less blue | 0.039 (0.040) | ~0 | 140–300 (85) | ~5,500* (2,000)* | ~3x increase |
| | 10– 25 | 2.5\|2.5 | 0.457, 0.444 | more green | 0.037 | –8% | 200–360 | 6,000– 8,000* | ~4x increase |

Other perylene-containing materials as 1st host components

Red OLEDs
reference cells: 750 Å NPB \| 300–450 Å Alq + 1–2% DCJTB \| 300–375 Å Alq
sample cells: 750 Å NPB \| varied thickness of Alq + varied % of DCJTB + varied % of the 1st host component \| 300–375 Å Alq

| Example 41: 750 Å NPB \| 300–420 Å Alq + 0.7–1.0% DCJTB + x% Perylene \| 300 Å Alq | | | | | | | | | |
|---|---|---|---|---|---|---|---|---|---|
| Perylene | 9 | 0.9 | 0.636, 0.358 (0.621, 0.371) | better | 0.038 (0.026) | +46% | 190 (150) | 2,000* (1,300)* | 1.5x increase |
| | 17 | 0.83 | 0.642, 0.353 | better | 0.050 | +92% | 220 | 2,300* | 1.8x increase |
| | 23 | 0.76 | 0.642, 0.353 | better | 0.058 | +123% | 270 | 3,000* | 2.3x increase |
| | 29 | 0.71 | 0.641, 0.354 | better | 0.060 | +131% | | | |

Example 42: 750 Å NPB \| 390 Å Alq + 0 or 2% Perylene \| 300 Å Alq

| Perylene | 23 | 1.52 | 0.665, 0.332 (0.647, 0.349) | better | 0.052 (0.019) | +170% | 180 (165) | 1,800* (1,300)* | 1.4x increase |
| | 23 | 0 | 0.384, 0.562 (0.329, 0.543) | strong | 0.018 (0.020) | –10% | 900 (60) | 6,000* (1,100)* | 6–10x increase |

Example 43: 750 Å NPB \| 360–525 Å Alq + 0.5–1% DCJTB + x% Indeno[1,2,3-cd]perylene \| 300 Å Alq

| Indeno[1,2,3-cd]perylene | 17 | 0.83 | 360 | 0.651, 0.346 (0.625, 0.369) | better | 0.017 (0.025) | –32% | 105 (125) | ~2,500* (1,200)* | ~2x increase |
| | 23 | 0.76 | 390 | 0.653, 0.344 | better | 0.015 | –40% | 400 | | ~3x increase |

Example 44: 750 Å NPB \| 375 Å Alq + 1% DCJTB + x% Benzo[f]-4,7-diphenylindeno[1,2,3-cd]perylene \| 375 Å Alq

| Benzo[f]-4,7-diphenylindeno [1,2,3-cd]perylene | 31–43 | 0.69– 0.57 | 435– 525 | –0.659, 0.338 | better | 0.011– 0.006 | –56 to –76% | ~1,100* | | ~9x increase |
| | 10 | 1.0 | 380 | 0.613, 0.381 (0.593, 0.396) | better | 0.019 (0.044) | –57% | 200 (150) | | 1.5x increase |

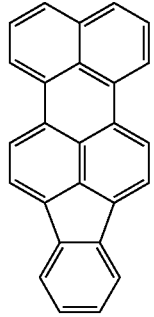

TABLE 2-continued

Ph / Ph
Coronene

| | 20–35 | 1.0 | 380 | 0.627, 0.367 | better | 0.021 | –52% | 1,000* | | 7x increase |

Example 45: 750 Å NPB | 390–525 Å Alq + 1–1.5% DCJTB + x% Coronene | 300 Å Alq

| | 50–75 | 1.0 | 380 | 0.613, 0.376 | better | 0.014–0.008 | –68 to –82% | 2,000* | | 15x increase |
| Coronene | 23–31 | 1.52 | 390–435 | 0.647, 0.349 (0.649, 0.348) | small | 0.022 (0.018) | +22% | 200 (90) | 2,250* (950)* | ~2.5x decrease |
| | 38–43 | 1.38 1.26–1.14 | 480–525 | 0.646, 0.351 | small | 0.022 | +22% | 300 | 5,000* | ~5x decrease |

Example 46: 750 Å NPB | 450–600 Å Alq + 1.3–1.7% DCJTB + x% TBP | 375 Å Alq

| TBP | 17 | 1.66 | 450 | 0.642, 0.353 (0.653, 0.344) | worse | 0.037 (0.022) | +70% | 190 (155) | 2,100* (1,300)* | 1.6x increase |
| | 29 | 1.42 | 525 | 0.634, 0.361 | worse | 0.043 | +95% | 130 | 1,700* | 1.3x increase |

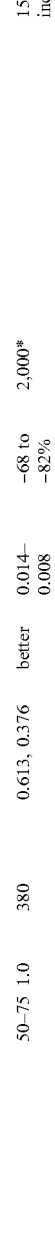

Green OLEDs
reference cells: 750 Å NPB | 375–450 Å Alq + 0.5% C545T or DPQA | 300–375 Å Alq
sample cells: 750 Å NPB | varied thickness of Alq + varied % of C545T or DPQA | 300–375 Å Alq
Example 47: 750 Å NPB | 490–650 Å Alq + 0.3–0.4% C545T + x% Benzo[ghi]perylene | 375 Å Alq

| Benzo[ghi]perylene | 38 | 1.26 | 600 | 0.622, 0.371 | worse | 0.047 | +114% | 80 | 1,200* | small |
| | 23 | 0.38 | 490 | 0.294, 0.641 (0.292, 0.638) | ~0 | 0.067 (0.059) | +14% | 60 (20) | 850* (490) | 1.7x increase |
| | 41 | 0.26 | 656 | 0.294, 0.636 | ~0 | 0.058 | ~0 | 100 | 1,300* | 2.7x increase |

Example 48: 750 Å NPB | 375 Å Alq + 0.5% DPQA + x% Perylene | 375 Å Alq

| Perylene | 2 | 0.5 | 385 | 0.311, 0.641 (0.311, 0.644) | ~0 | 0.033 (0.049) | –33% | 300 (85) | (800) | 3.5x increase |
| | | | | | | | | | 55–200 (35–90) | 1,700* (690) | 2.5x increase |
| | 4 | 0.5 | 393 | 0.312, 0.641 | ~0 | 0.033 | –33% | 390 | 70–210 | 1,800* | 4.6x increase 2.6x increase |
| | 7,9 | 0.45 | 405 | 0.315, 0.641 | ~0 | 0.036 | –28% | 500–1,000* | 90–260 | 2,100* | ~9x increase 3x increase |

TABLE 2-continued

| | | | | | | | | | |
|---|---|---|---|---|---|---|---|---|---|
| | 17 | 0.42 | 455 | 0.322, 0.640 | small | | 0.039 | −20% | 120–370 | 4,000* | 3–6x increase |

Example 49: 750 Å NPB | 375 Å Alq + 0.5% DPQA + x% TBP | 375 Å Alq

| TBP | | | | | | | | | |
|---|---|---|---|---|---|---|---|---|---|
| | 2 | 0.5 | 385 | 0.308, 0.638 (0.309, 0.646) | small | | 0.032 (0.044) | −27% | 125 (95) | 2,000* (900)* | 2.2x increase |
| | 5–10 | 0.5 | 390 | 0.304, 0.635 | small | | 0.027 | −39% | 55–95 | 1,500–2,000* | ~2x increase |
| | 20–50 | 0.5 | 370 | 0.289, 0.639 | bluer | | 0.030 | −32% | 60–75 | 1,500* | 1.7x increase |

BlueOLEDs reference cells: 750 Å NPB | 200–350 Å TBADN + 1–2% TBP or 0.75% (Blue 2) | 350–450 Å Alq

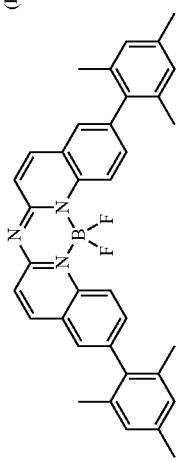

sample cells: 750 Å NPB | varied thickness of TBADN + varied % of TBP or Blue 2 + varied % of the 1st host component | 350–450 Å Alq Example 50: 750 Å NPB | 330–400 Å TBADN + 1.5–2% TBP + x% Benzo[ghi]perylene | 450 Å Alq

| Benzo[ghi]perylene | | | | | | | | | |
|---|---|---|---|---|---|---|---|---|---|
| | 9 | 1.8 | 335 | 0.151, 0.244 (0.145, 0.214) | worse than ref. | | 0.042 (0.044) | none | 60 (45) | 360 (280) | 1.3x increase |
| | 23 | 1.5 | 395 | 0.162, 0.281 | red edge is up | | 0.040 | −10% | 75 | 550 | 2x increase |

Example 51: 750 Å NPB | 330–400 Å TBADN + 1.5–2% TBP + x% Coronene | 450 Å Alq

| Coronene | | | | | | | | | |
|---|---|---|---|---|---|---|---|---|---|
| | 9 | 1.8 | 335 | 0.150, 0.247 (0.148, 0.235) | slightly worse | | 0.037 (0.039) | none | 100 (100) | 450 (450) | none |
| | 23 | 1.6 | 395 | 0.179, 0.319 | worse than ref. | | 0.030 | −23% | 100 | 570 | 1.4x increase |

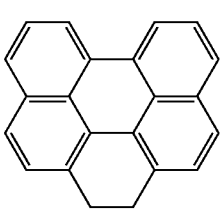

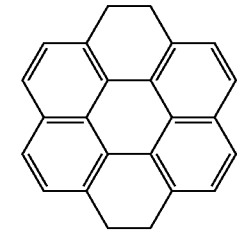

TABLE 2-continued

| | | | | | | | | |
|---|---|---|---|---|---|---|---|---|
| Example 52: 750 Å NPB | 330–400 Å TBADN + 1.5–2% TBP + x% Perylene | 450 Å Alq | | | | | | |
| Perylene | 9 | 1.8 | 330 | 0.269, 0.491 (0.146, 0.226) | green | 0.028 (0.043) | −35% | 220 (105) | 2x increase |
| | 23 | 1.6 | 395 | 0.336, 0.570 | green | 0.025 | −42% | 420 (700) | 4.3x increase |

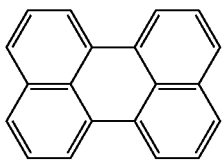

| | | | | | | | | |
|---|---|---|---|---|---|---|---|---|
| Example 53: 750 Å NPB | 330–400 Å TBADN + 1.5–2% TBP + x% Peropyrene | 450 Å Alq | | | | | | |
| Peropyrene | 9,23 | 1.8–1.6 | 330–400 | −0.480, −0.510 (0.150, 0.214) | yellow | 0.030 (0.038) | −20 to −30% | | 10x increase |

*fitted values; lifetimes were measured at average AC current density of 40 mA/cm² (0.5 ms forward bias at 80 mA/cm² alternating with the 0.5 ms of reverse bias of −14V) and at room temperature and the same way at 20 mA/cm² and 70° C.; fitted T$_{50\%}$'s are predicted values using stretched exponential fit procedure: the devices were run for some time, e.g. 250–2000 hours, after which time the aging was stopped and a plot of luminance versus time was fitted with stretched exponential function of the following form: $L_t = L_0 \times \exp(A \times t^B)$, where $L_t$ is luminance at time t, $L_0$ is initial luminance, A and B are empirical fit parameters, often found to be in the range of −0.011 and 0.59, respectively; half-lifetimes, T$_{50\%}$, were found by calculating time at which $L_t/L_0 = 0.5$; for 70° C.-20 mA/cm² stability data, T$_{50\%}$ sometimes represent actually measured values; 2x extrapolation works well, namely, fitted T$_{50\%}$ values usually agree very well with the actually measured ones when measured decay curve (used for fitting) reaches at least 75% of initial EL;
**the data are given at 20 mA/cm² unless noted otherwise; Alq = AlQ = AlQ$_3$; EML(emitting layer) = LEL(light emitting layer) = luminescent layer

TABLE 3

Device data: dibenzo[b,k]perylene (DBP) as a 1st host component for red and green OLEDs - various aging conditions.*,** reference cells: 750 Å NPB|300 Å Alq + 1–2% DCJTB|300 Å Alq
sample cells: 750 Å NPB|varied thickness of Alq + varied % of DCJTB + varied % of DBP|300 Å Alq

Example 11: 750 Å NPB|EML|300 Å Alq

| Cell<br>EML | | A<br>300 ÅAlq + 2%<br>DCJTB | B<br>300 ÅAlq +<br>2% DCJTB | C<br>390 ÅAlq + 1.5%<br>DCJTB + 23% DBP | D<br>435 ÅAlq + 1.4%<br>DCJTB + 31% DBP | E<br>480 ÅAlq + 1.3%<br>DCJTB + 38% DBP | F<br>525 ÅAlq + 1.1%<br>DCJTB + 43% DBP |
|---|---|---|---|---|---|---|---|
| AC-50% dc,<br>1 MHz, −14 V<br>rb, RT,<br>average J = 40<br>mA/cm²;<br>fresh cells | $T_{90\%}$, h<br>$T_{50\%}$, h<br>Effect | 120<br>1,000* | 120<br>1,000* | 800<br>6.7x increase | 750<br>6.3x increase | 900<br>7.5x increase | 500<br>4.2x increase |
| AC-50% dc,<br>1 MHz, −14 V<br>rb, 70° C.,<br>average J = 20<br>mA/cm²;<br>fresh cells | $T_{90\%}$, h<br>$T_{50\%}$, h<br>Effect | 30<br>475 | 30<br>475 | 125<br>3,000*<br>4–6x increase | 140<br>3,000*<br>5–6x increase | 145<br>3,500*<br>6–8x increase | 45<br>550<br>none |
| AC-50% dc,<br>1 MHz, −14 V<br>rb, 70° C.,<br>average J = 20<br>mA/cm²;<br>cells<br>annealed at<br>70° C. for<br>500 h | $T_{90\%}$, h<br>$T_{50\%}$, h<br>Effect | 40<br>500 | 40<br>500 | 190<br>3,000*<br>4–6x increase | 200<br>3,000*<br>5–6x increase | 245<br>4,000*<br>6–8x increase | 50<br>500<br>none |
| DC-<br>100% duty<br>cycle, RT, 40<br>mA/cm²;<br>cells<br>annealed at<br>70° C. for<br>850 h | $T_{90\%}$, h<br>$T_{50\%}$, h<br>Effect | 120<br>2,200* | 100<br>1,600 | 270<br>13,000*<br>7x increase | 250<br>13,000*<br>7x increase | 290<br>21,000*<br>11x increase | 220<br>10,000*<br>5x increase |

Example 12: 750 Å NPB|EML|300 Å Alq

| Cell<br>EML | | A<br>450 ÅAlq + 1.34%<br>DCJTB + 33% DBP | B<br>450 ÅAlq +<br>1.34%<br>DCJTB + 33%<br>DBP | C<br>390 ÅAlq + 0.76%<br>DCJTB + 23% DBP | D<br>435 ÅAlq + 0.69%<br>DCJTB + 31% DBP | E<br>480 ÅAlq + 0.63%<br>DCJTB + 38% DBP | F<br>525 ÅAlq + 0.57%<br>DCJTB + 43% DBP |
|---|---|---|---|---|---|---|---|
| AC-50% dc,<br>1 MHz, −14 V<br>rb, RT,<br>average J = 40<br>mA/cm²;<br>fresh cells | $T_{90\%}$, h<br>$T_{50\%}$, h<br>Effect | 640<br>~6x increase | 640<br>~6x increase | 540<br>~5x increase | 620<br>~6x increase | 730<br>~7x increase | 720<br>~7x increase |
| DC-<br>100% duty<br>cycle, RT, 40<br>mA/cm²;<br>fresh cells | $T_{90\%}$, h<br>$T_{50\%}$, h<br>Effect | 90<br>18,000*<br>~10x increase | | | | | |

Example 13: 750 Å NPB|EML|300 Å Alq (all 6 cells have the same geometry)

| Cell<br>EML | | A | B | C | D | E | F |
|---|---|---|---|---|---|---|---|
| | | | | 450 ÅAlq + 0.67% DCJTB + 33% DBP | | | |
| AC-50% dc,<br>1 MHz, −14 V<br>rb, RT,<br>average J = 40<br>mA/cm²;<br>fresh cells | $T_{90\%}$, h<br>$T_{50\%}$, h<br>Effect | | | 900*<br>~9x increase | | | |
| DC-<br>100% duty<br>cycle, RT, 40<br>mA/cm²;<br>fresh cells | $T_{90\%}$, h<br>$T_{50\%}$, h<br>Effect | 35<br>8,000*<br>~5–10x increase | | | | | | reference cells: 750 Å NPB|375 Å Alq + 0.3–0.5% DPQA|375 Å Alq
sample cells: 750 Å NPB|varied thickness of Alq + varied % of DPQA + varied % of DBP|375 Å Alq TABLE 3-continued Device data: dibenzo[b,k]perylene (DBP) as a 1st host component for red and green OLEDs - various aging conditions.*,**

Example 25: 750 Å NPB|EML|375 Å Alq

| Cell<br>EML | | A<br>375 ÅAlq + 0.56%<br>DPQA | B<br>375 ÅAlq +<br>0.53% DPQA | C<br>410 ÅAlq + 0.44%<br>DPQA + 9% DBP | D<br>450 ÅAlq + 0.41%<br>DPQA + 17% DBP | E<br>525 ÅAlq + 0.35%<br>DPQA + 29% DBP | F<br>610 ÅAlq + 0.28%<br>DPQA + 41% DBP |
|---|---|---|---|---|---|---|---|
| Ac-50% dc,<br>1 MHz, −14 V<br>rb, RT,<br>average J = 40<br>mA/cm²;<br>fresh cells | $T_{90\%}$, h<br>$T_{50\%}$, h<br>Effect | 65<br>800 | 65<br>800 | 700<br>11x increase | 740<br>10,000–25,000*<br>~11x increase | 1,000<br>~13x increase | 1,000<br>~13x increase |
| AC-50% dc,<br>1 MHz, −14 V<br>rb, 70° C.,<br>average J = 20<br>mA/cm²;<br>fresh cells | $T_{90\%}$, h<br>$T_{50\%}$, h<br>Effect | 35<br>650 | 35<br>650 | 180<br>5,000*<br>~8x increase | 430<br>5,000–20,000* | 430<br>~15x increase | 340 |
| AC-50% dc,<br>1 MHz, −14 V<br>rb, 70° C.,<br>average J = 20<br>mA/cm²;<br>cells<br>annealed at<br>70° C. for<br>500 h | $T_{90\%}$, h<br>$T_{50\%}$, h<br>Effect | 75<br>700 | 75<br>700 | 430<br>3,000*<br>4.5x increase | 660 | 1,000*<br>5,000–10,000*<br>~7x increase | 920* |
| DC-<br>100% duty<br>cycle, RT, 40<br>mA/cm²;<br>cells<br>annealed at<br>70° C. for<br>850 h | $T_{90\%}$, h<br>$T_{50\%}$, h<br>Effect | 25<br>1,300 | 20<br>1,200 | 125<br>11,000*<br>9x increase | 110<br>13,000*<br>10.5x increase | 80<br>17,000*<br>14x increase | 70<br>14,000*<br>11x increase |

Example 27: 750 Å NPB|EML|375 Å Alq

| Cell<br>EML | | A | B | C | D<br>450 ÅAlq + 0.38% DPQA + 16% DBP | E | F |
|---|---|---|---|---|---|---|---|
| AC-50% dc,<br>1 MHz, −14 V<br>rb, RT,<br>average J = 40<br>mA/cm²;<br>fresh cells | $T_{90\%}$, h<br>$T_{50\%}$, h<br>Effect | | | | 970*<br>7,000–25,000*<br>~9x increase | | |
| DC-<br>100% duty<br>cycle, RT, 40<br>mA/cm²;<br>fresh cells | $T_{90\%}$, h<br>$T_{50\%}$, h<br>Effect | 15<br>10,000*<br>~10x increase | | | | | |

*fitted values; lifetimes were measured at average AC current density of 40 mA/cm² (0.5 ms forward bias at 80 mA/cm² alternating with the 0.5 ms of reverse bias of −14 V) and at room temperature and the same way at 20 mA/cm² and 70° C.; fitted $T_{50\%}$'s are predicted values using stretched exponential fit procedure: the devices were run for some time, e.g. 250–1000 hours, after which time the aging was stopped and a plot of luminance versus time was fitted with stretched exponential function of the following form: $L_t = L_0 \times \exp(A \times t^B)$, where $L_t$ is luminance at time t, $L_0$ is initial luminance, A and B are empirical fit parameters, found to be in the range of −0.011 and 0.59, respectively; half-lifetimes, $T_{50\%}$, were found by calculating time at which $L_t/L_0 = 0.5$; for 60–80° C.-20 mA/cm² stability data, $T_{50\%}$ sometimes represent actually measured values; 2x extrapolation works well: that is, fitted $T_{50\%}$ values usually agree very well with the actually measured ones when measured decay curve (used for fitting) reaches at least 75% of initial EL;
**the data are given at 20 mA/cm² unless noted otherwise;
OC—open circuit;
DC—direct current;
dc—duty cycle;
rb—reverse bias;
RT—room temperature.

The invention has been described in detail with particular reference to certain preferred embodiments thereof, but it will be understood that variations and modifications can be effected within the spirit and scope of the invention.

PARTS LIST 10 electrical conductors
100 OLED device
110 substrate
120 anode
130 EL medium
140 cathode
200 OLED device
210 substrate
220 anode 230 EL medium
231 hole-transport layer
232 luminescent layer
233 electron-transport layer
240 cathode
300 OLED device
310 substrate
320 anode
330 EL medium
331 hole-injection layer
332 hole-transport layer
333 luminescent layer
334 electron-transport layer
335 electron-injection layer
340 cathode

What is claimed is:

1. An organic light emitting device, comprising:
a) a substrate;
b) an anode and a cathode disposed over the substrate;
c) a luminescent layer disposed between the anode and the cathode wherein the luminescent layer includes a host and at least one dopant;
wherein the host of the luminescent layer includes a solid organic material comprising a mixture of at least two components wherein:
i) the first component of the mixture is an organic compound containing at least one perylene carbocyclic ring structure or at least one mono-aza-perylene or poly-aza-perylene ring structure that transports either electrons or holes or both and forms both a monomer state and an aggregate state in said device, the aggregate state being either in a ground electronic state or in an excited electronic state, the ground electronic state and the excited electronic state having a different absorption or emission spectrum or both relative to the absorption or emission spectrum or both of the monomer state, respectively, or the first component of the mixture is an organic compound containing at least one perylene carbocyclic ring structure or at least one mono-aza-perylene or poly-aza-perylene ring structure that forms an aggregate state in said device the presence of which results in a quantum yield of luminescence of the monomer state that differs from the quantum yield of luminescence of the monomer state in the absence of the aggregate state, and wherein the first component is not a diarylamino-, arylalkylamino-, or dialkylamino-substituted perylene; and
ii) the second component of the mixture is an organic compound that mixes with the first host component to form a continuous and substantially pin-hole-free layer; and
wherein the host transfers electronic excitation energy to the dopant and the dopant emits light.

2. The organic light emitting device of claim 1 wherein the aggregate state is a dimer in either ground electronic state or excited electronic state.

3. The organic light emitting device of claim 1 wherein the aggregate state is crystalline.

4. The organic light emitting device of claim 3 wherein the aggregate state is a microcrystalline or nanocrystalline domain.

5. The organic light emitting device of claim 1 wherein the first component is an organic compound that is nonpolar.

6. The organic light emitting device of claim 1 wherein the first component is an organic compound that includes a benzenoid hydrocarbon.

7. The organic light emitting device of claim 1 wherein the first component is an organic compound that includes a heterocycle.

8. The organic light emitting device of claim 1 wherein the second component is an organic compound that is more polar than the first component.

9. The organic light emitting device of claim 1 wherein the first component is an organic compound having an energy gap greater than 1.5 electron volts.

10. The organic light emitting device of claim 1 wherein the second component is an organic compound having an energy gap greater than 1.5 electron volts.

11. The organic light emitting device of claim 1 wherein the first component constitutes at least 1 volume % of the luminescent layer.

12. The organic light emitting device of claim 1 wherein the second component constitutes at least 1 volume % of the luminescent layer.

13. The organic light emitting device of claim 1 wherein the dopant has an energy gap less than or equal to those of the first component and the second component.

14. The organic light emitting device of claim 1 wherein the dopant is a fluorescent dye.

15. The organic light emitting device of claim 1 wherein the dopant is a phosphorescent dye.

16. The organic light emitting device of claim 1 wherein the dopant concentration in the luminescent layer is a range of 0.1% to 10% by volume.

17. The organic light emitting device of claim 1 wherein the first component is a substituted or unsubstituted perylene.

18. The organic light emitting device of claim 1 wherein the first component is a substituted or unsubstituted benzoperylene.

19. The organic light emitting device of claim 1 wherein the first component is a substituted or unsubstituted naphthoperylene.

20. The organic light emitting device of claim 1 wherein the first component is a substituted or unsubstituted dibenzoperylene.

21. The organic light emitting device of claim 1 wherein the first component is a substituted or unsubstituted tribenzoperylene.

22. The organic light emitting device of claim 1 wherein the first component is a substituted or unsubstituted tetrabenzoperylene.

23. The organic light emitting device of claim 1 wherein the first component is a substituted or unsubstituted dibenzo [b,k]perylene.

24. The organic light emitting device of claim 1 wherein the first component is a substituted or unsubstituted dinaphthoperylene.

25. The organic light emitting device of claim 1 wherein the first component is a substituted or unsubstituted tribenzo [b,ghi,k]perylene.

26. The organic light emitting device of claim 1 wherein the first component is a substituted or unsubstituted benzo [ghi]perylene.

27. The organic light emitting device of claim 1 wherein the first component is a substituted or unsubstituted coronene.

28. The organic light emitting device of claim 1 wherein the first component is a substituted or unsubstituted dibenzo [cd,lm]perylene (peropyrene).

29. The organic light emitting device of claim 1 wherein the first component is a substituted or unsubstituted tribenzo [b,n,pqr]perylene.

30. The organic light emitting device of claim 1 wherein the first component is a substituted or unsubstituted ovalene.

31. The organic light emitting device of claim 1 wherein the first component is a substituted or unsubstituted phenanthroperylene.

32. The organic light emitting device of claim 1 wherein the first component is a substituted or unsubstituted pyrenoperylene.

33. The organic light emitting device of claim 1 wherein the first component is a substituted or unsubstituted benzo[a]coronene.

34. The organic light emitting device of claim 1 wherein the first component is a substituted or unsubstituted dibenzocoronene.

35. The organic light emitting device of claim 1 wherein the first component is a substituted or unsubstituted tribenzocoronene.

36. The organic light emitting device of claim 1 wherein the first component is a substituted or unsubstituted tetrabenzocoronene.

37. The organic light emitting device of claim 1 wherein the first component is a substituted or unsubstituted hexabenzocoronene.

38. The organic light emitting device of claim 1 wherein the first component is a substituted or unsubstituted naphthocoronene.

39. The organic light emitting device of claim 1 wherein the first component is a substituted or unsubstituted dinaphthocoronene.

40. The organic light emitting device of claim 1 wherein the first component is a substituted or unsubstituted triphenylenoperylene.

41. The organic light emitting device of claim 1 wherein the first component is a substituted or unsubstituted peryloperylene.

42. The organic light emitting device of claim 1 wherein the first component is a substituted or unsubstituted hexa-peri-benzocoronene (hexabenzo[bc,ef,hi,kl,no,qr]coronene).

43. The organic light emitting device of claim 1 wherein the first component is a substituted or unsubstituted benzoovalene.

44. The organic light emitting device of claim 1 wherein the first component is a substituted or unsubstituted dibenzo[b,pqr]perylene.

45. The organic light emitting device of claim 1 wherein the first component is a substituted or unsubstituted dibenzo[ij,rst]phenanthro-[9,10,1,2-defg]pentaphene.

46. The organic light emitting device of claim 1 wherein the first component is a PAH compound that can be drawn using only fully aromatic benzene rings so as to form graphite-like segments or a derivative thereof.

47. The organic light emitting device of claim 1 wherein the first component includes a benzenoid hydrocarbon or a derivative thereof substituted with a donor or an acceptor moiety or both.

48. The organic light emitting device of claim 1 wherein the second component includes a benzenoid hydrocarbon or a derivative thereof substituted with a donor or an acceptor moiety or both.

49. The organic light emitting device of claim 1 wherein the second component includes an oxinoid compound.

50. The organic light emitting device of claim 49 wherein the second component includes $AlQ_3$.

51. The organic light emitting device of claim 1 wherein the second component includes a substituted or unsubstituted anthracene moiety.

52. The organic light emitting device of claim 51 wherein the second component is selected from:
2-(1,1-dimethylethyl)-9,10-bis(2-naphthalenyl)anthracene (TBADN);
9,10-bis(2-naphthalenyl)anthracene (ADN);
9,10-bis(1-naphthalenyl)anthracene;
9,10-Bis[4-(2,2-diphenylethenyl)phenyl]anthracene;
9,10-Bis([1,1':3',1''-terphenyl]-5'-yl)anthracene;
9,9'-Bianthracene;
10,10'-Diphenyl-9,9'-bianthracene;
10,10'-Bis([1,1':3',1''-terphenyl]-5'-yl)-9,9'-bianthracene;
2,2'-Bianthracene;
9,9',10,10'-Tetraphenyl-2,2'-bianthracene;
9,10-Bis(2-phenylethenyl)anthracene; or
9-Phenyl-10-(phenylethynyl)anthracene.

53. The organic light emitting device of claim 1 wherein the second component includes an amine moiety.

54. The organic light emitting device of claim 53 wherein the second component is selected from:
N,N'-Bis(N'',N''-diphenylaminonaphthalen-5-yl)-N,N'-diphenyl-1,5-diaminonaphthalene (CAS 503624-47-3);
1,1-Bis(4-di-p-tolylaminophenyl)-4-phenylcyclohexane;
1,1-Bis(4-di-p-tolylaminophenyl)cyclohexane;
1,5-Bis[N-(2-naphthyl)-N-phenylamino]naphthalene;
1,5-Bis[N-(1-naphthyl)-N-phenylamino]naphthalene;
2,6-Bis(di-p-tolylamino)naphthalene;
2,6-Bis[di-(1-naphthyl)amino]naphthalene;
2,6-Bis[N-(1-naphthyl)-N-(2-naphthyl)amino]naphthalene;
2,6-Bis[N,N-di(2-naphthyl)amine]fluorene;
4-(di-p-tolylamino)-4'-[4-(di-p-tolylamino)-styryl]stilbene;
4,4''-Bis[N-(1-anthryl)-N-phenylamino]-p-terphenyl;
4,4''-Bis[N-(1-naphthyl)-N-phenylamino]p-terphenyl;
4,4',4''-tris[(3-methylphenyl)phenylamino]triphenylamine;
4,4'-Bis[N-(1-naphthyl)-N-(2-naphthyl)amino]biphenyl (TNB);
4,4'-Bis[N-(3-methylphenyl)-N-phenylamino]biphenyl (TPD);
4,4'-Bis(diphenylamino)quadriphenyl;
4,4'-Bis[N-(1-coronenyl)-N-phenylamino]biphenyl;
4,4'-Bis[N-(1-naphthyl)-N-phenylamino]biphenyl (NPB);
4,4'-Bis[N-(2-naphthacenyl)-N-phenylamino]biphenyl;
4,4'-Bis[N-(2-naphthyl)-N-phenylamino]biphenyl;
4,4'-Bis[N-(2-perylenyl)-N-phenylamino]biphenyl;
4,4'-Bis[N-(2-phenanthryl)-N-phenylamino]biphenyl;
4,4'-Bis[N-(2-pyrenyl)-N-phenylamino]biphenyl;
4,4'-Bis[N-(3-acenaphthenyl)-N-phenylamino]biphenyl;
4,4'-Bis[N-(8-fluoranthenyl)-N-phenylamino]biphenyl;
4,4'-Bis[N-(9-anthryl)-N-phenylamino]biphenyl;
4,4'-Bis[N-phenyl-N-(2-pyrenyl)amino]biphenyl;
4,4'-Bis {N-phenyl-N-[4-(1-naphthyl)-phenyl]amino}biphenyl;
Bis(4-dimethylamino-2-methylphenyl)-phenylmethane;
N,N,N',N'-Tetra(2-naphthyl)-4,4''-diamino-p-terphenyl;
N,N,N',N'-Tetraphenyl-4,4'-diaminobiphenyl;
N,N,N',N'-Tetra-p-tolyl-4-4'-diaminobiphenyl;
N,N,N',N'-tetra-1-naphthyl-4,4'-diaminobiphenyl;
N,N,N-Tri(p-tolyl)amine;
N,N'-di-1-naphthalenyl-N,N'-diphenyl-4,4'-diaminobiphenyl; or
N-Phenylcarbazole.

55. The organic light emitting device of claim 1 wherein the second component includes a substituted or unsubstituted fluorene moiety.

56. The organic light emitting device of claim 55 wherein the second component is selected from:
- 2,2',7,7'-Tetraphenyl-9,9'-spirobi[9H-fluorene];
- 2,2',7,7'-Tetra-2-phenanthrenyl-9,9'-spirobi[9H-fluorene];
- 2,2'-Bis(4-N,N-diphenylaminophenyl)-9,9'-spirobi[9H-fluorene](CAS 503307-40-2);
- 4'-Phenyl-spiro[fluorene-9,6'-[6H]indeno[1,2-j]fluoranthene];
- 2,3,4-Triphenyl-9,9'-spirobifluorene;
- 11,11'-Spirobi[11H-benzo[b]fluorene];
- 9,9'-Spirobi[9H-fluorene]-2,2'-diamine;
- 9,9'-Spirobi[9H-fluorene]-2,2'-dicarbonitrile;
- 2',7'-Bis([1,1'-biphenyl]-4-yl)-N,N,N',N'-tetraphenyl-9,9'-spirobi[9H-fluorene]-2,7-diamine;
- 9,9,9',9',9'',9''-Hexaphenyl-2,2':7',2''-ter-9H-fluorene;
- 2,7-Bis([1,1'-biphenyl]-4-yl)-9,9'-spirobi[9H-fluorene];
- 2,2',7,7'-tetra-2-Naphthalenyl-9,9'-spirobi[9H-fluorene]; or
- 9,9'-[(2,7-Diphenyl-9H-fluoren-9-ylidene)di-4,1-phenylene]bis-anthracene.

57. The organic light emitting device of claim 1 wherein the second component includes a substituted or unsubstituted naphthacene moiety.

58. The organic light emitting device of claim 57 wherein the second component is selected from:
- 5,6,11,12-Tetraphenylnaphthacene (rubrene);
- 5,12-Bis(2-naphthyl)-6,11-diphenyltetracene;
- 5,12-Bis(2-mesityl)-6,11-diphenyltetracene;
- 5,12-Bis(1-naphthyl)-6,11-diphenyltetracene;
- 5,6,11,12-Tetrakis(2-naphthyl)tetracene;
- 10,10'-[(6,11-Diphenyl-5,12-naphthacenediyl)di-4,1-phenylene]bis[2,3,6,7-tetrahydro-1H,5H-benzothiazolo[5,6,7-ij]quinolizine;
- 9,10,15,16-Tetraphenyl-dibenzo[a,c]naphthacene;
- 5,6,13,14-Tetraphenylpentacene;
- 4,4'-(8,9-Dimethyl-5,6,7,10,11,12-hexaphenyl-1,4-naphthacenediyl)bis-benzonitrile;
- 4,4'-(8,9-Dimethoxy-5,6,7,10,11,12-hexaphenyl-1,4-naphthacenediyl)bis[N,N-diphenylbenzenamine];
- 1,2,3,5,6,11,12-Heptaphenylnaphthacene;
- 1,4,5,6,7,10,11,12-Octaphenylnaphthacene;
- 6,11-diphenyl-5,12-bis(4'-N,N-diphenylaminophenyl)naphthacene;
- 7,8,15,16-Tetraphenyl-benzo[a]pentacene;
- 2,3,5,6,11,12-Hexaphenylnaphthacene;
- 6,11-diphenyl-5,12-bis(4'-cyanophenyl)naphthacene;
- 6,11-diphenyl-5,12-bis(4'-(2-thienyl)phenyl)naphthacene; or
- 9,10,19,20-Tetraphenyl-tetrabenzo[a,c,j,l]naphthacene.

59. The organic light emitting device of claim 1 wherein the second component is a substituted or unsubstituted benzoxazolyl moiety, a substituted or unsubstituted benzthiozolyl moiety or a substituted or unsubstituted benzimidazolyl moiety.

60. The organic light emitting device of claim 1 wherein the dopant includes a substituted or unsubstituted DCM class moiety.

61. The organic light emitting device of claim 1 wherein the dopant includes DCJTB.

62. The organic light emitting device of claim 1 wherein the dopant includes a substituted or unsubstituted periflanthene moiety.

63. The organic light emitting device of claim 62 wherein the dopant includes Red 2.

64. The organic light emitting device of claim 1 wherein the dopant includes a substituted or unsubstituted coumarin moiety.

65. The organic light emitting device of claim 64 wherein the dopant includes C-6, C-545T, or C-525T.

66. The organic light emitting device of claim 1 wherein the dopant includes a substituted or unsubstituted quinacridone moiety.

67. The organic light emitting device of claim 66 wherein the dopant includes QA, DMQA, CFDMQA, or DPQA.

68. The organic light emitting device of claim 1 wherein the dopant includes a substituted or unsubstituted DPMB moiety.

69. The organic light emitting device of claim 68 wherein the dopant includes DPMB 1, DPMB 2, or DPMB 3.

70. The organic light emitting device of claim 1 wherein the dopant includes a substituted or unsubstituted indenoperylene moiety.

71. The organic light emitting device of claim 1 wherein the dopant includes Yellow-green 2.

72. The organic light emitting device of claim 1 wherein the dopant includes a substituted or unsubstituted naphthacene moiety.

73. The organic light emitting device of claim 72 wherein the dopant includes:
- 5,6,11,12-Tetraphenylnaphthacene (rubrene);
- 2,2'-[(6,11-diphenyl-5,12-naphthacenediyl)di-4,1-phenylene]bis(6-methylbenzothiazole) (Orange 2);
- 5,12-Bis(2-mesityl)-6,11-diphenyltetracene;
- 5,6,11,12-Tetrakis(2-naphthyl)tetracene;
- 10,10'-[(6,11-Diphenyl-5,12-naphthacenediyl)di-4,1-phenylene]bis[2,3,6,7-tetrahydro-1H,5H-benzothiazolo[5,6,7-ij]quinolizine;
- 5,6,13,14-Tetraphenylpentacene;
- 4,4'-(8,9-Dimethoxy-5,6,7,10,11,12-hexaphenyl-1,4-naphthacenediyl)bis[N,N-diphenylbenzenamine];
- 6,11-diphenyl-5,12-bis(4'-N,N-diphenylaminophenyl)naphthacene;
- 7,8,15,16-Tetraphenyl-benzo[a]pentacene; or
- 6,11-diphenyl-5,12-bis(4'-cyanophenyl)naphthacene.

74. The organic light emitting device of claim 1 wherein the dopant includes a substituted or unsubstituted BASB moiety.

75. The organic light emitting device of claim 74 wherein the dopant includes:
- 4-(Diphenylamino)-4'-[4-(diphenylamino)styryl]stilbene;
- 4-(Di-p-Tolylamino)-4'-[(di-p-tolylamino)styryl]stilbene (Blue-green 2);
- 4,4'-[(2,5-Dimethoxy-1,4-phenylene)di-2,1-ethenediyl]bis[N,N-bis(4-methylphenyl)benzenamine;
- 4,4'-(1,4-Naphthalenediyldi-2,1-ethenediyl)bis[N,N-bis(4-methylphenyl)benzenamine;
- 3,3'-(1,4-Phenylenedi-2,1-ethenediyl)bis[9-(4-ethylphenyl)-9H-carbazole;
- 4,4'-(1,4-Phenylenedi-2,1-ethenediyl)bis[N,N-diphenyl-1-naphthalenamine;
- 4,4'-[1,4-Phenylenebis(2-phenyl-2,1-ethenediyl)]bis[N,N-diphenylbenzenamine);
- 4,4',4''-(1,2,4-Benzenetriyltri-2,1-ethenediyl)tris[N,N-diphenylbenzenamine];
- 9,10-Bis[4-(di-p-tolylamino)styryl]anthracene; or
- α,α'-(1,4-Phenylenedimethylidyne)bis[4-(diphenylamino)-1-naphthaleneacetonitrile.

76. The organic light emitting device of claim 1 wherein the dopant includes a substituted or unsubstituted perylene.

77. The organic light emitting device of claim 76 wherein the dopant includes:

Perylene;

2,5,8,11-Tetra-tert-butylperylene (TBP);

2,8-Di-tert-Butylperylene;

Ovalene;

Dibenzo[b,ghi]perylene; or

Dibenzo[b,k]perylene.

78. The organic light emitting device of claim 1 wherein the dopant includes a substituted or unsubstituted ADPMB moiety.

79. The organic light emitting device of claim 78 wherein the dopant includes: Blue 2, ADPMB 1, or ADPMB 2.

80. The organic light emitting device of claim 1 wherein the first component of the mixture is an organic compound containing at least one perylene carbocyclic ring structure that has the formula:

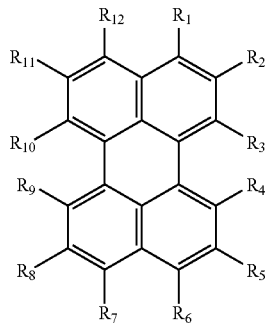

wherein:

substituents $R_1$ through $R_{12}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{12}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{12}$ substituents form a 1,2-benzo, 1,2-naphtho, 2,3-naphtho, 1,8-naphtho, 1,2-anthraceno, 2,3-anthraceno, 2,2'-biphenylene, 4,5-phenanthreno, 1,12-triphenyleno, 1,12-peryleno, 9,10-phenanthreno, 1,9-anthraceno, 1,10-phenanthreno, 2,3-phenanthreno, 1,2-phenanthreno, 1,10-pyreno, 1,2-pyreno, 2,3-peryleno, 3,4-fluorantheno, 2,3-fluorantheno, 1,2-fluorantheno, 3,4-peryleno, 7,8-fluorantheno, 8,9-fluorantheno, 2,3-triphenyleno, 1,2-triphenylno, ace, or indeno substituent or their alkyl or aryl substituted derivative.

81. The organic light emitting device of claim 1 wherein the first component of the mixture is an organic compound containing at least one perylene carbocyclic ring structure that has the formula:

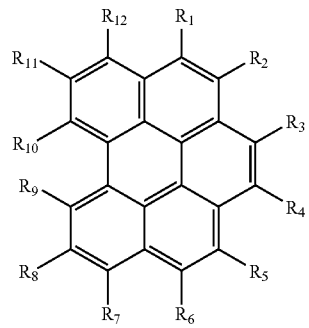

wherein:

substituents $R_1$ through $R_{12}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{12}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{12}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

82. The organic light emitting device of claim 1 wherein the first component of the mixture is an organic compound containing at least one perylene carbocyclic ring structure that has the formula:

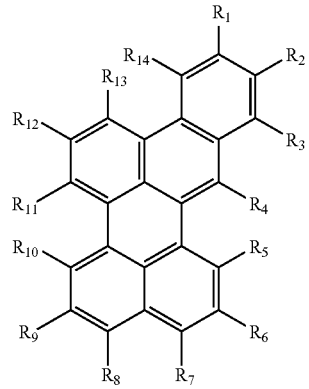

wherein:

substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

83. The organic light emitting device of claim 1 wherein the first component of the mixture is an organic compound containing at least one perylene carbocyclic ring structure that has the formula:

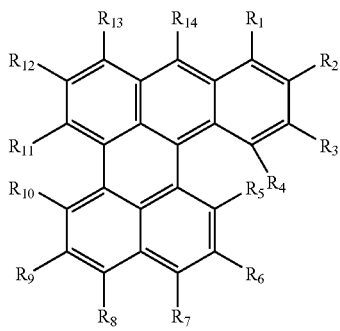

wherein:
substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

84. The organic light emitting device of claim 1 wherein the first component of the mixture is an organic compound containing at least one perylene carbocyclic ring structure that has the formula:

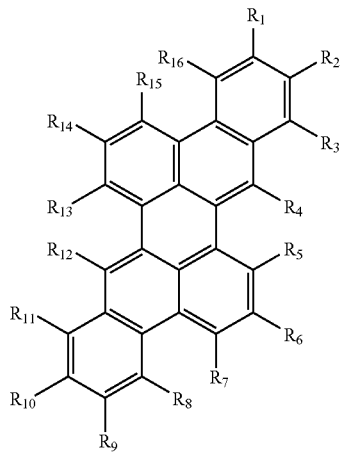

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

85. The organic light emitting device of claim 1 wherein the first component of the mixture is an organic compound containing at least one perylene carbocyclic ring structure that has the formula:

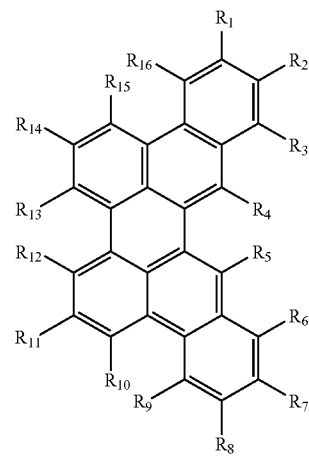

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

86. The organic light emitting device of claim 1 wherein the first component of the mixture is an organic compound containing at least one perylene carbocyclic ring structure that has the formula:

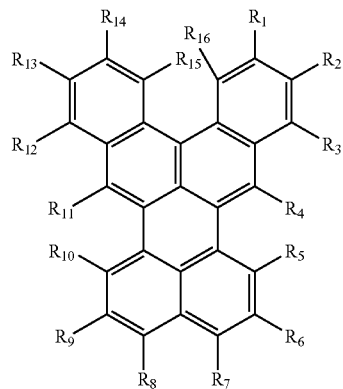

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

87. The organic light emitting device of claim 1 wherein the first component of the mixture is an organic compound containing at least one perylene carbocyclic ring structure that has the formula:

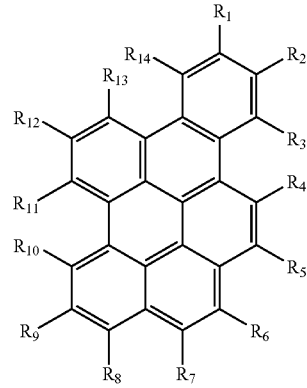

wherein:

substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

88. The organic light emitting device of claim 1 wherein the first component of the mixture is an organic compound containing at least one perylene carbocyclic ring structure that has the formula:

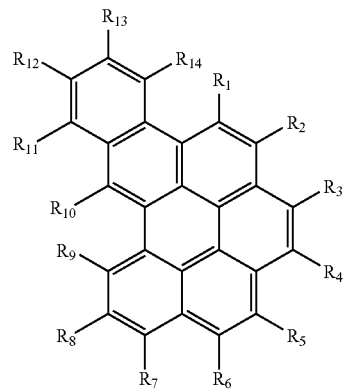

wherein:

substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

89. The organic light emitting device of claim 1 wherein the first component of the mixture is an organic compound containing at least one perylene carbocyclic ring structure that has the formula:

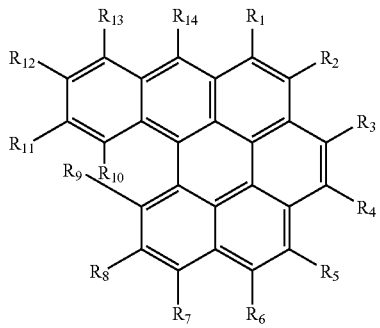

wherein:

substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

90. The organic light emitting device of claim 1 wherein the first component of the mixture is an organic compound containing at least one perylene carbocyclic ring structure that has the formula:

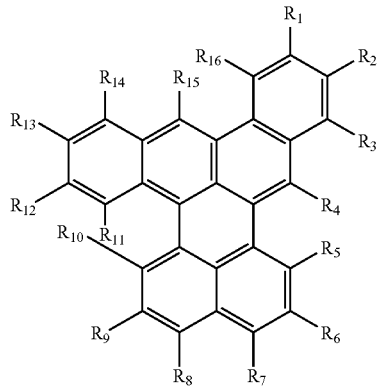

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

91. The organic light emitting device of claim 1 wherein the first component of the mixture is an organic compound containing at least one perylene carbocyclic ring structure that has the formula:

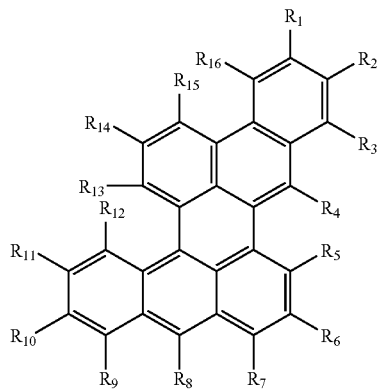

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

92. The organic light emitting device of claim 1 wherein the first component of the mixture is an organic compound containing at least one perylene carbocyclic ring structure that has the formula:

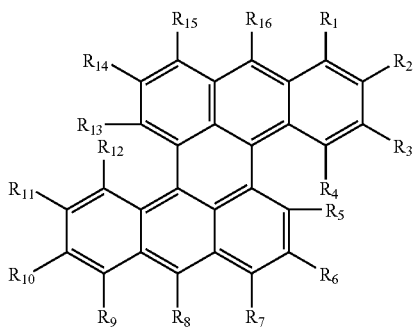

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

93. The organic light emitting device of claim 1 wherein the first component of the mixture is an organic compound containing at least one perylene carbocyclic ring structure that has the formula:

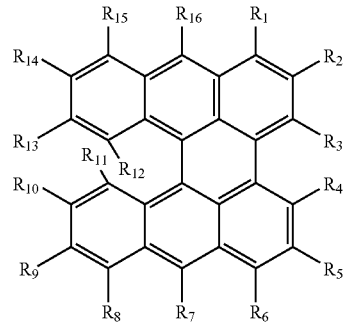

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

94. The organic light emitting device of claim 1 wherein the first component of the mixture is an organic compound containing at least one perylene carbocyclic ring structure that has the formula:

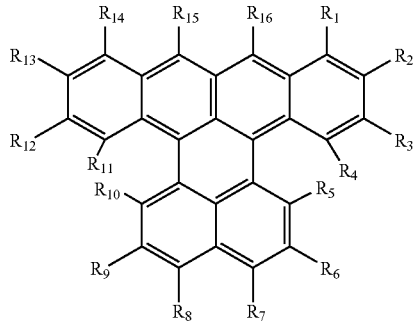

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

95. The organic light emitting device of claim 1 wherein the first component of the mixture is an organic compound containing at least one perylene carbocyclic ring structure that has the formula:

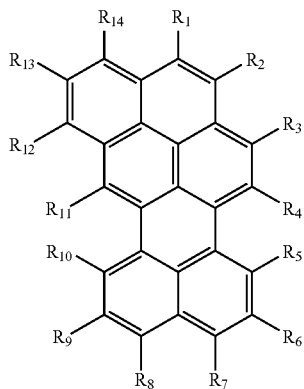

wherein:
substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

96. The organic light emitting device of claim 1 wherein the first component of the mixture is an organic compound containing at least one perylene carbocyclic ring structure that has the formula:

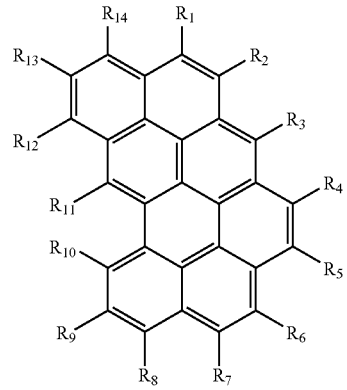

wherein:
substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

97. The organic light emitting device of claim 1 wherein the first component of the mixture is an organic compound containing at least one perylene carbocyclic ring structure that has the formula:

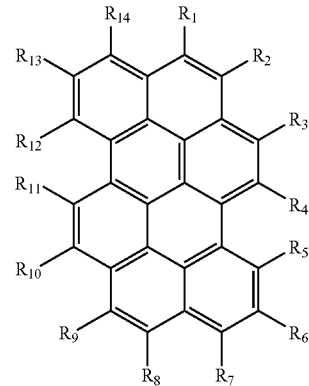

wherein:
substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

98. The organic light emitting device of claim 1 wherein the first component of the mixture is an organic compound containing at least one perylene carbocyclic ring structure that has the formula:

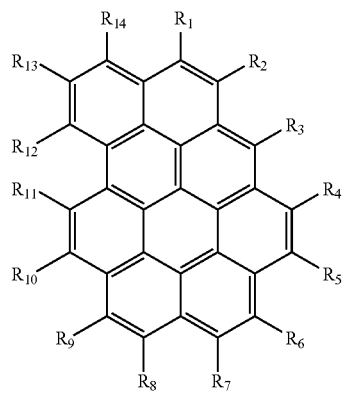

wherein:

substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

99. The organic light emitting device of claim 1 wherein the first component of the mixture is an organic compound containing at least one perylene carbocyclic ring structure that has the formula:

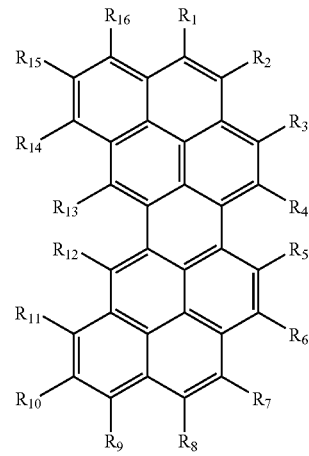

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

100. The organic light emitting device of claim 1 wherein the first component of the mixture is an organic compound containing at least one perylene carbocyclic ring structure that has the formula:

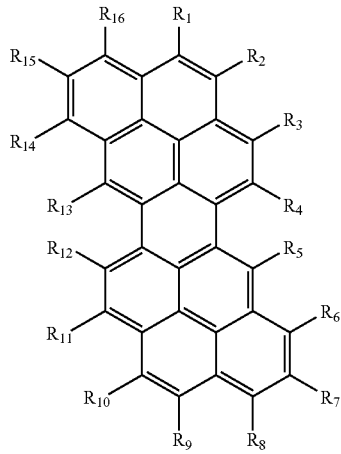

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

101. The organic light emitting device of claim 1 wherein the first component of the mixture is an organic compound containing at least one perylene carbocyclic ring structure that has the formula:

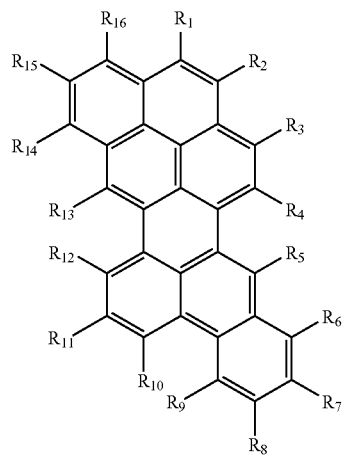

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

102. The organic light emitting device of claim 1 wherein the first component of the mixture is an organic compound containing at least one perylene carbocyclic ring structure that has the formula:

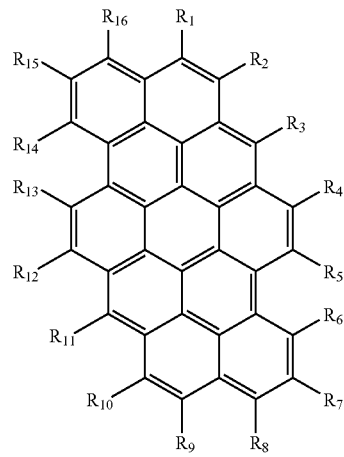

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

103. The organic light emitting device of claim 1 wherein the first component of the mixture is an organic compound containing at least one perylene carbocyclic ring structure that has the formula:

139

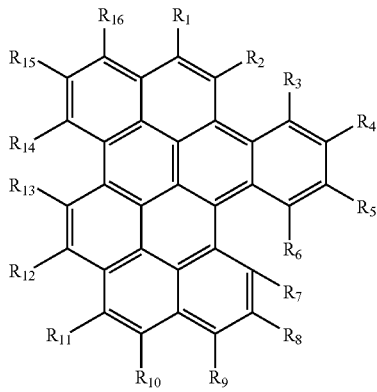

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

104. The organic light emitting device of claim 1 wherein the first component of the mixture is an organic compound containing at least one perylene carbocyclic ring structure that has the formula:

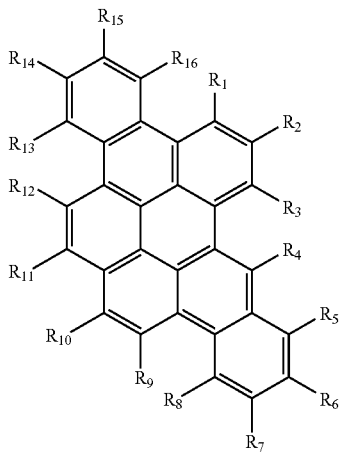

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

105. The organic light emitting device of claim 1 wherein the first component of the mixture is an organic compound containing at least one perylene carbocyclic ring structure that has the formula:

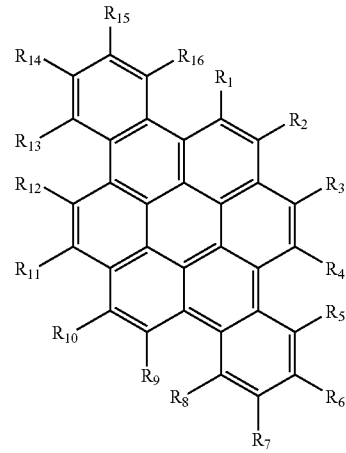

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-

FlAn, 8,9-FlAn, 2,3-TriP, 1,2-TriP, ace, or indeno substituent or their alkyl or aryl substituted derivative.

106. The organic light emitting device of claim 1 wherein the first component of the mixture is an organic compound containing at least one perylene carbocyclic ring structure that has the formula:

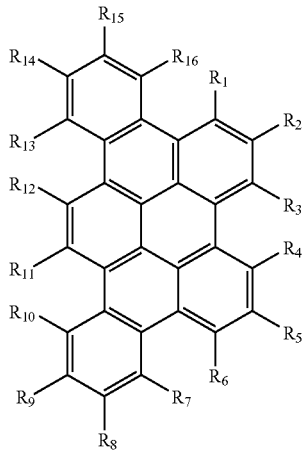

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

107. The organic light emitting device of claim 1 wherein the first component of the mixture is an organic compound containing at least one perylene carbocyclic ring structure that has the formula:

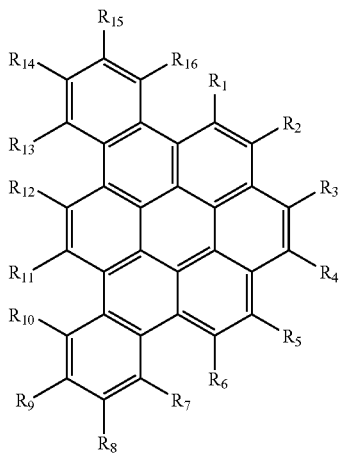

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

108. The organic light emitting device of claim 1 wherein the first component of the mixture is an organic compound containing at least one perylene carbocyclic ring structure that has the formula:

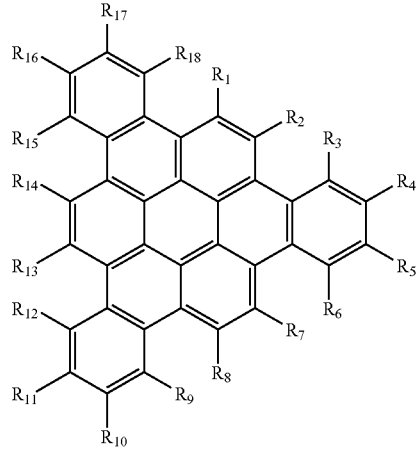

wherein:
substituents $R_1$ through $R_{18}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{18}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{18}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

109. The organic light emitting device of claim 1 wherein the first component of the mixture is an organic compound containing at least one perylene carbocyclic ring structure that has the formula:

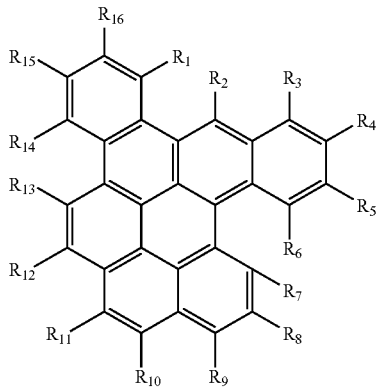

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

110. The organic light emitting device of claim 1 wherein the first component of the mixture is an organic compound containing at least one perylene carbocyclic ring structure that has the formula:

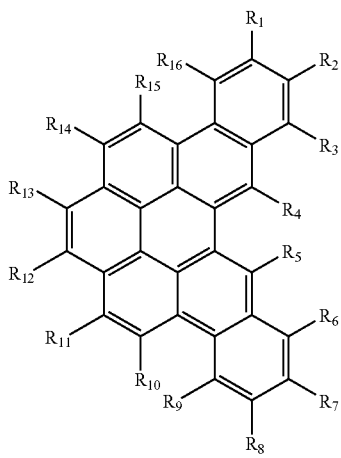

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

111. The organic light emitting device of claim 1 wherein the first component of the mixture is an organic compound containing at least one perylene carbocyclic ring structure that has the formula:

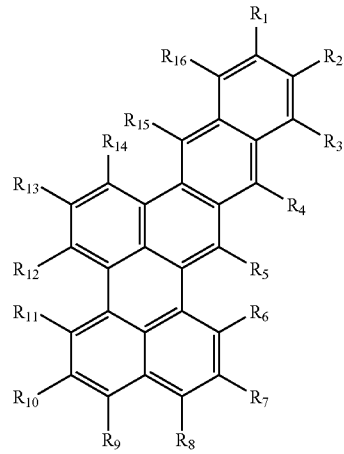

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

112. The organic light emitting device of claim 1 wherein the first component of the mixture is an organic compound containing at least one perylene carbocyclic ring structure that has the formula:

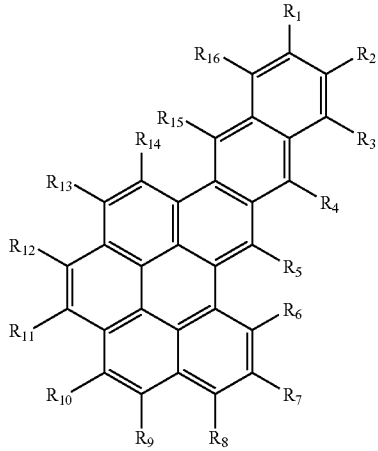

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

113. The organic light emitting device of claim 1 wherein the first component of the mixture is an organic compound containing at least one perylene carbocyclic ring structure that has the formula:

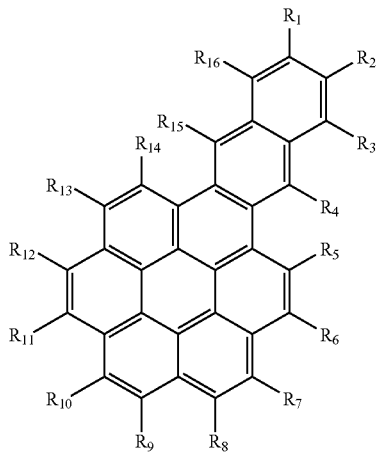

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

114. The organic light emitting device of claim 1 wherein the first component of the mixture is an organic compound containing at least one perylene carbocyclic ring structure that has the formula:

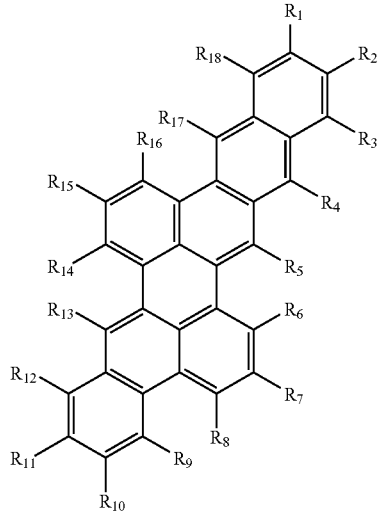

wherein:
substituents $R_1$ through $R_{18}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{18}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{18}$ substituents form a 1,2-benzo, 1,2-naphtho, 2,3-naph tho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

115. The organic light emitting device of claim 1 wherein the first component of the mixture is an organic compound containing at least one perylene carbocyclic ring structure that has the formula:

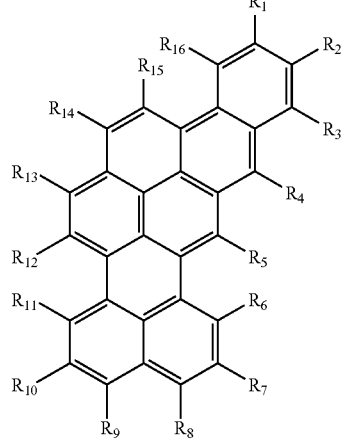

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

116. The organic light emitting device of claim 1 wherein the first component of the mixture is an organic compound containing at least one perylene carbocyclic ring structure that has the formula:

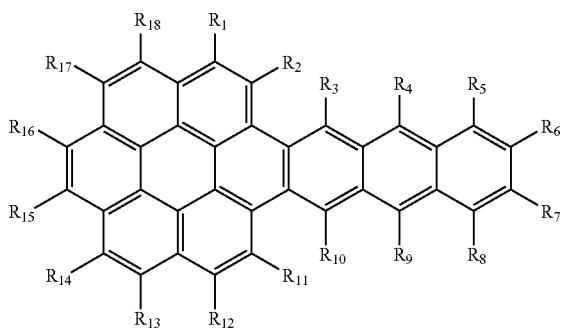

wherein:
substituents $R_1$ through $R_{18}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{18}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{18}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

117. The organic light emitting device of claim 1 wherein the first component of the mixture is an organic compound containing at least one perylene carbocyclic ring structure that has the formula:

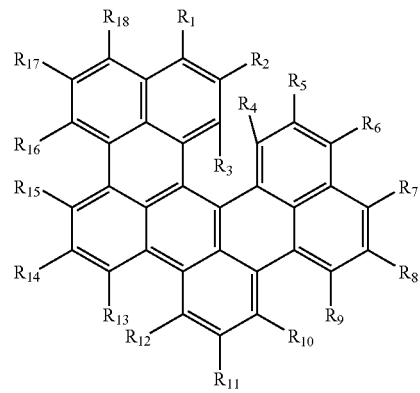

wherein:
substituents $R_1$ through $R_{18}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{18}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{18}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

118. The organic light emitting device of claim 1 wherein the first component of the mixture is an organic compound containing at least one perylene carbocyclic ring structure that has the formula:

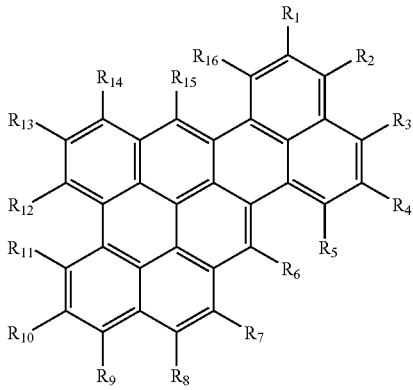

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

119. The organic light emitting device of claim 1 wherein the first component of the mixture is an organic compound containing at least one perylene carbocyclic ring structure that has the formula:

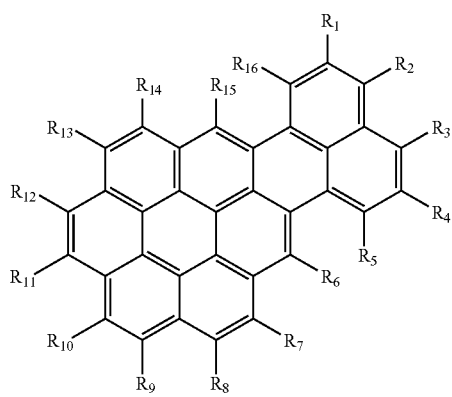

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

120. The organic light emitting device of claim 1 wherein the first component of the mixture is an organic compound containing at least one perylene carbocyclic ring structure that has the formula:

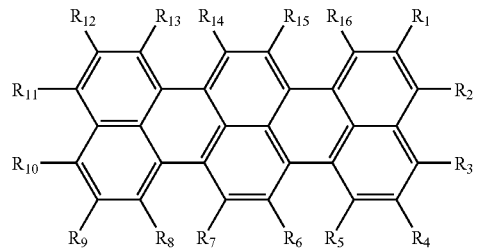

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

121. The organic light emitting device of claim 1 wherein the first component of the mixture is an organic compound containing at least one perylene carbocyclic ring structure that has the formula:

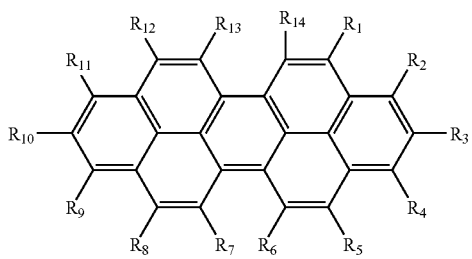

wherein:

substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

122. The organic light emitting device of claim 1 wherein the first component of the mixture is an organic compound containing at least one perylene carbocyclic ring structure that has the formula:

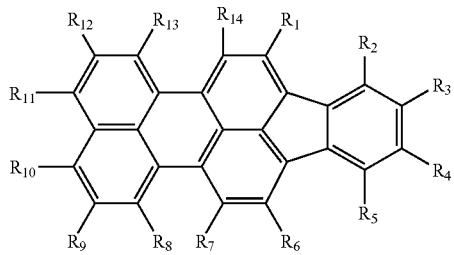

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

123. The organic light emitting device of claim 1 wherein the first component of the mixture is an organic compound containing at least one perylene carbocyclic ring structure that has the formula:

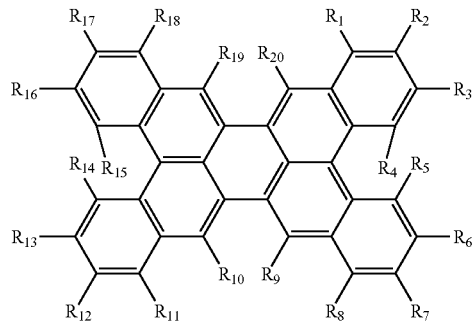

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{20}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{20}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

124. The organic light emitting device of claim 1 wherein the first component of the mixture is an organic compound containing at least one perylene carbocyclic ring structure that has the formula:

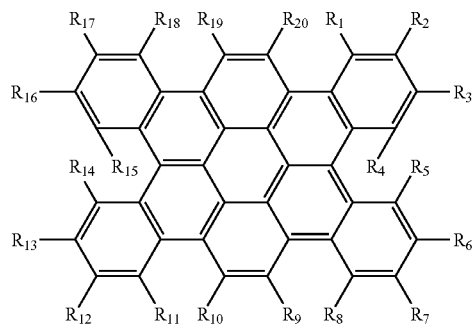

wherein:

substituents $R_1$ through $R_{20}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{20}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{20}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

125. The organic light emitting device of claim 1 wherein the first component of the mixture is an organic compound containing at least one perylene carbocyclic ring structure that has the formula:

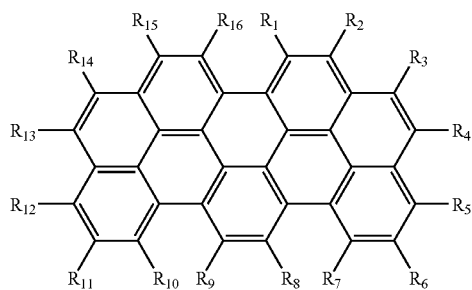

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

126. The organic light emitting device of claim 1 wherein the first component of the mixture is an organic compound containing at least one perylene carbocyclic ring structure that has the formula:

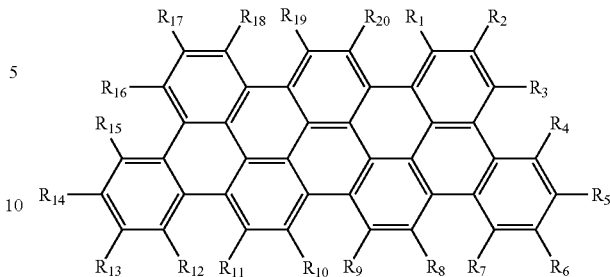

wherein:
substituents $R_1$ through $R_{20}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{20}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{20}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

127. The organic light emitting device of claim 1 wherein the first component of the mixture is an organic compound containing at least one perylene carbocyclic ring structure that has the formula:

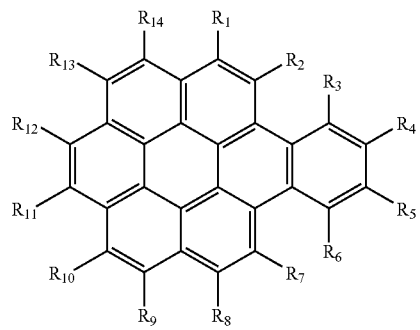

wherein:
substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

128. The organic light emitting device of claim 1 wherein the first component of the mixture is an organic compound containing at least one perylene carbocyclic ring structure that has the formula:

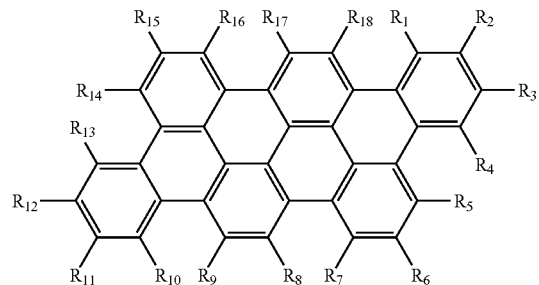

wherein:
substituents $R_1$ through $R_{18}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{18}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{18}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

129. The organic light emitting device of claim 1 wherein the first component of the mixture is an organic compound containing at least one perylene carbocyclic ring structure that has the formula:

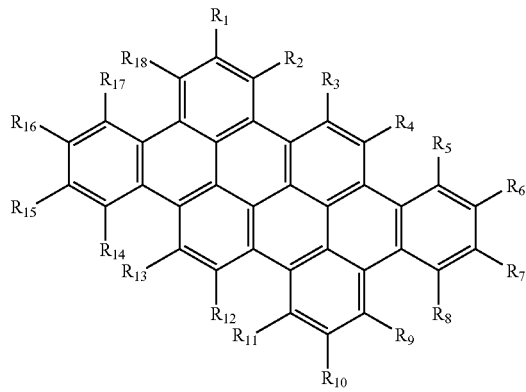

wherein:
substituents $R_1$ through $R_{18}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{18}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{18}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

130. The organic light emitting device of claim 1 wherein the first component of the mixture is an organic compound containing at least one perylene carbocyclic ring structure that has the formula:

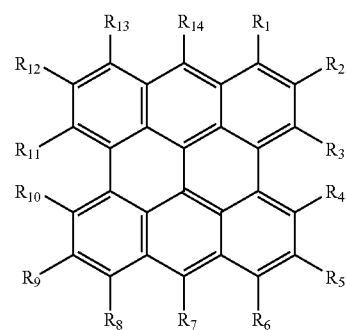

wherein:
substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

131. The organic light emitting device of claim 1 wherein the first component of the mixture is an organic compound containing at least one perylene carbocyclic ring structure that has the formula:

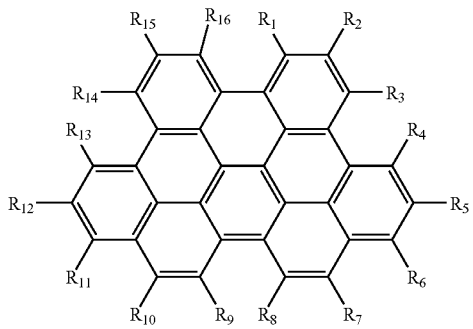

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

132. The organic light emitting device of claim 1 wherein the first component of the mixture is an organic compound containing at least one perylene carbocyclic ring structure that has the formula:

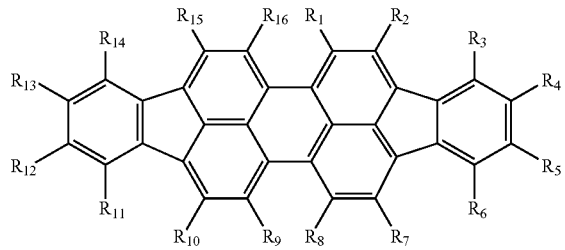

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

133. The organic light emitting device of claim 1 wherein the first component of the mixture is an organic compound containing at least one perylene carbocyclic ring structure that has the formula:

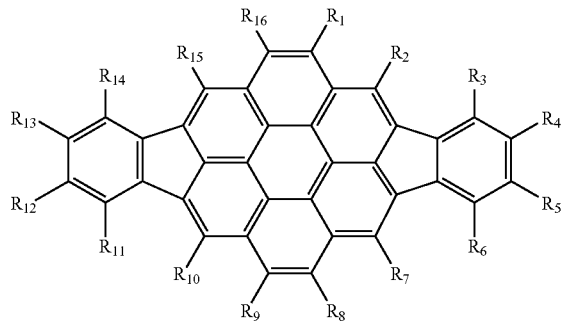

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

134. The organic light emitting device of claim 1 wherein the first component of the mixture is an organic compound containing at least one perylene carbocyclic ring structure that has the formula:

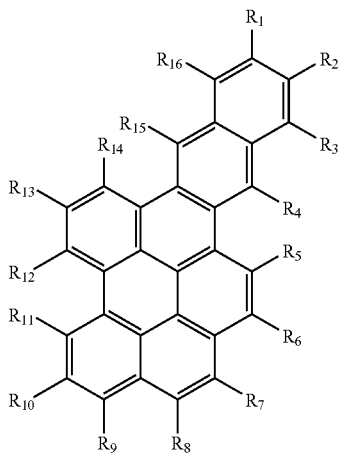

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

135. The organic light emitting device of claim 1 wherein the first component of the mixture is an organic compound containing at least one perylene carbocyclic ring structure that has the formula:

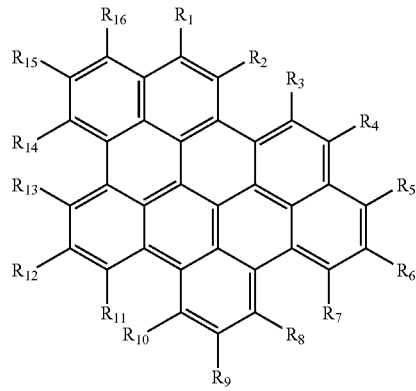

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

136. The organic light emitting device of claim 1 wherein the first component of the mixture is an organic compound containing at least one perylene carbocyclic ring structure that has the formula:

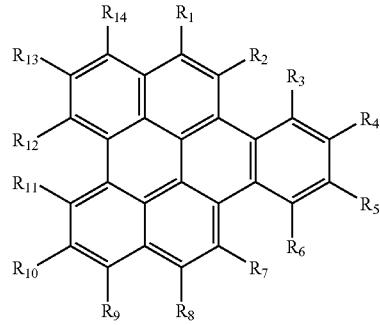

wherein:
substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

137. The organic light emitting device of claim 1 wherein the first component of the mixture is an organic compound containing at least one perylene carbocyclic ring structure that has the formula:

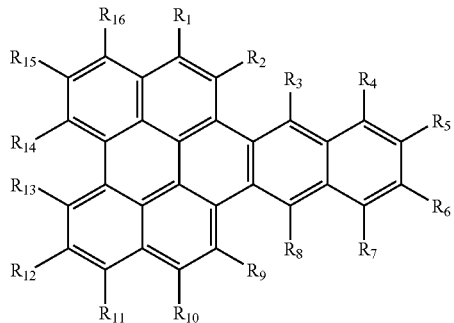

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

138. The organic light emitting device of claim 1 wherein the first component of the mixture is an organic compound containing at least one perylene carbocyclic ring structure that has the formula:

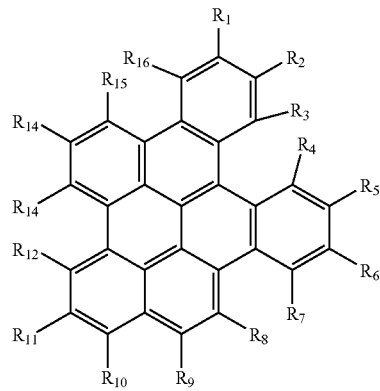

wherein:

substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

139. The organic light emitting device of claim 1 wherein the first component of the mixture is an organic compound containing at least one perylene carbocyclic ring structure that has the formula:

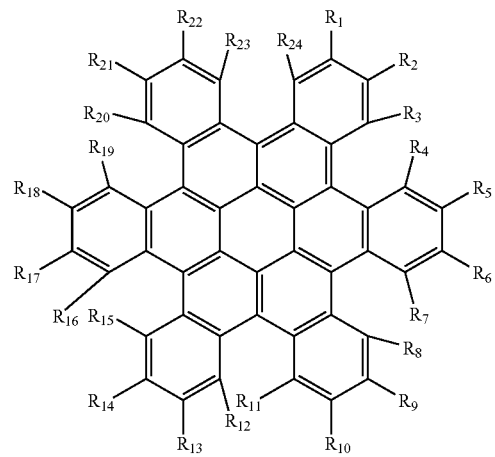

wherein:
substituents $R_1$ through $R_{24}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{24}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{24}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

140. The organic light emitting device of claim 1 wherein the first component of the mixture is an organic compound containing at least one perylene carbocyclic ring structure that has the formula:

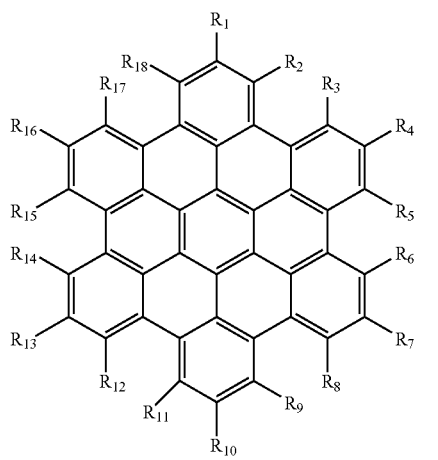

wherein:
substituents $R_1$ through $R_{18}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{18}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{18}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

141. The organic light emitting device of claim 1 wherein the first component of the mixture is an organic compound containing at least one perylene carbocyclic ring structure that has the formula:

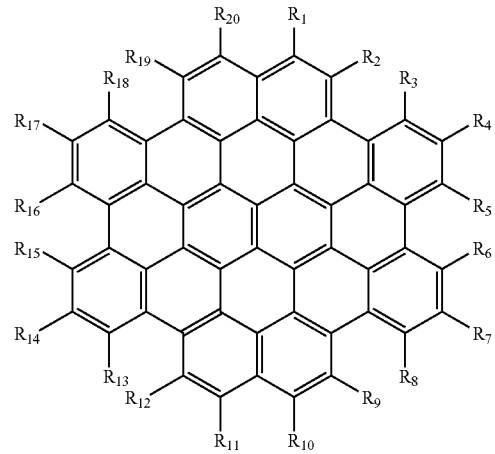

wherein:
substituents $R_1$ through $R_{20}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{20}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{20}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

142. The organic light emitting device of claim 1 wherein the first component of the mixture is an organic compound containing at least one perylene carbocyclic ring structure that has the formula:

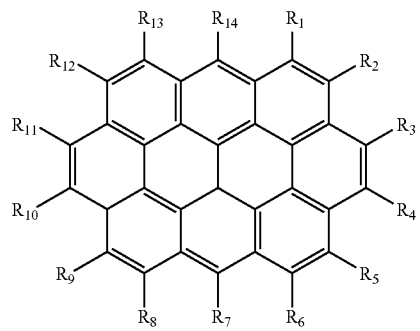

wherein:
substituents $R_1$ through $R_{14}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{14}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{14}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

143. The organic light emitting device of claim 1 wherein the first component of the mixture is an organic compound containing at least one perylene carbocyclic ring structure that has the formula:

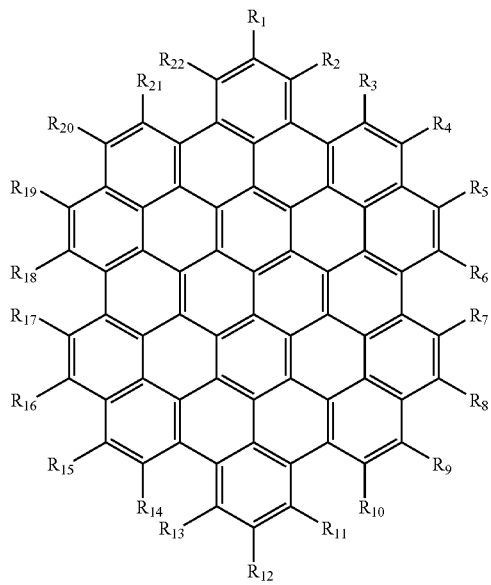

wherein:
substituents $R_1$ through $R_{22}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{22}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{22}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

144. The organic light emitting device of claim 1 wherein the first component of the mixture is an organic compound containing at least one perylene carbocyclic ring structure that has the formula:

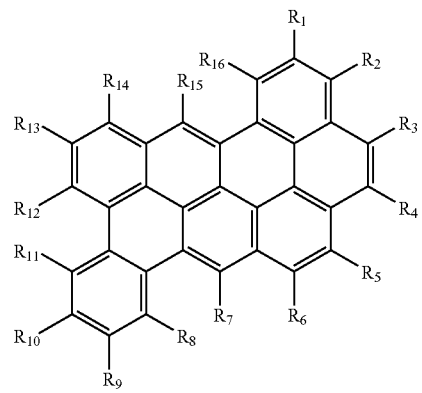

wherein:
substituents $R_1$ through $R_{16}$ are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof; or any two adjacent $R_1$ through $R_{16}$ substituents form an annelated benzo-, naphtho-, anthra-, phenanthro-, fluorantheno-, pyreno-, triphenyleno-, or peryleno-substituent or its alkyl or aryl substituted derivative; or any two $R_1$ through $R_{16}$ substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

145. The organic light emitting device of claim 1 wherein the first component of the mixture is an organic compound containing at least one perylene carbocyclic ring structure that can be drawn using only fully aromatic benzene rings so as to form graphite-like segments:

-continued
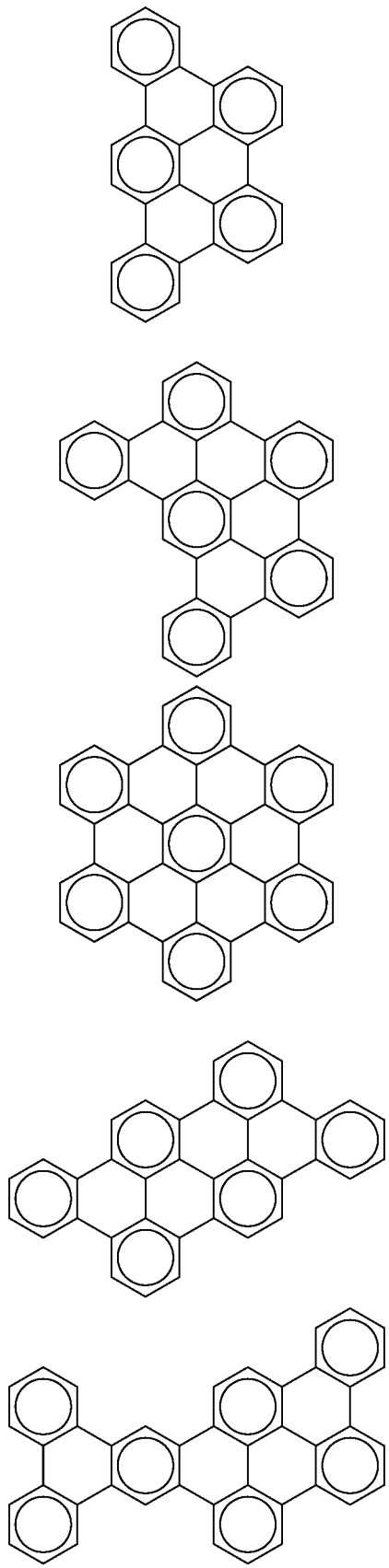
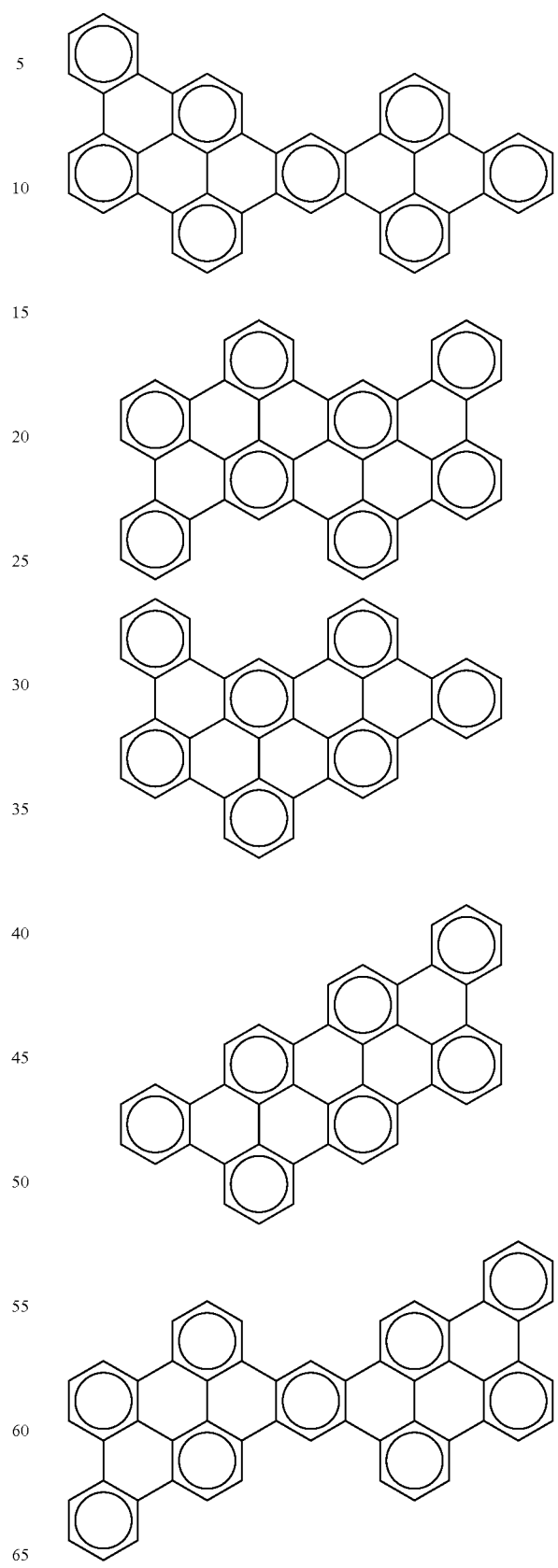

-continued
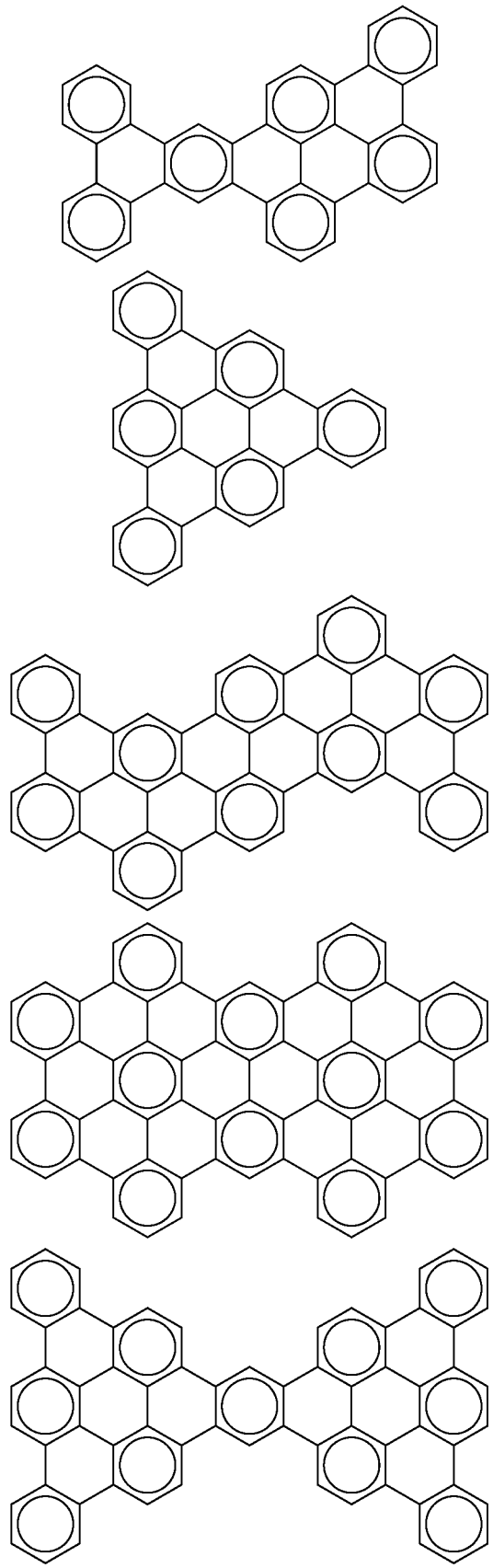

-continued

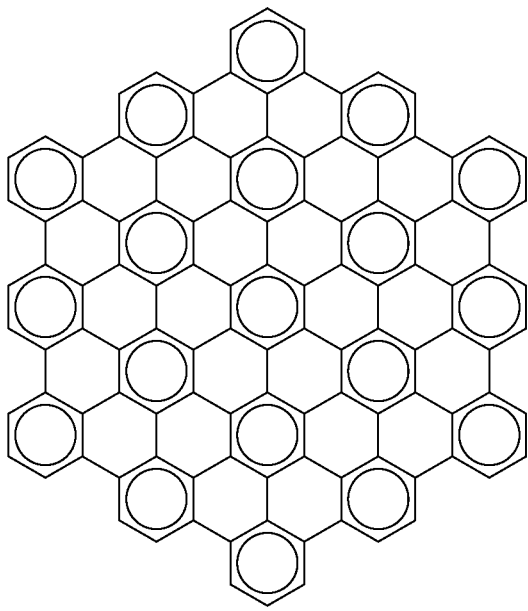

wherein:

substituents in each position for each compound and analogous compounds of the homological series are each individually hydrogen, fluoro, cyano, alkoxy, aryloxy, trialkylsilyl, triarylsilyl, diarylalkylsilyl, dialkylarylsilyl, keto, dicyanomethyl, alkyl of from 1 to 24 carbon atoms, alkenyl of from 1 to 24 carbon atoms, alkynyl of from 1 to 24 carbon atoms, aryl of from 5 to 30 carbon atoms, substituted aryl, heterocycle containing at least one nitrogen atom, or at least one oxygen atom, or at least one sulfur atom, or at least one boron atom, or at least one phosphorus atom, or at least one silicon atom, or any combination thereof, or any two adjacent substituents form an annelated benzo-, naphtho-, anthra-, phenanthro-, fluorantheno-, pyreno-, triphenyleno-, or peryleno-substituent or its alkyl or aryl substituted derivative; or any two substituents form a 1,2-benzo, 1,2-naphtho, 2,3-naphtho, 1,8-naphtho, 1,2-anthraceno, 2,3-anthraceno, 2,2'-BP, 4,5-PhAn, 1,12-TriP, 1,12-Per, 9,10-PhAn, 1,9-An, 1,10-PhAn, 2,3-PhAn, 1,2-PhAn, 1,10-Pyr, 1,2-Pyr, 2,3-Per, 3,4-FlAn, 2,3-FlAn, 1,2-FlAn, 3,4-Per, 7,8-FlAn, 8,9-FlAn, 2,3-TriP, 1,2-TriP, ace, or indeno substituent or their alkyl or aryl substituted derivative.

\* \* \* \* \*

UNITED STATES PATENT AND TRADEMARK OFFICE
CERTIFICATE OF CORRECTION

PATENT NO. : 7,175,922 B2
APPLICATION NO. : 10/691326
DATED : February 13, 2007
INVENTOR(S) : Viktor V. Jarikov et al.

It is certified that error appears in the above-identified patent and that said Letters Patent is hereby corrected as shown below:

| | |
|---|---|
| Column 117, line 19 | After "substrate;" please insert --and--. |
| Column 118, line 27 | After "is", please insert --in--. |
| Column 120, line 20 | Please delete "diphenylaminonaphthalen" and insert --diphenylaminonaphthalene-- |
| Column 121, line 20 | Please delete "fluoren" and insert --fluorene--. |
| Column 121, lines 55 and 56 | Please delete "benzthiozolyl" and insert --benzothiazolyl--. |
| Column 122, line 59 | Please delete "N-diphenylbenzenamine);" and insert --N-diphenylbenzenamine];-- |
| Column 123, line 61 | Please delete "1,2-triphenylno" and insert --1,2-triphenyleno-- |
| Column 127, line 21 | Please delete "3,4-FLAn," and insert --3,4-FlAn,-- |
| Column 127, line 25 | Please delete "1,2-FLAn," and insert --1,2-FlAn,-- |
| Column 146, line 67 and Column 147, line 1 | Please delete "2,3-naph tho," and insert --2,3-naphtho,--. |
| Column 151, line 17 of claim 121 | Please delete "$R_{16}$" and insert -- $R_{14}$-- |
| Column 151, line 6 of claim 122 | Please delete "$R_{16}$" and insert -- $R_{14}$-- |
| Column 152, line 6 of claim 123 | Please delete "$R_{16}$" and insert -- $R_{20}$-- |

UNITED STATES PATENT AND TRADEMARK OFFICE
CERTIFICATE OF CORRECTION

PATENT NO. : 7,175,922 B2
APPLICATION NO. : 10/691326
DATED : February 13, 2007
INVENTOR(S) : Viktor V. Jarikov et al.

It is certified that error appears in the above-identified patent and that said Letters Patent is hereby corrected as shown below:

Column 172, line 18 of claim 145    Please delete "thereof," and insert --thereof;--

Signed and Sealed this

Eighteenth Day of September, 2007

JON W. DUDAS
*Director of the United States Patent and Trademark Office*